US012806222B2

(12) United States Patent
Zangi et al.

(10) Patent No.: US 12,806,222 B2
(45) Date of Patent: Nov. 24, 2026

(54) GENE DELIVERY SYSTEMS FOR TREATMENT OF HEART FAILURE

(71) Applicant: ICAHN SCHOOL OF MEDICINE AT MOUNT SINAI, New York, NY (US)

(72) Inventors: Lior Zangi, New York, NY (US); Ajit Magadum, New York, NY (US)

(73) Assignee: Icahn School of Medicine at Mount Sinai, New York, NY (US)

( * ) Notice: Subject to any disclaimer, the term of this patent is extended or adjusted under 35 U.S.C. 154(b) by 1163 days.

(21) Appl. No.: 17/775,707

(22) PCT Filed: Nov. 11, 2020

(86) PCT No.: PCT/US2020/059943
§ 371 (c)(1),
(2) Date: May 10, 2022

(87) PCT Pub. No.: WO2021/096911
PCT Pub. Date: May 20, 2021

(65) Prior Publication Data

US 2022/0347204 A1 Nov. 3, 2022

Related U.S. Application Data

(60) Provisional application No. 62/933,681, filed on Nov. 11, 2019.

(51) Int. Cl.

| | |
|---|---|
| ***A61K 31/7105*** | (2006.01) |
| ***A61K 45/06*** | (2006.01) |
| ***A61P 9/04*** | (2006.01) |
| ***A61P 9/10*** | (2006.01) |
| ***C12N 9/12*** | (2006.01) |

(52) U.S. Cl.
CPC .......... *A61K 31/7105* (2013.01); *A61K 45/06* (2013.01); *A61P 9/04* (2018.01); *A61P 9/10* (2018.01); *C12N 9/1205* (2013.01); *C12Y 207/01149* (2013.01)

(58) Field of Classification Search
CPC .. A61K 31/7105; A61K 38/45; A61K 48/005; A61K 48/0066; A61K 31/7084; A61P 9/04; A61P 9/10; C12Y 207/01149
See application file for complete search history.

(56) References Cited

U.S. PATENT DOCUMENTS

2019/0203226 A1 7/2019 Zangi et al.
2019/0241633 A1 8/2019 Fotin-Mleczek et al.

OTHER PUBLICATIONS

Bosch et al. The transverse aortic constriction heart failure animal model: a systematic review and meta-analysis. Heart Failure Reviews (2021) 26:1515-1524 (Year: 2021).*
Tham et al. Pathophysiology of cardiac hypertrophy and heart failure: signaling pathways and novel therapeutic targets. Arch Toxicol (2015) 89:1401-1438 (Year: 2015).*
Magadum et al., 2019, mRNA-Based Protein Replacement Therapy for the Heart, Mol Ther, 27(4):785-793.
Kondrat, Jason, et al.; "Synthesis of Modified mRNA for Myocardial Delivery"; Cardiac Gene Therapy: Methods and Protocols, Methods in Molecular Biology 2017; 8:127-138.
Al-Ramahi, Ismael, et al.; "Inhibition of PIP4γ ameliorates the pathological effects of mutant huntingtin protein"; eLife 2017; 6(e29123):1-25.
Mackey, Ashley M., et al.; "PIP4kγ is a substrate for mTORC1 that maintains basal mTORC1 signaling during starvation"; Sci. Signal 2015; 7(350):1-25.
Volkers, Mirko, et al.; "Pathological hypertrophy amelioration by PRAS40-mediated inhibition of mTORC1"; PNAS 2013; 110(31):12661-12666.
DeAlmeida et al., "Transverse aortic constriction in mice." J Vis Exp. Apr. 21, 2010;(38):1729.

* cited by examiner

*Primary Examiner* — Taeyoon Kim
(74) *Attorney, Agent, or Firm* — Heslin Rothenberg Farley & Mesiti P.C.

(57) ABSTRACT

The present disclosure generally relates to compositions and methods of use thereof for treating heart failure encompassing administering a composition of modified mRNA (modRNA) encoding for type 2 phosphatidylinositol-5-phosphate 4-kinase gamma (pip4k2c) to heart tissue of a subject in need thereof.

13 Claims, 35 Drawing Sheets

Specification includes a Sequence Listing.

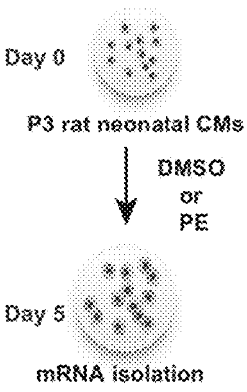
FIG. 3A
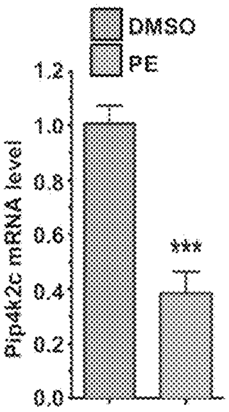
FIG. 3B
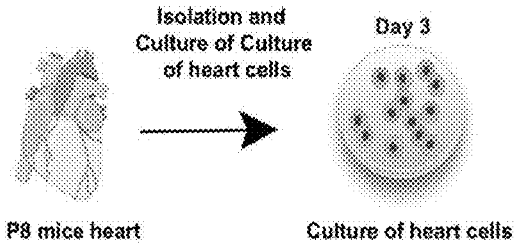
FIG. 3C
FIG. 3D
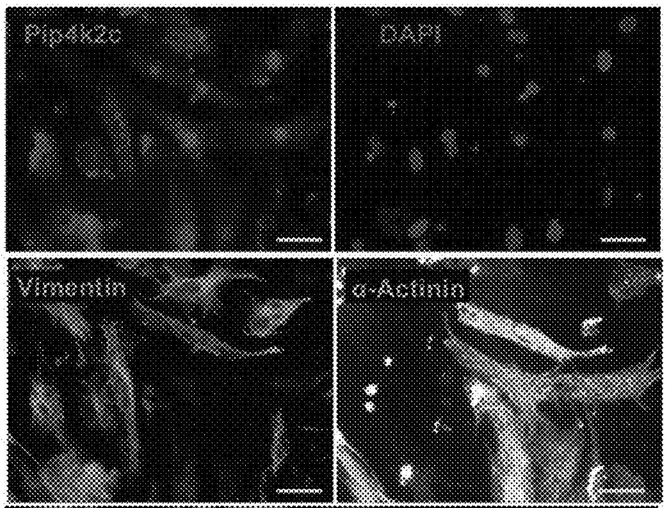
FIG. 3E
FIG. 3F
FIG. 3G
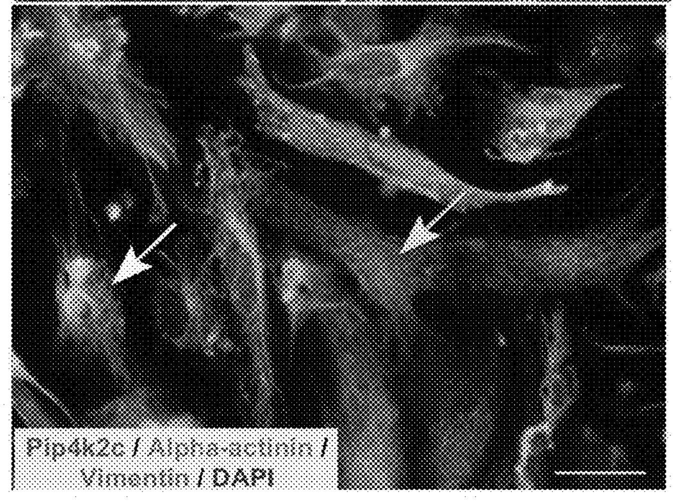
FIG. 3H FIG. 5A FIG. 5B
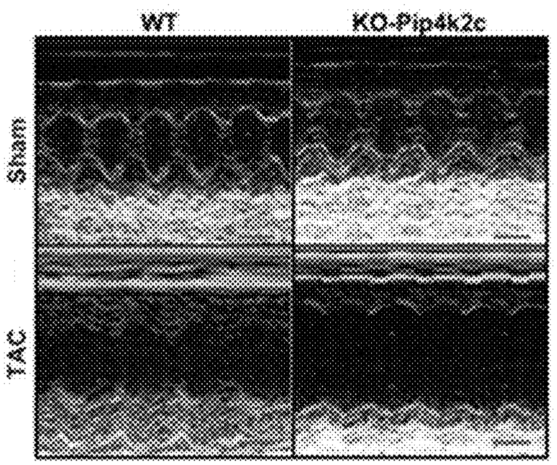
FIG. 5C FIG. 5D
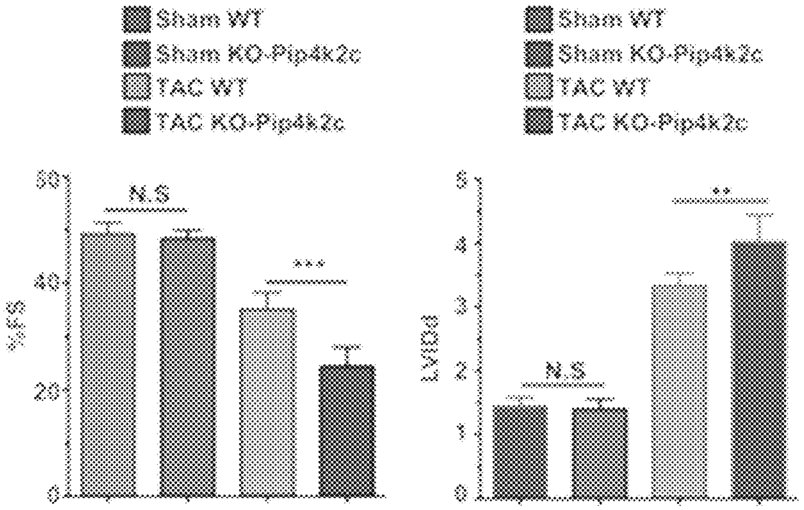
FIG. 5E FIG. 5F

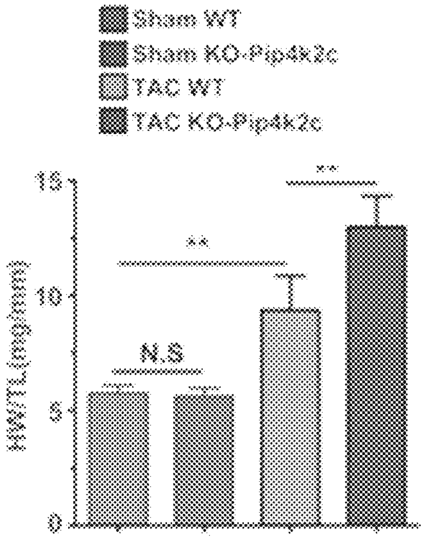
FIG. 6A
FIG. 6B FIG. 6C
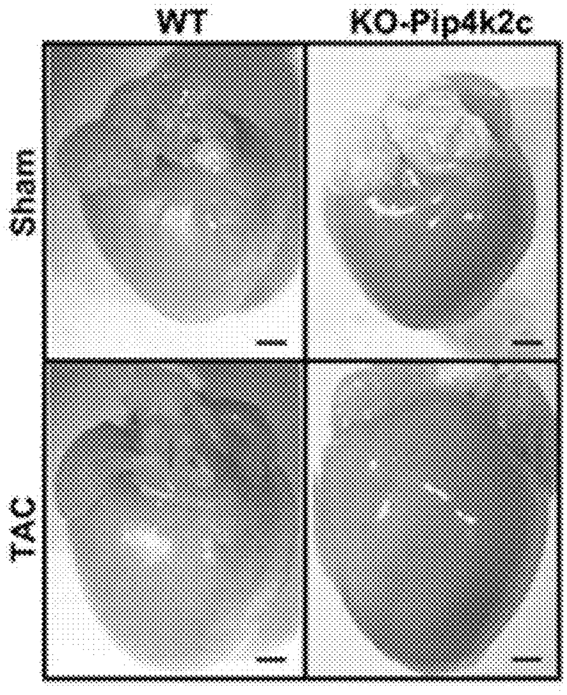
FIG. 6D FIG. 6E
FIG. 6F FIG. 6G
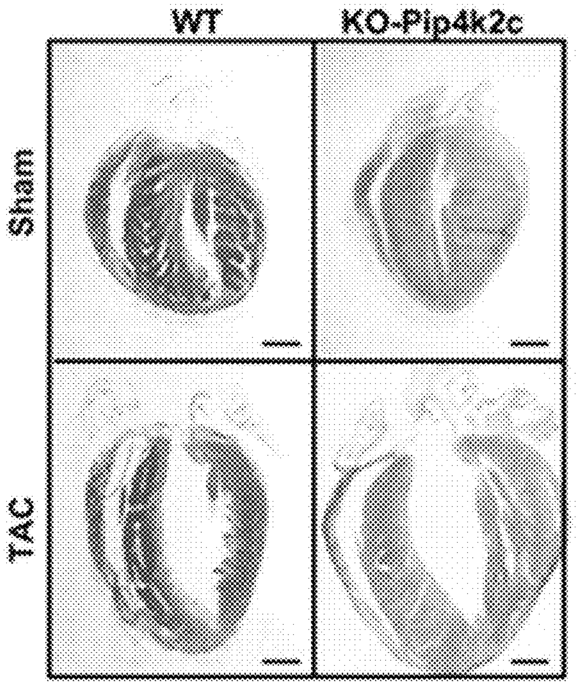
FIG. 6H FIG. 6I FIG. 7A FIG. 7B
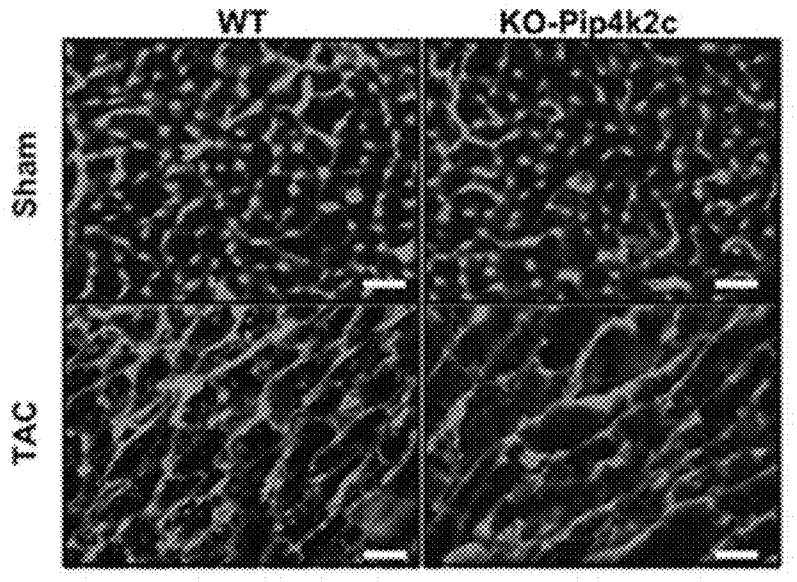
FIG. 7C FIG. 7D
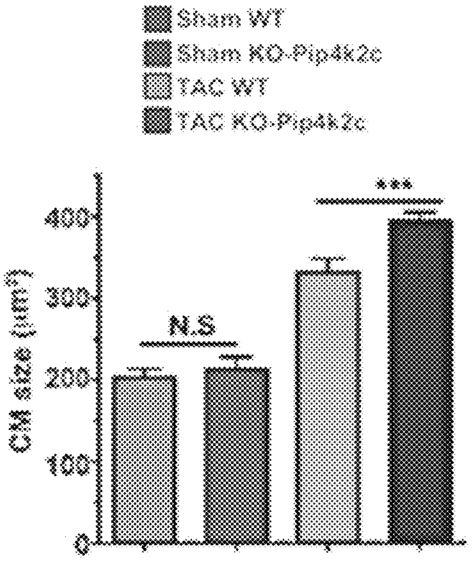
FIG. 7E FIG. 9A FIG. 9B
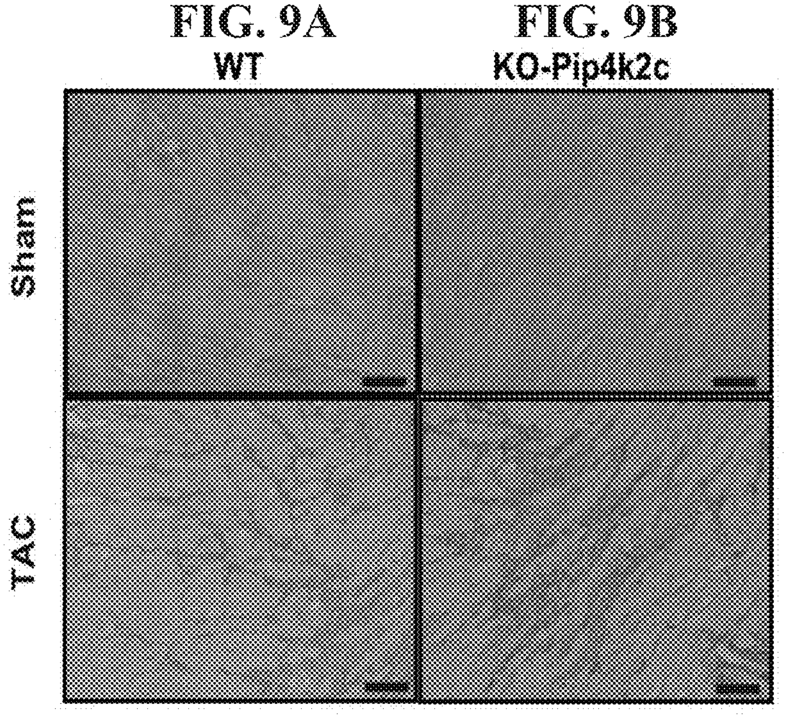
FIG. 9C FIG. 9D
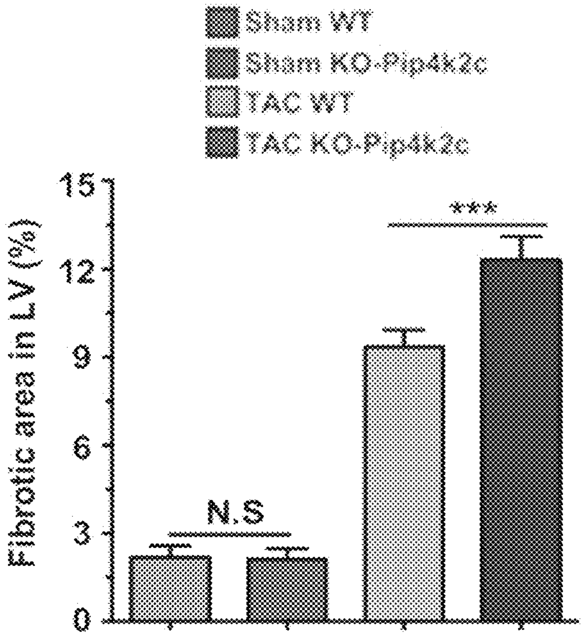
FIG. 9E FIG. 9F FIG. 9G FIG. 9H
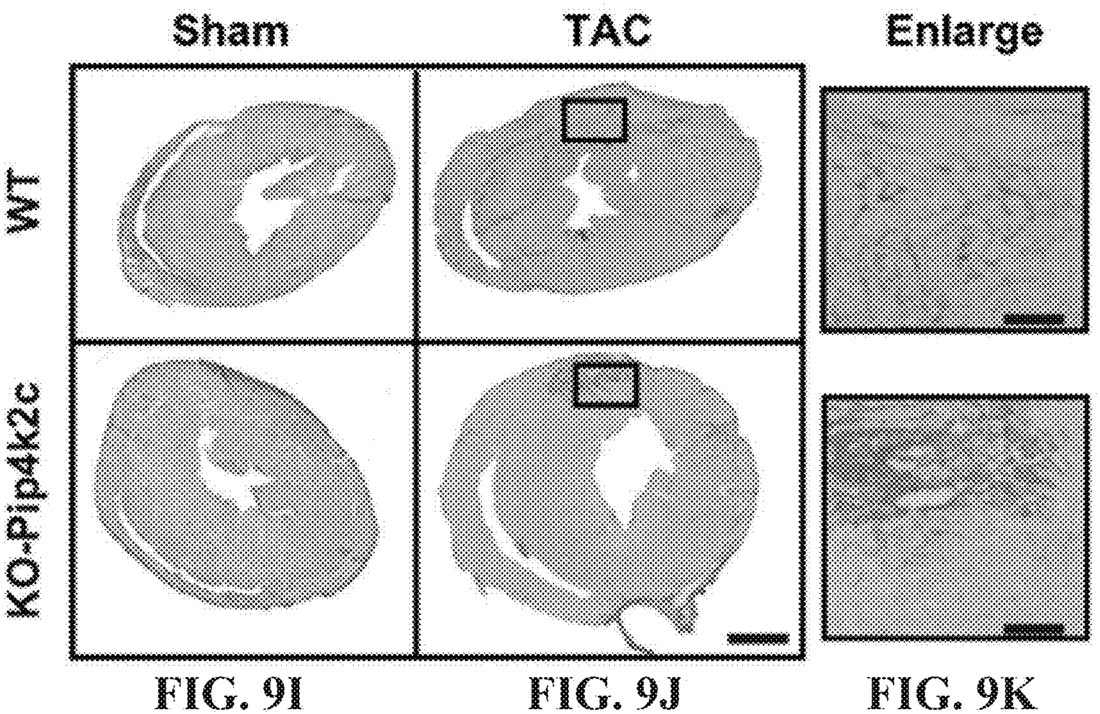
FIG. 9I FIG. 9J FIG. 9K
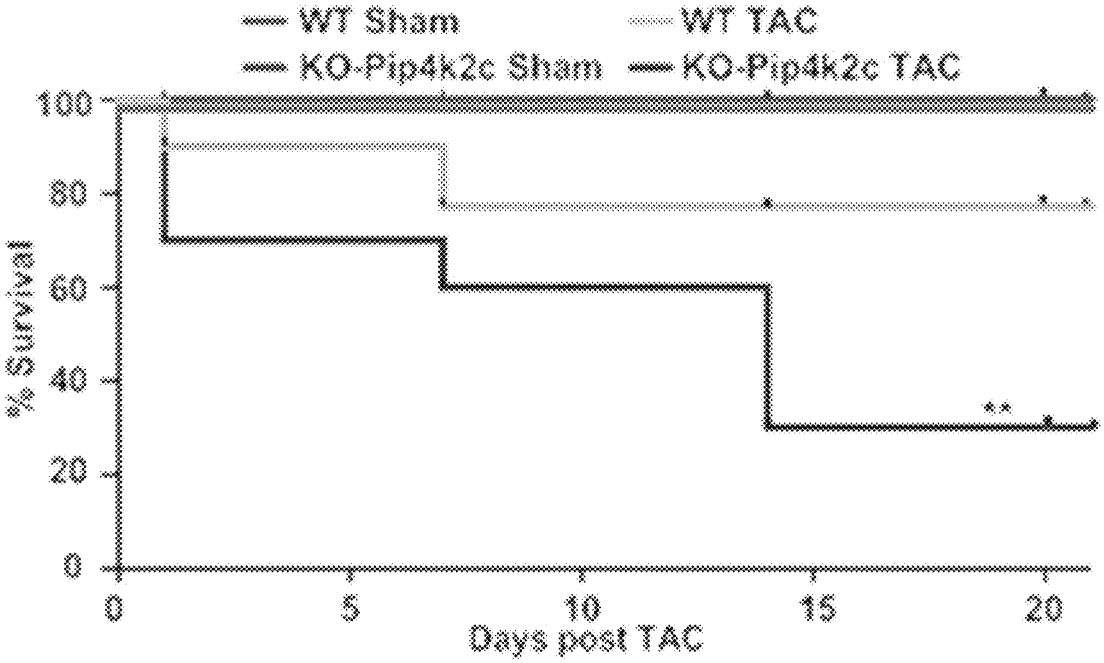
FIG. 10

α-Actinin / DAPI

Troponin T / DAPI

WGA / DAPI

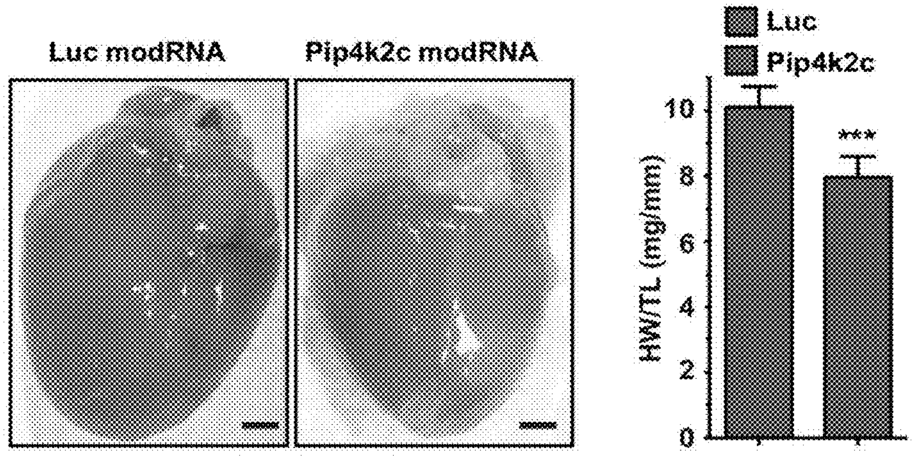
FIG. 15A FIG. 15B FIG. 15C
FIG. 16A
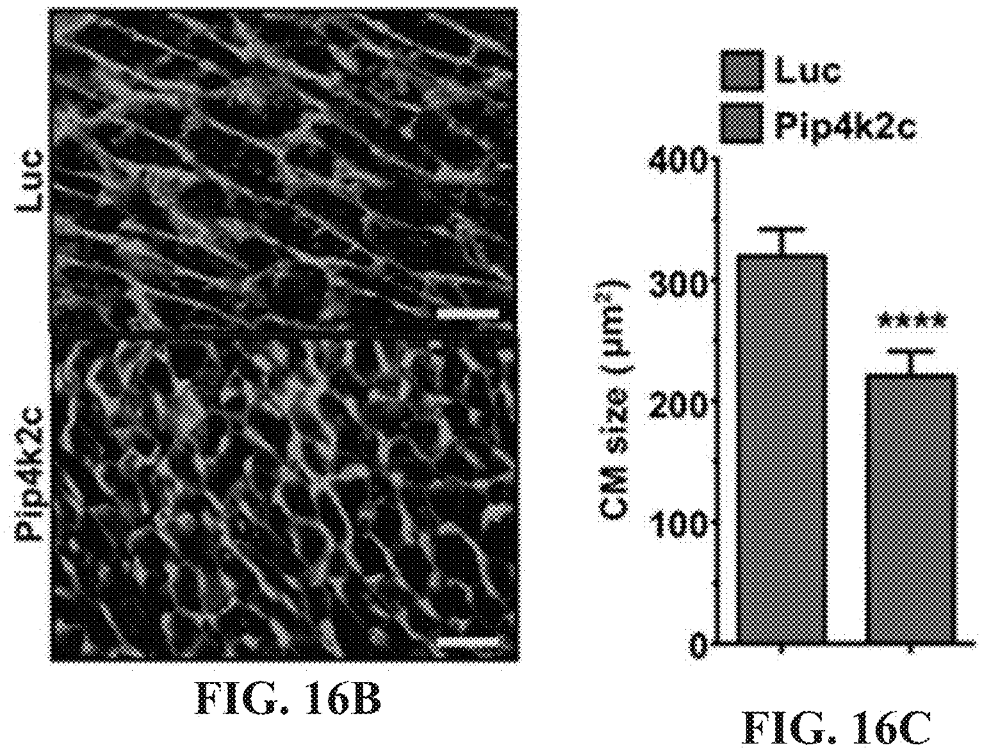
FIG. 16B
FIG. 16C

FIG. 18A
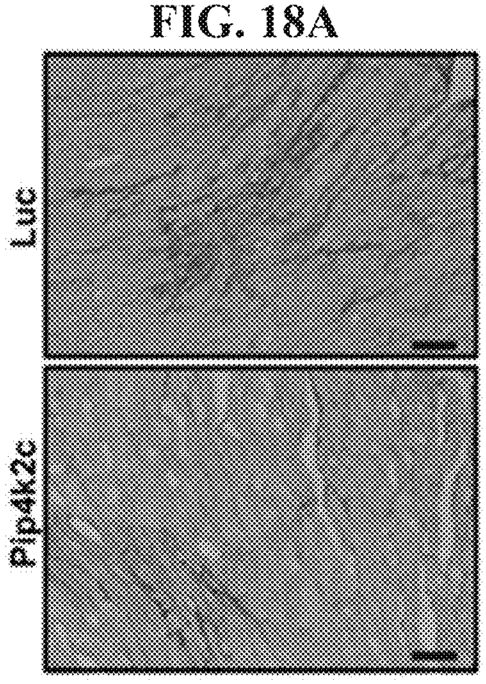
FIG. 18B
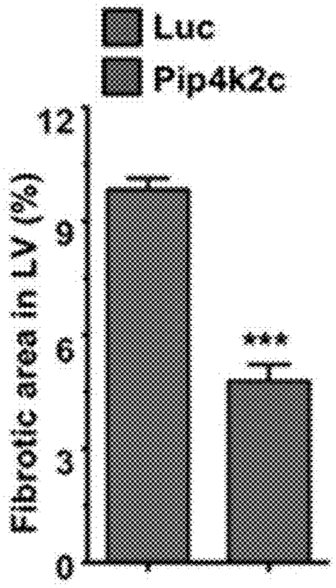
FIG. 18C
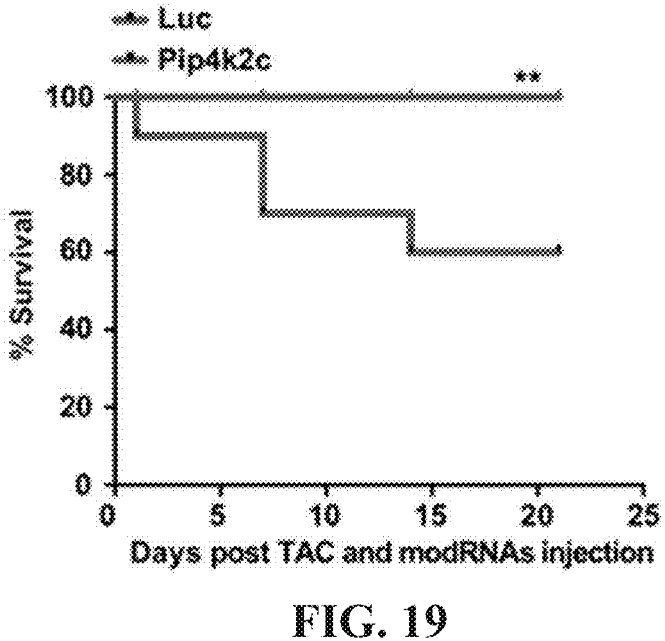
FIG. 19

FIG. 20A FIG. 20B FIG. 20C FIG. 20D
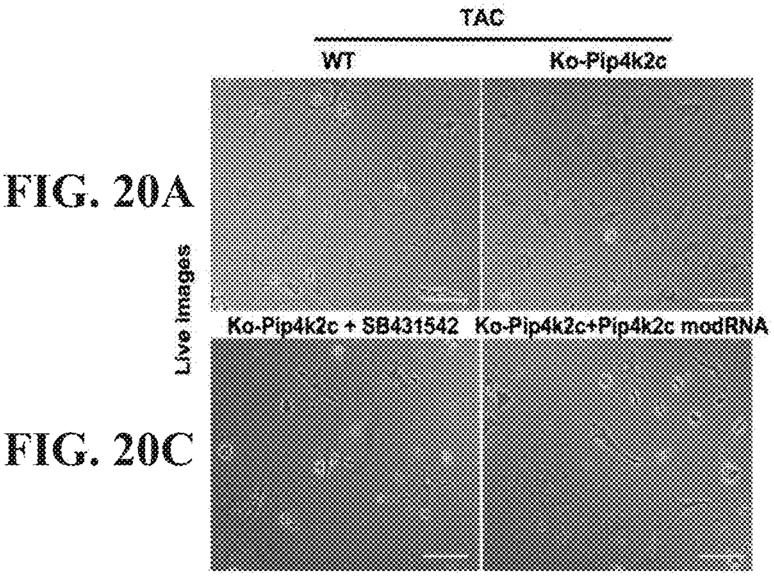
FIG. 20E FIG. 20F FIG. 20G FIG. 20H
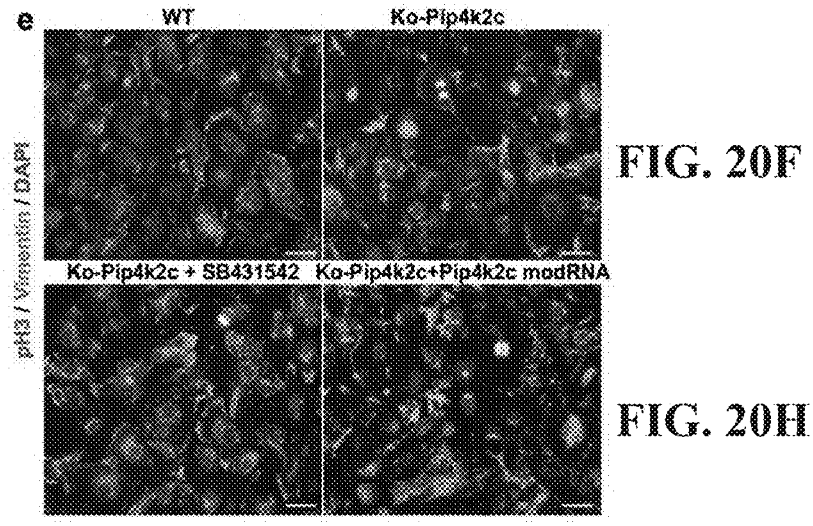
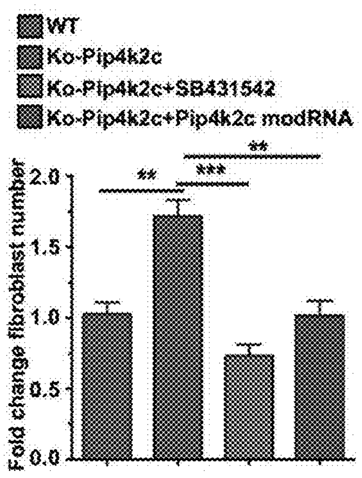
FIG. 20I
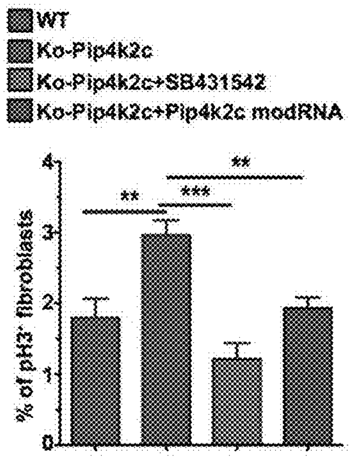
FIG. 20J FIG. 26A
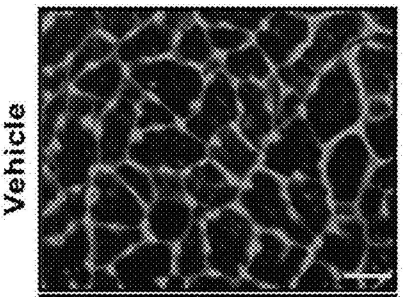
FIG. 26B
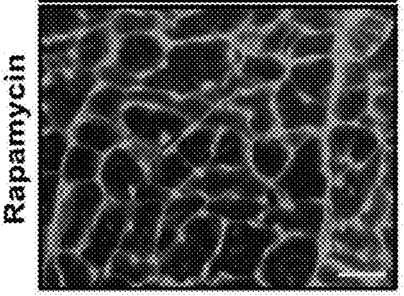
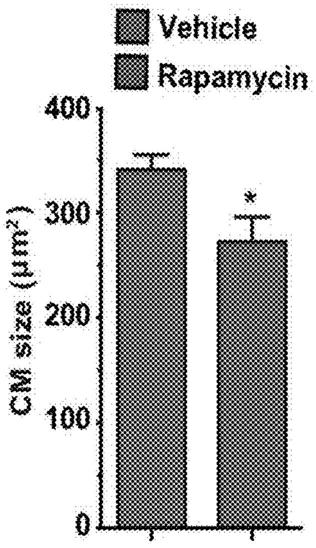
FIG. 26C
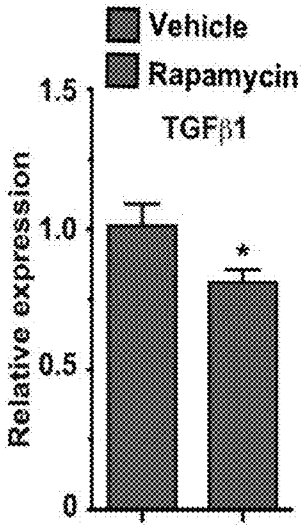
FIG. 27A
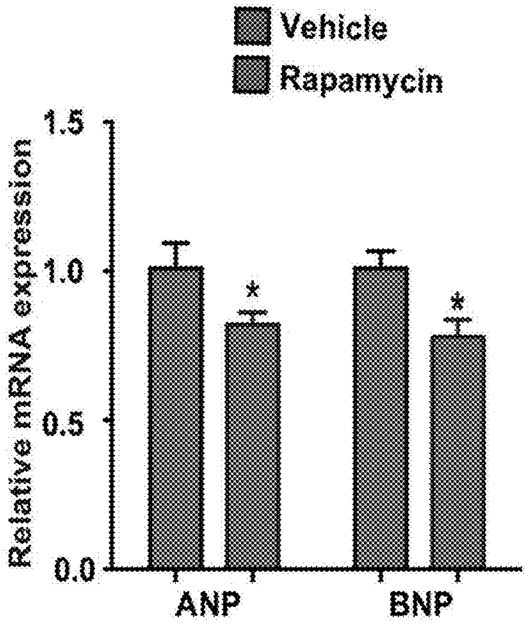
FIG. 27B

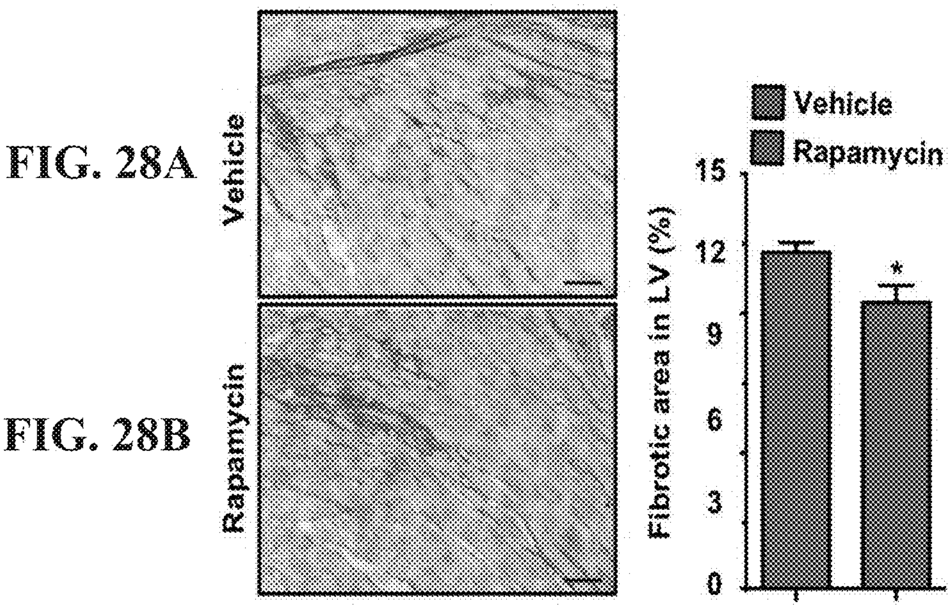
FIG. 28A
FIG. 28B
FIG. 28C
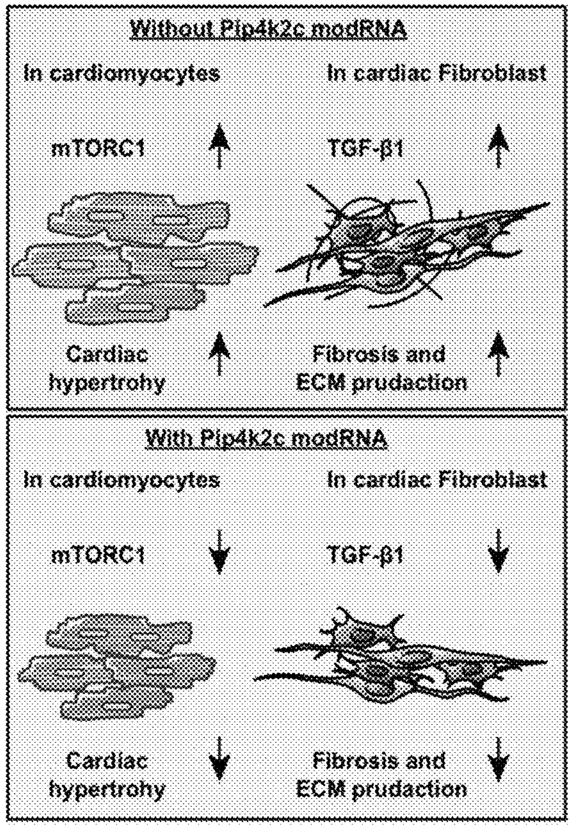
FIG. 29

FIG. 30A
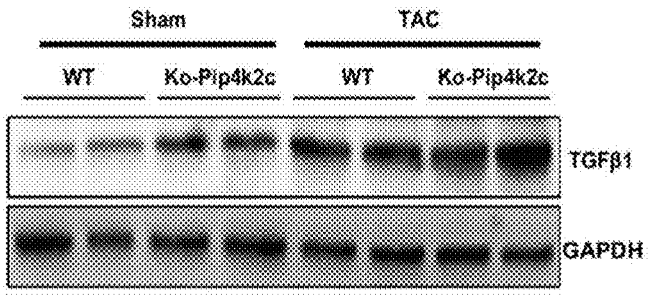
FIG. 30B
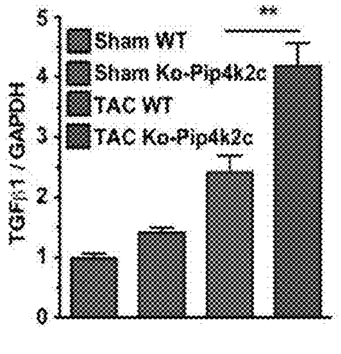
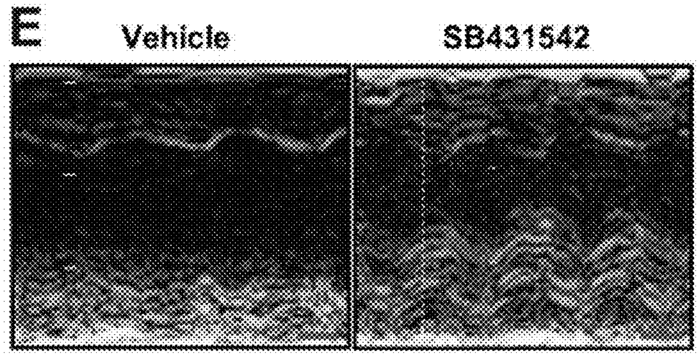
FIG. 30C FIG. 30D
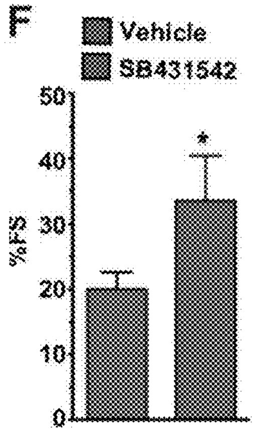
FIG. 30E
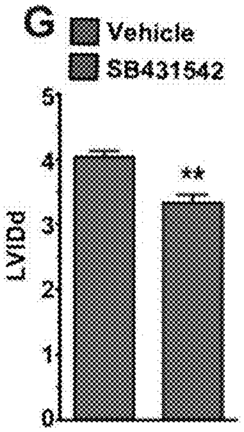
FIG. 30F

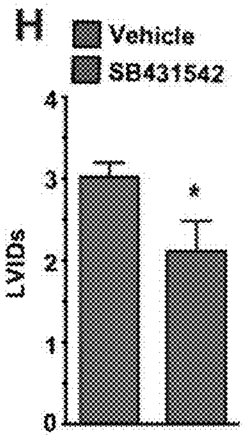
FIG. 30G
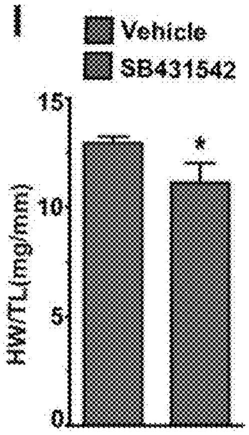
FIG. 30H
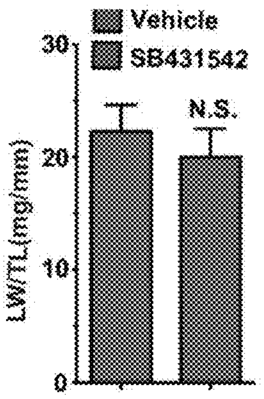
FIG. 30I
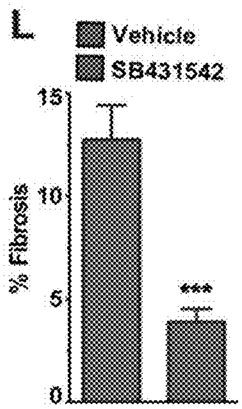
FIG. 30L
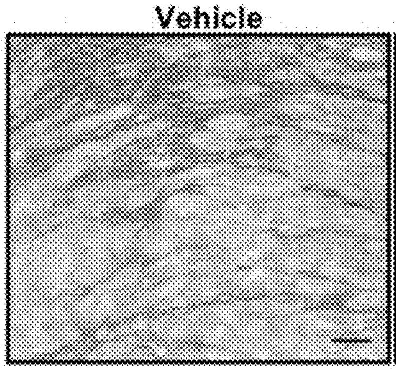
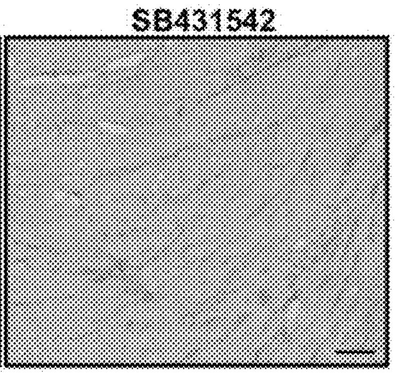
FIG. 30J FIG. 30K

GENE DELIVERY SYSTEMS FOR TREATMENT OF HEART FAILURE

CROSS REFERENCE TO RELATED APPLICATIONS

This application is a National Stage Filing under 35 U.S.C. § 371 or International Application No. PCT/US2020/059943, which was filed on Nov. 11, 2020, and claims the benefit of U.S. Provisional Application 62/933,681 filed Nov. 11, 2019, the disclosure of which applications are hereby incorporated by reference in their entireties.

FIELD OF THE INVENTION

The present disclosure generally relates to gene delivery systems and methods of use for the treatment and prevention of heart diseases including heart failure.

INCORPORATION BY REFERENCE OF SEQUENCE LISTING PROVIDED ELECTRONICALLY

An electronic version of the Sequence Listing is filed herewith, the contents of which are incorporated by reference in their entirety. The electronic file is 15.4 kilobytes in size, titled H2329025.txt, and was created on May 9, 2022.

BACKGROUND OF THE INVENTION

Heart disease encompasses heart failure, heart attack, and associated comorbidities. Heart failure (HF) diseases in particular are a major cause of morbidity and mortality worldwide. Heart failure, sometimes known as congestive heart failure, generally develops gradually overtime as the heart muscle becomes increasingly weaker. In some cases of heart failure, once the heart muscle becomes damaged and weakened, and the ventricles stretch (dilate) to the point that the heart cannot pump blood efficiently throughout the body. This is commonly the result of dilated cardiomyopathy (DCM)—a disease of the heart muscle, usually starting in the heart's main pumping chamber (left ventricle)—where heart muscle begins to dilate, meaning it stretches and becomes thinner. As the heart chambers dilate, the heart muscle no longer contracts normally and cannot pump blood very well. As the heart becomes increasing weaker heart failure can occur.

To date, the only treatment regimens for heart failure are to prevent further damage by controlling blood pressure, reducing the occurrence of arrhythmias, and preventing blood clots from forming. There no medications that reverse the weakened heart muscle. For those with severe DCM, the only treatments are invasive such as surgical repair of the left ventricle or implantation of biventricular pacemakers and cardioverter defibrillators. For subjects with advanced heart failure, such surgical interventions and be risky and it is unclear whether such surgical treatment always improves long-term outcomes. As such, there is a need for less invasive therapies that not only treat heart failure but can also improve cardiac muscle function.

SUMMARY OF THE INVENTION

The present disclosure is based, at least in part, on the development of superior compositions and methods of using those compositions to treat heart failure in general.

Accordingly, one aspect of the present disclosure provides a method of treating heart failure, the method encompassing administering a modified mRNA (modRNA) encoding for type 2 phosphatidylinositol-5-phosphate 4-kinase gamma (pip4k2c) to heart tissue of a subject in need thereof. In some instances, the gene expression of pip4k2c increases after administration of a modRNA encoding for pip4k2c to heart tissue of a subject in need thereof. In other instances, the gene expression of pip4k2c increases by at least 5-fold one day after administration of a modRNA encoding for pip4k2c to heart tissue of a subject in need thereof. In still other instances, the at least 5-fold increase in pip4k2c expression one day after administration of a modRNA encoding for pip4k2c is sustained for at least 8 days in heart tissue of a subject in need thereof.

Any of the methods for providing administration of a modRNA encoding for pip4k2c may inhibit the activity of mammalian target of rapamycin complex 1 (mTORC1), transforming growth factor beta (TGFβ), or a combination thereof after administration of a modRNA encoding for pip4k2c to heart tissue of a subject in need thereof. In some examples, mTORC1 and TGFβ are inhibited after administration of a modRNA encoding for pip4k2c to heart tissue of a subject in need thereof.

In some embodiments, methods of administering a modRNA encoding for pip4k2c to the heart tissue of a subject in need thereof increases life expectancy by at least 10% compared to an untreated subject with identical disease condition and predicted outcome. In other embodiments, methods of administering a modRNA encoding for pip4k2c to heart tissue of a subject in need thereof improves heart function by at least 10% compared to an untreated subject with identical disease condition and predicted outcome. In still other embodiments, methods of administering a modRNA encoding for pip4k2c to heart tissue of a subject in need thereof reduces cardiac fibrosis by at least 5% compared to an untreated subject with identical disease condition and predicted outcome. In other embodiments, methods of administering a modRNA encoding for pip4k2c to heart tissue of a subject in need thereof reverses cardiac hypertrophy by at least 10% compared to an untreated subject with identical disease condition and predicted outcome. In some examples, the heart failure treated by methods disclosed herein is dilated cardiomyopathy (DCM).

Another aspect of the present disclosure provided for a gene delivery system for treatment of heart failure encompassing a modified mRNA (modRNA) encoding for type 2 phosphatidylinositol-5-phosphate 4-kinase gamma (pip4k2c). In some examples, the gene delivery system for treatment of heart failure encompassing a modRNA encoding for pip4k2c can be locally administered to heart tissue. In other examples, the gene delivery system for treatment of heart failure encompassing a modRNA encoding for pip4k2c locally administered to heart tissue increases pip4k2c expression. In other examples, the gene delivery system for treatment of heart failure encompassing a modRNA encoding for pip4k2c locally administered to heart tissue inhibits mammalian target of rapamycin complex 1 (mTORC1), transforming growth factor beta (TGFβ), or a combination thereof in heart tissue.

Any of the gene delivery systems disclosed herein for treatment of heart failure providing for local administration of a modRNA encoding for pip4k2c can further encompass a delivery agent. In some examples, the gene delivery system can further encompass a delivery agent that targets heart tissue. In some other examples, the gene delivery system for treatment of heart failure providing for local administration of a modRNA encoding for pip4k2c can be formulated for intracardiac injection. In some examples, the heart failure treated by the gene delivery systems disclosed herein is dilated cardiomyopathy (DCM).

Yet another aspect of the present disclosure provides a method of treating heart failure, the method involving: a) preparing a modified mRNA (modRNA) encoding for type 2 phosphatidylinositol-5-phosphate 4-kinase gamma (pip4k2c), wherein the prepared modRNA does not elicit an immune response compared to exogenous RNA after local administration; and, b) locally administering the modRNA encoding for pip4k2c to heart tissue of a subject in need thereof, wherein the gene expression of pip4k2c increases after at least one administration. In some embodiments, the modRNA encoding for pip4k2c is locally administered to the heart tissue of a subject in need thereof at least once every 20 days. In other embodiments, life expectancy is increased by at least 40% 20 days after one local administration of the modRNA encoding for pip4k2c to the heart tissue of a subject in need thereof compared to an untreated subject with identical disease condition and predicted outcome. In some examples, the heart failure treated by the methods disclosed herein is dilated cardiomyopathy (DCM).

BRIEF DESCRIPTION OF THE FIGURES

The following drawings form part of the present specification and are included to further demonstrate certain aspects of the present disclosure, which can be better understood by reference to the drawing in combination with the detailed description of specific embodiments presented herein.

FIG. 1A depicts a schematic image representative of the non-failing normal heart samples, human hearts samples of cardiac hypertrophy, and human heart samples of dilated cardiomyopathy used for assessment of mRNA and protein expression of Pip4k2c. FIG. 1B shows a graph of mRNA expression of Pip4k2c in non-failing heart normal human heart (NF) samples, human hearts samples of cardiac hypertrophy (CH), and human heart samples of dilated cardiomyopathy (DCM) measured by qRT-PCT. One-way ANOVA, Tukey's Multiple Comparison Test was used to assess significance of results where n=4 for NF, n=2 for CH, n=3 for DCM and *=P<0.001, =P<0.01, *=P<0.05 and N.S=Not Significant. FIGS. 1C-1D show protein expression of Pip4k2c in non-failing normal human heart (NF) samples, human hearts samples of cardiac hypertrophy (CH), and human heart samples of dilated cardiomyopathy (DCM) measured by Western blot analysis. FIG. 1C: representative images of Western blot detection of Pip4k2c and loading control GAPDH. FIG. 1D: a graph depicting the ratio of Pip4k2c protein expression to GAPDH expression in the human heart samples. One-way ANOVA, Tukey's Multiple Comparison Test was used to assess significance of results where n=4 for NF, n=2 for CH, n=3 for DCM and *=P<0.001, =P<0.01, *=P<0.05 and N.S=Not Significant. FIGS. 1E-1K show images depicting the immunostaining of the left ventricle (LV) of non-failing normal human heart (NF) samples, human hearts samples of cardiac hypertrophy (CH), and human heart samples of dilated cardiomyopathy (DCM) where Pip4k2c expression is shown in red, α-Actinin, a cardiomyocyte marker, is shown in green, and DAPI, a nuclei marker, is shown in blue. White arrowheads point to non-CMs. Yellow arrowheads point to CMs. Scale bar=50 μm. FIG. 1E: Representative image of Pip4k2c expression in the LV of NF. FIG. 1F: Representative image of Pip4k2c, α-Actinin, and DAPI expression in the LV of NF. FIG. 1G: Representative image of Pip4k2c expression in the LV of CH. FIG. 111: Representative image of Pip4k2c, α-Actinin, and DAPI expression in the LV of CH. FIG. 11: Representative image of Pip4k2c expression in the LV of DCM. FIG. 1J: Representative image of Pip4k2c, α-Actinin, and DAPI expression in the LV of DCM. FIG. 1I shows a graph showing a quantitative analysis of Pip4k2c florescent intensity in immunostained LV sections of NF (n=3), CH (n=3), and DCM (n=3). One-way ANOVA, Tukey's Multiple Comparison Test was used to assess significance of results and *=P<0.001, =P<0.01, *=P<0.05 and N.S=Not Significant.

FIG. 2A depicts a schematic image representative of the timeline for assessing mRNA and protein expression of Pip4k2C in hearts from sham or TAC mouse models of heart failure. FIGS. 2B-2C show protein expression of Pip4k2c in hearts from sham or TAC mouse models of heart failure 4 days after sham and TAC surgery was competed measured by Western blot analysis. FIG. 2B: representative images of Western blot detection of Pip4k2c and loading control GAPDH. FIG. 2C: a graph depicting the ratio of Pip4k2c protein expression to GAPDH expression in the mouse heart samples. Unpaired two-tailed t-test was used to assess significance of results where n=2 for sham and n=2 for TAC and *=P<0.001, =P<0.01, *=P<0.05 and N.S=Not Significant. FIGS. 2D-2E show a graphs of mRNA expression of Pip4k2c in hearts or heart cells isolated from sham or TAC mouse models measured by qRT-PCT. FIG. 2D: a graph of mRNA expression of Pip4k2c in WT mouse heart samples in comparison with 4 days post-TAC injury. Unpaired two-tailed t-test was used to assess significance of results where n=4 for sham and n=4 for TAC. FIG. 2E: a graph of Pip4k2c mRNA expression in cardiomyoblasts (CMs) or cardio fibroblasts harvested from mice after 7 or 14 days post shame or TAC injury (n=3). Two-way ANOVA, Bonferroni post-hoc test was used to assess significance of results where n=3 for sham and n=3 for TAC and *=P<0.001, =P<0.01, *=P<0.05 and N.S=Not Significant. FIGS. 2F-2K show representative images of isolated, cultured neonatal mouse (P8) heart cells stained for Pip4k2c (red) in total heart cells (FIG. 2G), cardiomyocytes (FIG. 211), non-cardiomyocytes (FIG. 2I), endothelial cells (FIG. 2J), and smooth muscle cells (FIG. 2K) where α-Actinin (CM marker, green); Vimentin (non-CM marker, green); PECAM1 (endothelial cell marker, green); α-smooth muscle actin (smooth muscle cell marker, green); DAPI (nuclei marker, blue) and FIG. 2F shows total cells. Scale bar=10 μm.

FIG. 3A depicts a schematic of the experimental plan to evaluate using qRT-PCR Pip4k2c expression in P3 rat neonatal CMs treated with phenylephrine (PE) or DMSO, in vitro.

FIG. 3B shows a graph depicting quantification of mRNA expression of Pip4k2c in P3 rat neonatal CMs treated with phenylephrine (PE) or DMSO, in vitro using qRT-PCR. Unpaired two-tailed t-test was used to assess significance of results where n=3 for DMSO and n=3 for PE and ***=P<0.001. The order of groups as indicated from top to bottom in the figure legend is the same as the order of the groups as depicted in the bar graph from left to right.

FIG. 3C depicts a schematic of the experimental plan to evaluate Pip4k2c expression by immunostaining in isolated cultured mouse neonatal (P8) heart cells.

FIGS. 3D-3H show images depicting the immunostaining of isolated cultured mouse neonatal (P8) heart cells where cells were stained for Pip4k2c (red), α-actinin (CMs marker, silver), vimentin (fibroblast marker, green) and DAPI (nuclei marker) in blue. Scale bar=25 μm. FIG. 3D: representative image of Pip4k2c expression in isolated cultured mouse neonatal (P8) heart cells. FIG. 3E: representative image of DAPI staining in isolated cultured mouse neonatal (P8) heart cells. FIG. 3F: representative image of vimentin expression in isolated cultured mouse neonatal (P8) heart cells. FIG. 3G: representative image of α-Actinin expression in isolated cultured mouse neonatal (P8) heart cells. FIG. 311: representative image of Pip4k2c, α-Actinin, vimentin, and DAPI expression in isolated cultured mouse neonatal (P8) heart cells. White arrowheads point to non-CMs. Yellow arrowheads point to CMs.

FIG. 4A: a representative image of a pip4k2c$^{+/+}$ littermate control (WT) mouse at E18. Actual size. FIG. 4B: a representative image of a pip4k2c$^{-/-}$ (KO-Pip4k2c) mouse at E18. Actual size. FIG. 4C: a representative image of a whole heart from a WT mouse at E18. Scale bar=1 mm. FIG. 4D: a representative image of a whole heart from a KO-Pip4k2c mouse at E18. Scale bar=1 mm.

FIG. 4E: shows a graph of the body weight of E18 WT mice (n=5) and E18 KO-Pip4k2c mice (n=5). FIG. 4F: shows a graph of the whole heart weight to body weight ratio of E18 WT mice (n=5) and E18 KO-Pip4k2c mice (n=5). FIG. 4G: shows a graph of the number of isolated cardiomyocytes (CM) from the hearts (n=3) from E18 WT and E18 KO-Pip4k2c mice. The order of groups as indicated from top to bottom in the figure legend is the same as the order of the groups as depicted in the bar graph from left to right.

FIGS. 5A-5D show images depicting echocardiography (ECHO) images (Scale bar=1 mm) of the left ventricle of: a pip4k2c$^{+/+}$ littermate control (WT) mouse 21 days post Sham injury (FIG. 5A); a pip4k2c$^{-/-}$ (KO-Pip4k2c) mouse 21 days post Sham injury (FIG. 5B); a WT mouse 21 days post TAC injury (FIG. 5C); and, a KO-Pip4k2c mouse 21 days post TAC injury (FIG. 5D).

FIGS. 5E-5H show graphs depicting ECHO evaluation of fractioning shorting (FIG. 5E), LVIDd (FIG. 5F), LVIDs (FIG. 5G), and delta % left ventricular ejection fraction (FIG. 511) in the left ventricle of: a pip4k2c$^{+/+}$ littermate control (WT) mouse 21 days post Sham injury (Sham WT); a pip4k2c$^{-/-}$ (KO-Pip4k2c) mouse 21 days post Sham injury (Sham KO-Pip4k2c); a WT mouse 21 days post TAC injury (TAC WT); and, a KO-Pip4k2c mouse 21 days post TAC injury (TAC KO-Pip4k2c). One-way ANOVA, Bonferroni post-hoc test was used to measure significance where n=8 for all four experimental groups and *=P<0.001, =P<0.01, *=P<0.05, and N.S=Not Significant. The order of groups as indicated from top to bottom in the figure legend is the same as the order of the groups as depicted in the bar graph from left to right.

FIGS. 6A-6I show heart morphology of a pip4k2c$^{+/+}$ littermate control (WT) mice and pip4k2c$^{-/-}$ (KO-Pip4k2c) mice 21 days post Sham injury or TAC injury. FIG. 6A: a graph depicting quantification of heart weight to tubia length in pip4k2c$^{+/+}$ littermate control (WT) mice 21 days post Sham injury (Sham WT); pip4k2c$^{-/-}$ (KO-Pip4k2c) mice 21 days post Sham injury (Sham KO-Pip4k2c); WT mice 21 days post TAC injury (TAC WT); and, KO-Pip4k2c mice 21 days post TAC injury (TAC KO-Pip4k2c). One-way ANOVA, Bonferroni post-hoc test was used to measure significance where n=8 for all four experimental groups and *=P<0.001, =P<0.01, *=P<0.05, and N.S=Not Significant. The order of groups as indicated from top to bottom in the figure legend is the same as the order of the groups as depicted in the bar graph from left to right. FIG. 6B: representative image of whole heart of WT mouse 21 days post Sham surgery. Scale bar=1 mm. FIG. 6C: representative image of whole heart of KO-Pip4k2c mouse 21 days post Sham surgery. Scale bar=1 mm. FIG. 6D: representative image of whole heart of WT mouse 21 days post TAC surgery. Scale bar=1 mm. FIG. 6E: representative image of whole heart of KO-Pip4k2c mouse 21 days post TAC surgery. Scale bar=1 mm. FIG. 6F: representative image of H&E staining of heart section from WT mouse 21 days post Sham surgery. Scale bar=1 mm. FIG. 6G: representative image of H&E staining of heart section from KO-Pip4k2c mouse 21 days post Sham surgery. Scale bar=1 mm. FIG. 611: representative image of H&E staining of heart section from WT mouse 21 days post TAC surgery. Scale bar=1 mm. FIG. 61: representative image of H&E staining of heart section from KO-Pip4k2c mouse 21 days post TAC surgery. Scale bar=1 mm.

FIGS. 7A-7E show images of wheat germ agglutinin (WGA) staining of heart sections from pip4k2c$^{+/+}$ littermate control (WT) mice and pip4k2c$^{-/-}$ (KO-Pip4k2c) mice to evaluate CM size (cross-sectional area) after 21 days post Sham or TAC injury. FIG. 7A: representative image of WGA staining of heart section from WT mouse 21 days post Sham surgery. Scale bar=50 μm. FIG. 7B: representative image of WGA staining of heart section from KO-Pip4k2c mouse 21 days post Sham surgery. Scale bar=50 μm. FIG. 7C: representative image of WGA staining of heart section from WT mouse 21 days post TAC surgery. Scale bar=50 μm. FIG. 7D: representative image of WGA staining of heart section from KO-Pip4k2c mouse 21 days post TAC surgery. Scale bar=50 μm. FIG. 7E: a graph depicting quantification of CM size (cross-sectional area) in pip4k2c$^{+/+}$ littermate control (WT) mice 21 days post Sham injury (Sham WT); pip4k2c$^{-/-}$ (KO-Pip4k2c) mice 21 days post Sham injury (Sham KO-Pip4k2c); WT mice 21 days post TAC injury (TAC WT); and, KO-Pip4k2c mice 21 days post TAC injury (TAC KO-Pip4k2c). The order of groups as indicated from top to bottom in the figure legend is the same as the order of the groups as depicted in the bar graph from left to right. One-way ANOVA, Bonferroni post-hoc test was used to measure significance where n=8 for all four experimental groups and *=P<0.001, =P<0.01, *=P<0.05, and N.S=Not Significant.

FIG. 8A: a graph depicting mRNA expression of the hypertrophic marker ANP in the hearts of pip4k2c$^{+/+}$ littermate control (WT) mice 21 days post Sham injury (Sham WT); pip4k2c$^{-/-}$ (KO-Pip4k2c) mice 21 days post Sham injury (Sham KO-Pip4k2c); WT mice 21 days post TAC injury (TAC WT); and, KO-Pip4k2c mice 21 days post TAC injury (TAC KO-Pip4k2c). One-way ANOVA, Bonferroni post-hoc test was used to measure significance where n=5 for all four experimental groups and *=P<0.001, =P<0.01, *=P<0.05, and N.S=Not Significant. The order of groups as indicated from top to bottom in the figure legend is the same as the order of the groups as depicted in the bar graph from left to right. FIG. 8B: a graph depicting mRNA expression of the hypertrophic marker BNP in the hearts Sham WT, Sham KO-Pip4k2c, TAC WT, and TAC KO-Pip4k2c mice. One-way ANOVA, Bonferroni post-hoc test was used to measure significance where n=5 for all four experimental groups and *=P<0.001, =P<0.01, *=P<0.05, and N.S=Not Significant. The order of groups as indicated from top to bottom in the figure legend is the same as the order of the groups as depicted in the bar graph from left to right. FIG. 8C: a graph depicting mRNA expression of matrix the metalloproteases (MMPs) genes MMP2, MMP3, MMP7 and MMP9 in the hearts Sham WT, Sham KO-Pip4k2c, TAC WT, and TAC KO-Pip4k2c mice. Unpaired two-tailed t-test was used to measure significance where n=5 for all four experimental groups and *=P<0.001, =P<0.01, *=P<0.05, and N.S=Not Significant. FIG. 8D: a graph depicting mRNA expression of TGFβ1 and its downstream target genes Col1a1, Col1a2, Col3a1, and FN1 in the hearts Sham WT, Sham KO-Pip4k2c, TAC WT, and TAC KO-Pip4k2c mice. One-way ANOVA, Bonferroni post-hoc test was used to measure significance where n=5 for all four experimental groups and *=P<0.001, =P<0.01, *=P<0.05, and N.S=Not Significant. The order of groups as indicated from top to bottom in the figure legend is the same as the order of the groups as depicted in the bar graph from left to right. FIG. 8E: a graph depicting qPCR analysis of Pip4a2a and Pip4k2b expression 21 days post TAC injury in WT or KO-Pip4k2c (n=5). Unpaired two-tailed t-test for b. N.S., Not Significant.

FIGS. 9A-9J show images depicting sirius red/fast green staining of isolated heart sections to evaluate fibrotic area of in the hearts of pip4k2c$^{+/+}$ littermate control (WT) mice 21 days post Sham injury (Sham WT); pip4k2c$^{-/-}$ (KO-Pip4k2c) mice 21 days post Sham injury (Sham KO-Pip4k2c); WT mice 21 days post TAC injury (TAC WT); and, KO-Pip4k2c mice 21 days post TAC injury (TAC KO-Pip4k2c). FIG. 9A: shows a representative image of sirius red/fast green staining of a heart section from a WT mouse 21 days post Sham injury. Scale bar=50 μm. FIG. 9B: shows a representative image of sirius red/fast green staining of a heart section from a KO-Pip4k2c mouse 21 days post Sham injury. Scale bar=50 km. FIG. 9C: shows a representative image of sirius red/fast green staining of a heart section from a WT mouse 21 days post TAC injury. Scale bar=50 km. FIG. 9D: shows a representative image of sirius red/fast green staining of a heart section from a KO-Pip4k2c mouse 21 days post TAC injury. Scale bar=50 μm. FIG. 9E: a graph depicting quantification of fibrotic area of hearts from Sham WT, Sham KO-Pip4k2c, TAC WT, and TAC KO-Pip4k2c mice. One-way ANOVA, Bonferroni post-hoc test was used to measure significance where n=8 for all four experimental groups and *=P<0.001, =P<0.01, *=P<0.05, and N.S=Not Significant. The order of groups as indicated from top to bottom in the figure legend is the same as the order of the groups as depicted in the bar graph from left to right. FIGS. 9F-9J show representative images of Sirius red/fast green indicating fibrotic area 21 days post Sham injury in wild-type mice (FIG. 9F), and KO-Pip4k2c mice (FIG. 9I) and TAC injury in wild-type mice (FIG. 9G), and KO-Pip4k2c mice (FIG. 9J) where FIG. 9H shows an enlarged image of the fibrosis in a Sham-injured KO-Pip4k2c mouse and FIG. 9K shows an enlarged image of the fibrosis in a TAC-injured KO-Pip4k2c. and KO-Pip4k2c mouse.

FIG. 10 shows a graph depicting the survival curve of mice of pip4k2c$^{+/+}$ littermate control (WT) mice and pip4k2c$^{-/-}$ (KO-Pip4k2c) mice over 21 days post Sham injury or TAC injury. Mantel-Cox log-rank test was used to measure significance where n=10 for all four experimental groups and *=P<0.001, =P<0.01, *=P<0.05, and N.S=Not Significant.

FIG. 11A: shows an isolated CM from the heart of a WT TAC mouse stained with the CM sarcomeric structural protein α-Actinin and DAPI (a nuclei marker). Scale bar=20 μm. FIG. 11B: shows an isolated CM from the heart of a KO-Pip4k2c TAC mouse stained with the CM sarcomeric structural protein α-Actinin and DAPI. Scale bar=20 μm. FIG. 11C: shows an isolated CM from the heart of a WT TAC mouse stained with the CM sarcomeric structural protein Troponin T and DAPI. Scale bar=20 μm. FIG. 11D: shows an isolated CM from the heart of a KO-Pip4k2c TAC mouse stained with the CM sarcomeric structural protein Troponin T and DAPI. Scale bar=20 μm.

FIG. 11E: shows an isolated CM from the heart of a WT TAC mouse and immunostained with DAPI (a nuclei marker) and WGA to evaluate CM size. Scale bar=20 am. FIG. 11F: shows an isolated CM from the heart of a KO-Pip4k2c TAC mouse and immunostained with DAPI (and WGA to evaluate CM size. Scale bar=20 μm. FIG. 11G: a graph depicting quantification of CM size of isolated cardiomyocytes from WT TAC, and KO-Pip4k2c TAC mice. Unpaired two-tailed t-test was used to measure significance where n=3 for all experimental groups and **=P<0.01.

FIG. 13A: Western blot of Luc (control) or Pip4k2c modRNA expression in mouse heart 24 hours post TAC. FIG. 13B: Quantitative analysis of FIG. 13A. Unpaired two-tailed t-test was used to measure significance where n=2 for all experimental groups and =P<0.01. The order of groups as indicated from top to bottom in the figure legend is the same as the order of the groups as depicted in the bar graph from left to right. FIG. 13C: Western blot of Luc (control) or Pip4k2c modRNA expression in mouse heart 0 hours, 12 hours, 1 day, 2 days, 4 days, 7 days, 10 days, and 21 days post TAC. FIG. 13D: Quantitative analysis of FIG. 13C. One-way ANOVA, Tukey's Multiple Comparison Test was used to measure significance where n=2 for all experimental groups and *=P<0.001, **=P<0.01, *=P<0.05, and N.S, Not Significant.

FIGS. 14A-14B show representative echocardiography images of the left ventricle of wild type (WT) mice 21 days post TAC injury and delivery of luciferase (Luc) modRNA (FIG. 14A) or Pip4k2c modRNA (FIG. 14B). Scale bar=1 mm. FIGS. 14C-14E show graphs assessing the ECHO evaluation of fractioning shorting (FIG. 14C), LVIDd (FIG. 14D) or LVIDd (FIG. 14E) 21 days post TAC injury and delivery of luciferase (Luc) modRNA or Pip4k2c modRNA to mouse heart. Unpaired two-tailed t-test was used to measure significance where n=8 for all experimental groups and *=P<0.001, =P<0.01, *=P<0.05, and N.S, Not Significant. The order of groups as indicated from top to bottom in the figure legend is the same as the order of the groups as depicted in the bar graph from left to right. FIGS. 14F-14K show graphs assessing the fractioning shorting (FIG. 14F), LVIDd (FIG. 14G), LVIDs (FIG. 14H) and Echo evaluation of delta % left ventricular ejection fraction (FIG. 14I), LVPWd (FIG. 14J) and LVPWs (FIG. 14K) before (day 0), 14, or 21 days post TAC injury and delivery of Luc or Pip4k2c modRNA (n=8).

FIGS. 15A-15C depict images of total mouse heart weight analysis. FIG. 15A: representative image of whole heart 21 days post TAC injury and delivery of luciferase (Luc) modRNA. Scale bar=50 μm. FIG. 15B: representative image of whole heart 21 days post TAC injury and delivery of Pip4k2c modRNA. Scale bar=50 μm. FIG. 15C: quantitative analysis of FIGS. 15A-15B. Unpaired two-tailed t-test was used to measure significance where n=8 for all experimental groups and *=P<0.001, =P<0.01, *=P<0.05, and N.S, Not Significant.

FIGS. 16A-16C depict images of WGA staining to evaluate CM size (cross-sectional area) in mouse heart. FIG. 16A: representative image of WGA staining of heart tissue 21 days post TAC injury and delivery of luciferase (Luc) modRNA. Scale bar=100 μm. FIG. 16B: representative image of WGA staining of heart tissue 21 days post TAC injury and delivery of Pip4k2c modRNA. Scale bar=100 μm. FIG. 16C: quantitative analysis of FIGS. 16A-16B. Unpaired two-tailed t-test was used to measure significance where n=8 for all experimental groups and *=P<0.001, =P<0.01, *=P<0.05, and N.S, Not Significant.

FIG. 17A: a graph depicting mRNA expression of the hypertrophic markers ANP and BNP in the hearts of mice 21 days post TAC injury and delivery of luciferase (Luc) modRNA or Pip4k2c modRNA. FIG. 17B: a graph depicting mRNA expression of depicting mRNA expression of TGFβ1 and its downstream target genes Col1a1, Col1a2, Col3a1, and FN1 in the hearts of mice 21 days post TAC injury and delivery of Luc modRNA or Pip4k2c modRNA. FIG. 17C: a graph depicting mRNA expression of depicting mRNA expression of matrix the metalloproteases (MMPs) genes MMP2, MMP3, MMP7 and MMP9 and in the hearts of mice 21 days post TAC injury and delivery of luciferase (Luc) modRNA or Pip4k2c modRNA.

FIGS. 18A-18C depict images of sirius red/fast green staining to evaluate fibrotic area in mouse heart. FIG. 18A: representative image of sirius red/fast green staining of heart tissue 21 days post TAC injury and delivery of luciferase (Luc) modRNA. Scale bar=100 μm. FIG. 18B: representative image of sirius red/fast green staining of heart tissue 21 days post TAC injury and delivery of Pip4k2c modRNA. Scale bar=100 μm. FIG. 18C: quantitative analysis of FIGS. 18A-18B. Unpaired two-tailed t-test was used to measure significance where n=8 for all experimental groups and *=P<0.001, =P<0.01, *=P<0.05, and N.S, Not Significant.

FIG. 19 shows a graph depicting the survival curve of mice 21 days post TAC injury and delivery of luciferase (Luc) modRNA or Pip4k2c modRNA. Mantel-Cox log-rank test was used to measure significance where n=10 for all four experimental groups and *=P<0.001, =P<0.01, *=P<0.05, and N.S=Not Significant.

FIGS. 20A-20J show images of an evaluation of cardiac fibroblast proliferation using cardiac fibroblasts isolated from the hearts of pip4k2c$^{+/+}$ littermate control (WT) and pip4k2c$^{-/-}$ (KO-Pip4k2c) 21 days post TAC injury. FIG. 20A: representative bright field image of cardiac fibroblasts isolated from a WT heart 21 days post TAC injury followed by a 5 day treatment with PBS (control). Scale bar=50 μm. FIG. 20B: representative bright field image of cardiac fibroblasts isolated from a KO-Pip4k2c heart 21 days post TAC injury followed by a 5 day treatment with PBS (control). Scale bar=50 μm. FIG. 20C: representative bright field image of cardiac fibroblasts isolated from a KO-Pip4k2c heart 21 days post TAC injury followed by a 5 day treatment with TGF-β inhibitor (SB431542). Scale bar=50 μm. FIG. 20D: representative bright field image of cardiac fibroblasts isolated from a KO-Pip4k2c heart 21 days post TAC injury followed by a 5 day treatment with Pip4k2c modRNA. Scale bar=50 μm. FIG. 20E: representative image of cardiac fibroblasts isolated from a WT heart 21 days post TAC injury followed by a 5 day treatment with PBS (control) immunostained for pH3 (a mitosis marker, red), fibroblast marker Vimentin (green), and DAPI, (nuclei, blue). Scale bar=50 km. FIG. 20F: representative image of cardiac fibroblasts isolated from a KO-Pip4k2c heart 21 days post TAC injury followed by a 5 day treatment with PBS (control) immunostained for pH3 (a mitosis marker, red), fibroblast marker Vimentin (green), and DAPI, (nuclei, blue). Scale bar=50 km. FIG. 20G: representative image of cardiac fibroblasts isolated from a KO-Pip4k2c heart 21 days post TAC injury followed by a 5 day treatment with TGF-3 inhibitor (SB431542) immunostained for pH3 (a mitosis marker, red), fibroblast marker Vimentin (green), and DAPI, (nuclei, blue). Scale bar=50 km. FIG. 20H: representative image of cardiac fibroblasts isolated from a KO-Pip4k2c heart 21 days post TAC injury followed by a 5 day treatment with Pip4k2c modRNA immunostained for pH3 (a mitosis marker, red), fibroblast marker Vimentin (green), and DAPI, (nuclei, blue). Scale bar=50 km. FIG. 201: a graph of the cell number in each experimental group depicted in FIGS. 20A-20D. One-way ANOVA was used to measure significance where n=3 for all experimental groups and *=P<0.001, =P<0.01, *=P<0.05, and N.S=Not Significant. FIG. 20J: a graph of the pH3 positive cardiac fibroblast in each experimental group depicted in FIGS. 20E-20H. One-way ANOVA was used to measure significance where n=3 for all experimental groups and *=P<0.001, =P<0.01, *=P<0.05, and N.S=Not Significant.

FIG. 21A: graph depicting Colla gene expression in all four experimental treatment groups. FIG. 21B: graph depicting Col2a gene expression in all four experimental treatment groups. FIG. 21C: graph depicting Col3a1 gene expression in all four experimental treatment groups. FIG. 21D: graph depicting FN1 gene expression in all four experimental treatment groups. FIG. 21E: graph depicting CTGF gene expression in all four experimental treatment groups.

FIG. 22A: representative image of Western blots probed for phospho-p70s6k protein expression, total p70s6k protein expression, and GAPDH (loading control) protein expression. FIG. 22B: quantitative analysis of FIG. 22A. One-way ANOVA, Tukey's Multiple Comparison Test was used to measure significance where n=8 for all experimental groups and *=P<0.001, =P<0.01, *=P<0.05, and N.S, Not Significant.

FIG. 25A: representative image of whole heart 21 days post TAC injury and delivery of vehicle or rapamycin to KO-Pip4k2c mouse heart. Scale bar=50 μm. FIG. 25B: quantitative analysis of KO-Pip4k2c mouse heart weight to tibia length 21 days post TAC injury and delivery of vehicle or rapamycin. Unpaired two-tailed t-test was used to measure significance where n=4 for all experimental groups and *=P<0.001, =P<0.01, *=P<0.05, and N.S, Not Significant. FIG. 25C: quantitative analysis of KO-Pip4k2c mouse lung weight to tibia length 21 days post TAC injury and delivery of vehicle or rapamycin. Unpaired two-tailed t-test was used to measure significance where n=4 for all experimental groups and *=P<0.001, =P<0.01, *=P<0.05, and N.S, Not Significant.

FIGS. 26A-26C depict images of WGA staining to evaluate CM size (cross-sectional area) in KO-Pip4k2c mouse heart. FIG. 26A: representative image of WGA staining of KO-Pip4k2c heart tissue 21 days post TAC injury and delivery of vehicle. Scale bar=100 μm. FIG. 26B: representative image of WGA staining of KO-Pip4k2c heart tissue 21 days post TAC injury and delivery of rapamycin. Scale bar=100 μm. FIG. 26C: quantitative analysis of FIGS. 26A-26B. Unpaired two-tailed t-test was used to measure significance where n=4 for all experimental groups and *=P<0.001, =P<0.01, *=P<0.05, and N.S, Not Significant.

FIGS. 27A and 27B show a graphs depicting quantification of mRNA expression of TGFβ1 (FIG. 27A) and ANP and BNP (FIG. 27B) in KO-Pip4k2c heart tissue 21 days post TAC injury and delivery of vehicle or rapamycin. Unpaired two-tailed t-test was used to measure significance where n=4 for all experimental groups and *=P<0.001, =P<0.01, *=P<0.05, and N.S, Not Significant.

FIGS. 28A-28C depict images of sirius red/fast green staining to evaluate fibrotic area in KO-Pip4k2c mouse heart. FIG. 28A: representative image of sirius red/fast green staining of KO-Pip4k2c heart tissue 21 days post TAC injury and delivery of vehicle. Scale bar=100 μm. FIG. 28B: representative image of sirius red/fast green staining of KO-Pip4k2c heart tissue 21 days post TAC injury and delivery of rapamycin. Scale bar=100 μm. FIG. 28C: quantitative analysis of FIGS. 28A-28B. Unpaired two-tailed t-test was used to measure significance where n=4 for all experimental groups and *=P<0.001, =P<0.01, *=P<0.05, and N.S, Not Significant.

FIG. 29 depicts a schematic of a model for pip4k2c modRNA regulation in cardiac hypertrophy and cardiac failure via inhibition of mTORC1 and TGFβ1 post TAC injury.

FIGS. 30A-30K depict images showing Pip4k2c attenuation of cardiac fibrosis via the TGFβ1 pathway. FIG. 30A shows an image of a Western blot analysis of TGFβ protein expression in WT or KO-Pip4k2c 21 days post sham or TAC injury. FIG. 30B shows a graph of the quantitative analysis of the Western blot in FIG. 30A (n=2). FIGS. 30C-30D show representative images of echocardiography image of left ventricle 21 days post TAC injury in the presence of vehicle (FIG. 30C) or SB4311542 (FIG. 30D). Scale bar=1 mm. FIGS. 30E-30G show graphs depicting echo evaluation of fractioning shorting (FIG. 30E), LVIDd (FIG. 30F), or LVIDd (FIG. 30G) 21 days post TAC injury and delivery of vehicle or SB4311542 (n=3). FIG. 30H shows a graph depicting heart weight to tibia length 21 days post TAC injury and delivery of vehicle or SB4311542 (n=3). FIG. 301 shows a graph depicting lung weight to tibia length 21 days post TAC injury and delivery of vehicle or SB4311542 (n=3). FIGS. 30J-30K show representative images of Sirius red/fast green to evaluate fibrotic area 21 days post TAC injury in the presence of vehicle (FIG. 30J) or SB4311542 (FIG. 30K). Scale bar=50 μm. FIG. 30L is a graph showing the quantitative analysis of the images in FIGS. 30J-30K (n=3). Statistics for all graphs show reflect one-way ANOVA, Tukey's Multiple Comparison Test were or an unpaired two-tailed t-test were *=P<0.05, N.S.=Not Significant.

FIG. 32A shows a representative image of a transfected cross-sectioned heart (short axis view; transfected cells are green, and non-transfected cells are red) in Rosa26mTmG mouse 24 hours after 100 μg Cre modRNA was injected directly into the myocardium. Scale bar=1 mm. FIG. 32B is a graph showing the quantification of Cre modRNA biodistribution in the LV post transfection in vivo. n=3. Two-tailed Student's t-tests (B). ****, P<0.0001.

FIG. 33A is a schematic showing the modRNA structures of Pip4k2c and mutant Pip4k2c constructs. FIGS. 33L-33N are graphs showing a quantitative analysis for total collagen (FIG. 33L), change in cardia fibroblast number (FIG. 33M), and percent expression of pH3 (a cell division marker) (FIG. 33N) in cardiac fibroblasts isolated and sorted (for the fibroblastic marker CD90) from WT or KO-Pip4k2c hearts 21 days post TAC injury and treated with DMSO (control), TbetaR1/ALK5 inhibitor (SB431542), Pip4k2c or mutant Pip4k2c modRNA. Cell numbers and pH3 (cell division marker) were calculated 5 days later. (n=3); One-way ANOVA, **, P<0.0001, *, P<0.001, **, P<0.01, N.S., Not Significant.

DETAILED DESCRIPTION OF THE INVENTION

Figure 1A:
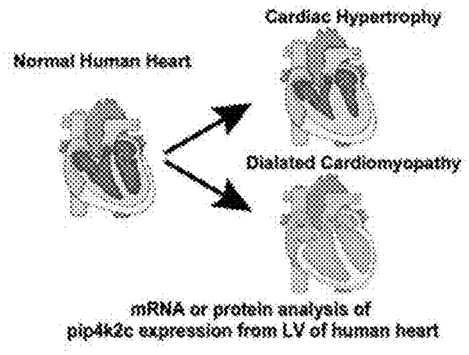
FIGS. 1A-1K include images showing decreased Pip4k2c expression in failing hearts of humans.
Figure 1B:
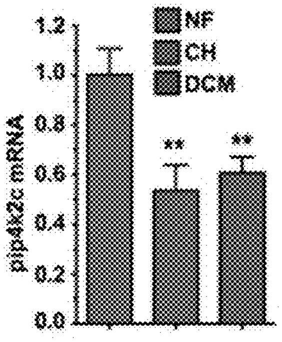

Some aspects of the present disclosure include compositions encompassing a gene delivery system for treatment of heart failure. In general, compositions disclosed herein may encompass at least one modRNA encoding for the modulated gene expression of at least one cardiac gene. As used herein, the term "modRNA" refers to a synthetic modified RNA that can be used for expression of a gene of interest. Also as used herein, the term "modulated gene expression" refers to over-expression of at least one gene native to a cardiac cell, under-expression of at least one gene native to a cardiac cell, knockout of at least one gene native to a cardiac cell, or a combination thereof. As used herein, the term "native" or "native cell" refers to the state of a cell in the context of a multicellular organism or in a natural environment. In some embodiments, compositions disclosed herein may encompass at least one modRNA encoding for the modulated gene expression of pip4k2c. As used herein, the term "pip4k2c" refers to a gene coding for the protein phosphatidylinositol-5-phosphate 4-kinase type 2 gamma (PI5P4Kγ).

Some other aspects of the present disclosure include methods of treating heart failure. In general, methods disclosed herein may treating heart failure with administration of a gene delivery system encompassing at least one modRNA encoding for the modulated gene expression of at least one cardiac gene. In some embodiments, methods disclosed herein may treat heart failure by administering a modRNA encoding for pip4k2c to heart tissue of a subject in need thereof.

(I) Compositions

Aspects of the present disclosure include compositions encompassing at least modRNA encoding for modulating gene expression. Compositions disclosed herein may encompass at least modRNA encoding for modulating gene expression wherein modulation of gene expression can be a result of treatment with a modRNA disclosed herein. Compositions disclosed herein may encompass at least modRNA encoding for modulating gene expression wherein modulation of gene expression can increase life expectancy.

(a) modRNA

In various embodiments, compositions disclosed herein can encompass at least one modRNA encoding for modulating gene expression. Methods of synthesizing modRNA suitable of use in compositions disclosed herein are described in Kondrat et al., In: Ishikawa K. (eds) Cardiac Gene Therapy. Methods in Molecular Biology, vol 1521. Humana Press, New York, NY (2017); Hadas et al., Mol Ther Methods Clin Dev. (2019) 14: 300-305; *Sultana* et al., Mol Ther. (2017) 25(6): 1306-1315; and Svitkin et al., Nucleic Acids Res. (2017) 45(10): 6023-6036, the disclosures of which are incorporated herein in their entirety. In some embodiments, synthesis of modRNA for in vivo use can encompasses 4 steps: (1) DNA template creation containing the desired transcript; (2) in vitro transcription (IVT); (3) 5' phosphate removal with Antarctic phosphatase; and (4) precipitation with 5 M ammonium acetate salt.

In some embodiments, a modRNA can encompass an exogenous RNA sequence with at least nucleoside substitution. In some aspects, a modRNA can encompass an exogenous RNA sequence with at least nucleoside substitution that changes mRNA secondary structure compared to exogenous mRNA structure. In other aspects, a modRNA can encompass an exogenous RNA sequence with at least nucleoside substitution that prevents innate immune system recognition compared to exogenous mRNA structure. In still other aspects, a modRNA can encompass an exogenous RNA sequence with at least nucleoside substitution that attenuates innate immune system recognition by about 50% to about 100%, about 55%, to about 95%, or about 60% to about 90% compared to exogenous mRNA structure. In other aspects, a modRNA can encompass an exogenous RNA sequence with at least nucleoside substitution that prevents RNase degradation compared to exogenous mRNA structure. In still other aspects, a modRNA can encompass an exogenous RNA sequence with at least nucleoside substitution that attenuates RNase degradation by about 50% to about 100%, about 55%, to about 95%, or about 60% to about 90% compared to exogenous mRNA structure.

In some aspects, modRNA can encompass an exogenous RNA sequence with at least uridine substituted with pseudouridine. In other aspects, modRNA can encompass an exogenous RNA sequence with at least cytidine substituted with 5-methylcytidine. In some other aspects, modRNA can encompass an exogenous RNA sequence including the modified nucleoside 5-methylcytidine (5mC). In still some other aspects, modRNA can encompass an exogenous RNA sequence including the modified nucleoside 2-Thiouridine-5'-Triphosphate (2-thio ψU). In yet other aspects, modRNA can encompass an exogenous RNA sequence including the modified nucleoside1-Methylpseudouridine-5'-Triphosphate (1-mψU). In other aspects, modRNA can encompass an exogenous RNA sequence including the modified nucleoside N1-methyl-pseudouridine (N1mΨ). In other aspects, modRNA can encompass an exogenous RNA wherein the 5' triphosphates are removed. In still other aspects, modRNA can encompass an exogenous RNA wherein a 3'-O-Me-m7G (5')ppp(5')G Anti Reverse Cap Analog (ARCA) cap or $C_{32}H_{43}N_{15}O_{24}P_4$ CleanCap Reagent AG can be substituted at 5' untranslated regions of the RNA molecule.

In some embodiments, a modRNA disclosed herein can be targeted to at least one tissue type. In some aspects, a modRNA disclosed herein can be targeted to heart tissue. In other embodiments, a modRNA can be targeted to a specific cell type. In some aspects, a modRNA can be targeted to a heart cell. In other aspects, a heart cell that can be targeted by a modRNA disclosed herein can be a cardiomyocyte, a cardio fibroblast, or a combination thereof. In some embodiments, a modRNA can be administered to a heart cell in vitro. In other embodiments, a modRNA can be administered to a heart cell in vivo. In some other embodiments, a modRNA can be administered to a stem cell ex vivo wherein the modRNA-treated stem cell can be administered to the heart.

In some embodiments, a modRNA can be administered to a heart cell in vitro at about 0.001 μg modRNA/mm$^2$/500 heart cells to about 10 μg modRNA/mm$^2$/500 heart cells, at about 0.01 μg modRNA/mm$^2$/500 heart cells to about 9.5 μg modRNA/mm$^2$/500 heart cells, or about at about 0.1 μg modRNA/mm$^2$/500 heart cells to about 9.0 μg modRNA/mm$^2$/500 heart cells. In some embodiments, a modRNA can be administered to a heart cell in vitro at about 0.001 μg, about 0.005 μg, about 0.010 μg, about 0.025 μg, about 0.050 μg, at about 0.1 μg, about 0.5 μg, about 1.0 μg, about 1.5 μg, about 2.0 μg, about 2.5 μg, about 3.0 μg, about 3.5 μg, about 4.0 μg, about 4.5 μg, 5.0 μg, about 5.5 μg, about 6.0 μg, about 6.5 μg, about 7.0 μg, about 7.5 μg, about 8.0 μg, about 8.5 μg, about 9.0 μg, about 9.5 μg, or about 10 μg modRNA/mm$^2$/500 heart cells. In some embodiments, a modRNA can be administered to a cardiomyocyte cell in vitro at about 0.001 μg modRNA/mm$^2$/500 cardiomyocytes to about 10 μg modRNA/mm$^2$/500 cardiomyocytes, at about 0.01 μg modRNA/mm$^2$/500 cardiomyocytes to about 9.5 μg modRNA/mm$^2$/500 cardiomyocytes, or about at about 0.1 μg modRNA/mm$^2$/500 cardiomyocytes to about 9.0 μg modRNA/mm$^2$/500 cardiomyocytes. In some embodiments, a modRNA can be administered to a cardiomyocyte in vitro at about 0.001 μg, about 0.005 μg, about 0.010 μg, about 0.025 μg, about 0.050 μg, at about 0.1 μg, about 0.5 μg, about 1.0 μg, about 1.5 μg, about 2.0 μg, about 2.5 μg, about 3.0 μg, about 3.5 μg, about 4.0 μg, about 4.5 μg, 5.0 μg, about 5.5 μg, about 6.0 μg, about 6.5 μg, about 7.0 μg, about 7.5 μg, about 8.0 μg, about 8.5 μg, about 9.0 μg, about 9.5 μg, or about g modRNA/mm$^2$/500 cardiomyocytes. In some embodiments, a modRNA can be administered to a cardio fibroblast in vitro at about 0.001 μg modRNA/mm$^2$/500 cardio fibroblasts to about 10 μg modRNA/mm$^2$/500 cardio fibroblasts, at about 0.01 μg modRNA/mm$^2$/500 cardio fibroblasts to about 9.5 μg modRNA/mm$^2$/500 cardio fibroblasts, or about at about 0.10 μg modRNA/mm$^2$/500 cardio fibroblasts to about 9.0 μg modRNA/mm$^2$/500 cardio fibroblasts. In some embodiments, a modRNA can be administered to a cardio fibroblast in vitro at about 0.001 g, about 0.005 μg, about 0.010 μg, about 0.025 μg, about 0.050 μg, at about 0.1 μg, about 0.5 μg, about 1.0 μg, about 1.5 μg, about 2.0 μg, about 2.5 μg, about 3.0 μg, about 3.5 μg, about 4.0 μg, about 4.5 μg, 5.0 μg, about 5.5 μg, about 6.0 μg, about 6.5 μg, about 7.0 μg, about 7.5 μg, about 8.0 μg, about 8.5 μg, about 9.0 μg, about 9.5 μg, or about 10 μg modRNA/mm$^2$/500 cardio fibroblasts. In some embodiments, a modRNA can be administered to a stem cell in vitro at about 0.001 μg modRNA/mm$^2$/500 stem cells to about 10 μg modRNA/mm$^2$/500 stem cells, at about 0.01 μg modRNA/mm$^2$/500 stem cells to about 9.5 μg modRNA/mm$^2$/500 stem cells, or about at about 0.10 μg modRNA/mm$^2$/500 stem cells to about 9.0 μg modRNA/mm$^2$/500 stem cells. In some embodiments, a modRNA can be administered to a stem cell in vitro at about 0.001 μg, about 0.005 μg, about 0.010 μg, about 0.025 μg, about 0.050 μg, at about 0.1 μg, about 0.5 μg, about 1.0 g, about 1.5 μg, about 2.0 μg, about 2.5 μg, about 3.0 μg, about 3.5 μg, about 4.0 μg, about 4.5 g, 5.0 μg, about 5.5 μg, about 6.0 μg, about 6.5 μg, about 7.0 μg, about 7.5 μg, about 8.0 μg, about 8.5 μg, about 9.0 μg, about 9.5 μg, or about 10 μg modRNA/mm$^2$/500 stem cells.

In some embodiments, a modRNA can be administered in vivo at about 25 μg to about 100 μg, about 30 μg to about 95 μg, or about 35 μg to about 90 μg to a to a heart weighing about 110 mg to about 190 mg. In some embodiments, a modRNA can be administered in vivo at about 25 μg, about 30 μg, about 35 μg, about 40 μg, about 45 μg, about 50 μg, about 55 μg, about 60 μg, about 65 μg, about 70 μg, about 75 μg, about 80 μg, about 85 μg, about 90 μg, about 95 μg, or about 100 μg to a to a heart weighing about 110 mg to about 190 mg. In some aspects, a heart weighing about 110 mg to about 190 mg may be a mouse heart.

In some embodiments, a modRNA can be administered in vivo at about 1 mg to about 100 mg, about 1.5 mg to about 95 mg, or about 2 mg to about 90 mg to a to a heart weighing about 250 μg to about 320 μg. In some embodiments, a modRNA can be administered in vivo at about 1 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, or about 100 mg to a to a heart weighing about 250 μg to about 320 μg. In some aspects, a heart weighing about 250 μg to about 320 μg may be a pig heart. In other aspects, a heart weighing about 250 μg to about 320 μg may be a human heart wherein the human is under the age of 10. In still other aspects, a heart weighing about 250 μg to about 320 μg may be a human heart wherein the human is under the age of 18. In yet other aspects, a heart weighing about 250 μg to about 320 μg may be a an adult human heart.

In some embodiments, a modRNA can be administered to a heart in vivo at about 1 g/10 μg heart tissue to about 10 mg/10 μg heart tissue or about 10 μg/10 μg heart tissue to about 5 mg/10 μg heart tissue. In some other embodiments, a modRNA can be administered to a heart in vivo at about 1 μg/10 μg heart tissue, about 5 μg/10 μg heart tissue, about 10 μg/10 μg heart tissue, about 15 μg/10 μg heart tissue, about 20 μg/10 μg heart tissue, about 30 μg/10 μg heart tissue, about μg/10 μg heart tissue, about 50 μg/10 μg heart tissue, about 75 μg/10 μg heart tissue, about 100 μg/10 μg heart tissue, about 1 mg/10 μg heart tissue, about 3 mg/10 μg heart tissue, about 5 mg/10 μg heart tissue, or about 10 mg/10 μg heart tissue.

In some embodiments, a modRNA can encompass an exogenous RNA sequence for a gene coding for a protein native to the heart tissue with at least nucleoside substitution. In some other embodiments, a modRNA can encompass an exogenous RNA sequence for a gene coding for a protein known to be down regulated in heart diseases with at least nucleoside substitution. In some embodiments, a modRNA can encompass an exogenous RNA sequence for a gene coding for a protein known to be down regulated in heart failure with at least nucleoside substitution. In some other embodiments, a modRNA can encompass an exogenous RNA sequence for a gene coding for a protein known to be down regulated in dilated cardiomyopathy with at least nucleoside substitution. In still some other embodiments, a modRNA can encompass an exogenous RNA sequence for pip4k2c with at least nucleoside substitution. In still some other embodiments, a modRNA can encompass an exogenous RNA sequence for human pip4k2c with at least nucleoside substitution wherein the exogenous RNA sequence for human pip4k2c is:

```
                                             (SEQ ID NO: 1)
5'atggcgtcctcctcggtcccaccagccacggtatcggcggcgacagc
aggccccggcccaggtttcggcttcgcctccaagaccaagaagaagcat
ttcgtgcagcagaaggtgaaggtgttccgggcggccgacccgctggtgg
gtgtgttcctgtggggcgtagcccactcgatcaatgagctcagccaggt
gcctcccccggtgatgctgctgccagatgactttaaggccagctccaag
atcaaggtcaacaatcaccttttccacagggaaaatctgcccagtcatt
tcaagttcaaggagtattgtccccaggtcttcaggaacctccgtgatcg
atttggcattgatgaccaagattacttggtgtcccttacccgaaacccc
cccagcgaaagtgaaggcagtgatggtcgcttccttatctcctacgatc
ggactctggtcatcaaagaagtatccagtgaggacattgctgacatgca
tagcaacctctccaactatcaccagtacattgtgaagtgccatggcaac
acgcttctgccccagttcctggggatgtaccgagtcagtgtggacaacg
aagacagctacatgcttgtgatgcgcaatatgtttagccaccgtcttcc
tgtgcacaggaagtatgacctcaagggttccctagtgtcccgggaagcc
agcgataaggaaaaggttaaagaattgcccacccttaaggatatggact
ttctcaacaagaaccagaaagtatatattggtgaagaggagaagaaaat
atttctggagaagctgaagagagatgtggagtttctagtgcagctgaag
atcatggactacagccttctgctaggcatccacgacatcattcggggct
ctgaaccagaggaggaagcgcccgtgcgggaggatgagtcagaggtgga
tggggactgcagcctgactggacctcctgctctggtgggctcctatggc
acctccccagagggtatcggaggctacatccattcccatcggcccctgg
gcccaggagagtttgagtccttcattgatgtctatgccatccggagtgc
tgaaggagcccccagaaggaggtctacttcatgggcctcattgatatc
cttacacagtatgatgctaagaagaaagcagctcatgcagccaaaactg
tcaagcatggggctggggcagagatctctactgtccatccggagcagta
tgctaagcgattcctggattttattaccaacatctttgccta3'
```

In some aspects, a modRNA herein can encompass an RNA sequence having about 10% to about 99% of SEQ ID NO: 1. In some aspects, a modRNA herein can encompass an RNA sequence having at least 80% (i.e., about 80%, 85%, 90%, 95%, 99%) of SEQ ID NO: 1.

In various embodiments, compositions disclosed herein may encompass at least modRNA encoding for modulating gene expression wherein modulation of gene expression can be a result of treatment with a modRNA disclosed herein. In some aspects, treatment of a heart cell in vitro with a modRNA disclosed herein can modulate gene expression of at least one gene compared to an untreated heart cell. In some other aspects, treatment of a heart cell in vitro with a modRNA disclosed herein can modulate gene expression of pip4k2c compared to an untreated heart cell. In other aspects, treatment of a heart cell in vitro with a modRNA disclosed herein can increase gene expression of pip4k2c compared to an untreated heart cell. In still other aspects, treatment of a heart cell in vitro with a modRNA disclosed herein can increase gene expression of pip4k2c by at least about 1-fold to about 50-fold, about 5-fold to about 40-fold, or about 10-fold to about 30-fold compared to an untreated heart cell. In still other aspects, treatment of a heart cell in vitro with a modRNA disclosed herein can increase gene expression of pip4k2c by at least about 1-fold, about 5-fold, about 10-fold, about 15-fold, about 20-fold, about 25-fold, about 30 fold, about 35-fold, about 40-fold, about 45-fold, or about 50-fold compared to an untreated heart cell. In other aspects, treatment of a heart cell in vitro with a modRNA disclosed herein can increase gene expression of pip4k2c by at least about 1-fold, about 5-fold, about 10-fold, about 15-fold, about 20-fold, about 25-fold, about 30 fold, about 35-fold, about 40-fold, about 45-fold, or about 50-fold compared to an untreated heart after about 0 hours to about 25 days, or after about 12 hours to about 21 days following modRNA treatment. In some other aspects, treatment of a heart cell in vitro with a modRNA disclosed herein can increase gene expression of pip4k2c by at least about 1-fold, about 5-fold, about 10-fold, about 15-fold, about 20-fold, about 25-fold, about 30 fold, about 35-fold, about 40-fold, about 45-fold, or about 50-fold compared to an untreated heart after about 0 hours, about 12 hours, about 1 days, about 2 days, about 3 days, about 4 days, about 5 days, about 6 days, about 7 days about 8 days, about 9 days, about 10 days, about 12 days, about 14 days, about 16 days, about 18 days, about 20 days, about 21 days, or about 25 days following modRNA treatment. In some aspects, treatment of a heart in vivo with a modRNA disclosed herein can modulate gene expression of at least one gene compared to an untreated heart. In some other aspects, treatment of a heart in vivo with a modRNA disclosed herein can modulate gene expression of pip4k2c compared to an untreated heart. In other aspects, treatment of a heart in vivo with a modRNA disclosed herein can increase gene expression of pip4k2c compared to an untreated heart. In still other aspects, treatment of a heart in vivo with a modRNA disclosed herein can increase gene expression of pip4k2c by at least about 1-fold to about 50-fold, about 5-fold to about 40-fold, or about 10-fold to about 30-fold compared to an untreated heart. In still other aspects, treatment of a heart in vivo with a modRNA disclosed herein can increase gene expression of pip4k2c by at least about 1-fold, about 5-fold, about 10-fold, about 15-fold, about 20-fold, about 25-fold, about 30 fold, about 35-fold, about 40-fold, about 45-fold, or about 50-fold compared to an untreated heart. In other aspects, treatment of a heart in vivo with a modRNA disclosed herein can increase gene expression of pip4k2c by at least about 1-fold, about 5-fold, about 10-fold, about 15-fold, about 20-fold, about 25-fold, about 30 fold, about 35-fold, about 40-fold, about 45-fold, or about 50-fold compared to an untreated heart after about 0 hours to about 25 days, or after about 12 hours to about 21 days following modRNA treatment. In some other aspects, treatment of a heart in vivo with a modRNA disclosed herein can increase gene expression of pip4k2c by at least about 1-fold, about 5-fold, about 10-fold, about 15-fold, about 20-fold, about 25-fold, about 30 fold, about 35-fold, about 40-fold, about 45-fold, or about 50-fold compared to an untreated heart after about 0 hours, about 12 hours, about 1 days, about 2 days, about 3 days, about 4 days, about 5 days, about 6 days, about 7 days, about 8 days, about 9 days, about 10 days, about 12 days, about 14 days, about 16 days, about 18 days, about 20 days, about 21 days, or about 25 days following modRNA treatment.

In various embodiments, compositions disclosed herein may encompass at least modRNA encoding for modulating gene expression wherein modulation of gene expression can result in an increase of protein expression following treatment with a modRNA disclosed herein. In some aspects, treatment of a heart cell in vitro with a modRNA disclosed herein can modulate protein expression of at least one protein compared to an untreated heart cell. In some other aspects, treatment of a heart cell in vitro with a modRNA disclosed herein can modulate protein expression of pip4k2c compared to an untreated heart cell. In other aspects, treatment of a heart cell in vitro with a modRNA disclosed herein can increase protein expression of pip4k2c compared to an untreated heart cell. In still other aspects, treatment of a heart cell in vitro with a modRNA disclosed herein can increase protein expression of pip4k2c by at least about 1-fold to about 50-fold, about 5-fold to about 40-fold, or about 10-fold to about 30-fold compared to an untreated heart cell. In still other aspects, treatment of a heart cell in vitro with a modRNA disclosed herein can increase protein expression of pip4k2c by at least about at least about 1-fold, about 5-fold, about 10-fold, about 15-fold, about 20-fold, about 25-fold, about 30 fold, about 35-fold, about 40-fold, about 45-fold, or about 50-fold compared to an untreated heart cell. In other aspects, treatment of a heart cell in vitro with a modRNA disclosed herein can increase protein expression of pip4k2c by at least about 1-fold, about 5-fold, about 10-fold, about 15-fold, about 20-fold, about 25-fold, about 30 fold, about 35-fold, about 40-fold, about 45-fold, or about 50-fold compared to an untreated heart after about 0 hours to about 25 days, or after about 12 hours to about 21 days following modRNA treatment. In some other aspects, treatment of a heart cell in vitro with a modRNA disclosed herein can increase protein expression of pip4k2c by at least about 1-fold, about 5-fold, about 10-fold, about 15-fold, about 20-fold, about 25-fold, about 30 fold, about 35-fold, about 40-fold, about 45-fold, or about 50-fold compared to an untreated heart after about 0 hours, about 12 hours, about 1 days, about 2 days, about 3 days, about 4 days, about 5 days, about 6 days, about 7 days, about 8 days, about 9 days, about 10 days, about 12 days, about 14 days, about 16 days, about 18 days, about 20 days, about 21 days, or about 25 days following modRNA treatment. In some aspects, treatment of a heart in vivo with a modRNA disclosed herein can modulate protein expression of at least one protein compared to an untreated heart. In some other aspects, treatment of a heart in vivo with a modRNA disclosed herein can modulate gene expression of pip4k2c compared to an untreated heart. In other aspects, treatment of a heart in vivo with a modRNA disclosed herein can increase protein expression of pip4k2c compared to an untreated heart. In still other aspects, treatment of a heart in vivo with a modRNA disclosed herein can increase protein expression of pip4k2c by at least about 1-fold to about 50-fold, about 5-fold to about 40-fold, or about 10-fold to about 30-fold compared to an untreated heart. In still other aspects, treatment of a heart in vivo with a modRNA disclosed herein can increase protein expression of pip4k2c by at least about 1-fold, about 5-fold, about 10-fold, about 15-fold, about 20-fold, about 25-fold, about 30 fold, about 35-fold, about 40-fold, about 45-fold, or about 50-fold compared to an untreated heart. In other aspects, treatment of a heart in vivo with a modRNA disclosed herein can increase protein expression of pip4k2c by at least about 1-fold, about 5-fold, about 10-fold, about 15-fold, about 20-fold, about 25-fold, about 30 fold, about 35-fold, about 40-fold, about 45-fold, or about 50-fold compared to an untreated heart after about 0 hours to about 25 days, or after about 12 hours to about 21 days following modRNA treatment. In some other aspects, treatment of a heart in vivo with a modRNA disclosed herein can increase protein expression of pip4k2c by at least about 1-fold, about 5-fold, about 10-fold, about 15-fold, about 20-fold, about 25-fold, about 30 fold, about 35-fold, about 40-fold, about 45-fold, or about 50-fold compared to an untreated heart after about 0 hours, about 12 hours, about 1 days, about 2 days, about 3 days, about 4 days, about 5 days, about 6 days, about 7 days, about 8 days, about 9 days, about 10 days, about 12 days, about 14 days, about 16 days, about 18 days, about 20 days, about 21 days, or about 25 days following modRNA treatment.

In some aspects, treatment of a heart in vivo with a modRNA disclosed herein can improve heart function compared to an untreated heart. In some other aspects, treatment of a heart in vivo with a modRNA encoding for pip4k2c can improve heart function compared to an untreated heart. In some other aspects, treatment of a HF heart in vivo with a modRNA encoding for pip4k2c can improve heart function compared to an untreated HF heart. In some other aspects, treatment of a HF heart in vivo with a modRNA encoding for pip4k2c can improve heart function by about 1% to about 26% or about 2% to about 20% compared to an untreated HF heart. In yet some other aspects, treatment of a HF heart in vivo with a modRNA encoding for pip4k2c can improve heart function by about 1%, about 2%, about 5%, about 10%, about 12%, about 14%, about 16%, about 18%, about 20%, about 22%, about 24%, or about 26% compared to an untreated HF heart. In still some other aspects, treatment of a HF heart in vivo with a modRNA encoding for pip4k2c can improve heart function by about 1% to about 26% or about 2% to about 20% compared to an untreated HF heart after about 0 hours to about 25 days, or after about 12 hours to about 21 days following modRNA treatment. In still some other aspects, treatment of a DCM heart in vivo with a modRNA encoding for pip4k2c can improve heart function compared to an untreated DCM heart. In some other aspects, treatment of a DCM heart in vivo with a modRNA encoding for pip4k2c can improve heart function by about 1% to about 26% or about 2% to about 20% compared to an untreated DCM heart. In yet some other aspects, treatment of a DCM heart in vivo with a modRNA encoding for pip4k2c can improve heart function by about 1%, about 2%, about 5%, about 10%, about 12%, about 14%, about 16%, about 18%, about 20%, about 22%, about 24%, or about 26% compared to an untreated DCM heart. In still some other aspects, treatment of a DCM heart in vivo with a modRNA encoding for pip4k2c can improve heart function by about 1% to about 26% or about 2% to about 20% compared to an untreated DCM heart after about 0 hours to about 25 days, or after about 12 hours to about 21 days following modRNA treatment.

In some aspects, treatment of a heart in vivo with a modRNA disclosed herein can reduce cardiac fibrosis compared to an untreated heart. In some other aspects, treatment of a heart in vivo with a modRNA encoding for pip4k2c can reduce cardiac fibrosis compared to an untreated heart. In some other aspects, treatment of a HF heart in vivo with a modRNA encoding for pip4k2c can reduce cardiac fibrosis compared to an untreated HF heart. In some other aspects, treatment of a HF heart in vivo with a modRNA encoding for pip4k2c can reduce cardiac fibrosis by about 1% to about 26% or about 2% to about 20% compared to an untreated HF heart. In yet some other aspects, treatment of a HF heart in vivo with a modRNA encoding for pip4k2c can reduce cardiac fibrosis by about 1%, about 2%, about 5%, about 10%, about 12%, about 14%, about 16%, about 18%, about 20%, about 22%, about 24%, or about 26% compared to an untreated HF heart. In still some other aspects, treatment of a HF heart in vivo with a modRNA encoding for pip4k2c can reduce cardiac fibrosis by about 1% to about 26% or about 2% to about 20% compared to an untreated HF heart after about 0 hours to about 25 days, or after about 12 hours to about 21 days following modRNA treatment. In still some other aspects, treatment of a DCM heart in vivo with a modRNA encoding for pip4k2c can reduce cardiac fibrosis compared to an untreated DCM heart. In some other aspects, treatment of a DCM heart in vivo with a modRNA encoding for pip4k2c can reduce cardiac fibrosis by about 1% to about 26% or about 2% to about 20% compared to an untreated DCM heart. In yet some other aspects, treatment of a DCM heart in vivo with a modRNA encoding for pip4k2c can reduce cardiac fibrosis by about 1%, about 2%, about 5%, about 10%, about 12%, about 14%, about 16%, about 18%, about 20%, about 22%, about 24%, or about 26% compared to an untreated DCM heart. In still some other aspects, treatment of a DCM heart in vivo with a modRNA encoding for pip4k2c can reduce cardiac fibrosis by about 1% to about 26% or about 2% to about 20% compared to an untreated DCM heart after about 0 hours to about 25 days, or after about 12 hours to about 21 days following modRNA treatment.

In some aspects, treatment of a heart in vivo with a modRNA disclosed herein can reverse cardiac hypertrophy compared to an untreated heart. In some other aspects, treatment of a heart in vivo with a modRNA encoding for pip4k2c can reverse cardiac hypertrophy compared to an untreated heart. In some other aspects, treatment of a HF heart in vivo with a modRNA encoding for pip4k2c can reverse cardiac hypertrophy compared to an untreated HF heart. In some other aspects, treatment of a HF heart in vivo with a modRNA encoding for pip4k2c can reverse cardiac hypertrophy by about 1% to about 26% or about 2% to about 20% compared to an untreated HF heart. In yet some other aspects, treatment of a HF heart in vivo with a modRNA encoding for pip4k2c can reverse cardiac hypertrophy by about 1%, about 2%, about 5%, about 10%, about 12%, about 14%, about 16%, about 18%, about 20%, about 22%, about 24%, or about 26% compared to an untreated HF heart. In still some other aspects, treatment of a HF heart in vivo with a modRNA encoding for pip4k2c can reverse cardiac hypertrophy by about 1% to about 26% or about 2% to about 20% compared to an untreated HF heart after about 0 hours to about 25 days, or after about 12 hours to about 21 days following modRNA treatment. In still some other aspects, treatment of a DCM heart in vivo with a modRNA encoding for pip4k2c can reverse cardiac hypertrophy compared to an untreated DCM heart. In some other aspects, treatment of a DCM heart in vivo with a modRNA encoding for pip4k2c can reverse cardiac hypertrophy by about 1% to about 26% or about 2% to about 20% compared to an untreated DCM heart. In yet some other aspects, treatment of a DCM heart in vivo with a modRNA encoding for pip4k2c can reverse cardiac hypertrophy by about 1%, about 2%, about 5%, about 10%, about 12%, about 14%, about 16%, about 18%, about 20%, about 22%, about 24%, or about 26% compared to an untreated DCM heart. In still some other aspects, treatment of a DCM heart in vivo with a modRNA encoding for pip4k2c can reverse cardiac hypertrophy by about 1% to about 26% or about 2% to about 20% compared to an untreated DCM heart after about 0 hours to about 25 days, or after about 12 hours to about 21 days following modRNA treatment.

In some aspects, treatment of a heart in vivo with a modRNA disclosed herein can modulate fractional shorting (FS) compared to an untreated heart. In some other aspects, treatment of a heart in vivo with a modRNA encoding for pip4k2c can increase fractional shorting compared to an untreated heart. In some other aspects, treatment of a HF heart in vivo with a modRNA encoding for pip4k2c can increase fractional shorting compared to an untreated HF heart. In still some other aspects, treatment of a DCM heart in vivo with a modRNA encoding for pip4k2c can increase fractional shorting compared to an untreated DCM heart. In some other aspects, treatment of a DCM heart in vivo with a modRNA encoding for pip4k2c can increase fractional shorting by about 1% to about 26% or about 2% to about 20% compared to an untreated DCM heart. In yet some other aspects, treatment of a DCM heart in vivo with a modRNA encoding for pip4k2c can increase fractional shorting by about 1%, about 2%, about 5%, about 10%, about 12%, about 14%, about 16%, about 18%, about 20%, about 22%, about 24%, or about 26% compared to an untreated DCM heart. In still some other aspects, treatment of a DCM heart in vivo with a modRNA encoding for pip4k2c can increase fractional shorting by about 1% to about 26% or about 2% to about 20% compared to an untreated DCM heart after about 0 hours to about 25 days, or after about 12 hours to about 21 days following modRNA treatment.

In some aspects, treatment of a heart in vivo with a modRNA disclosed herein can modulate left ventricular internal diastolic diameter end diastole (LVIDd) compared to an untreated heart. In some other aspects, treatment of a heart in vivo with a modRNA encoding for pip4k2c can decrease LVIDd compared to an untreated heart. In some other aspects, treatment of a HF heart in vivo with a modRNA encoding for pip4k2c can decrease LVIDd compared to an untreated HF heart. In still some other aspects, treatment of a DCM heart in vivo with a modRNA encoding for pip4k2c can decrease LVIDd compared to an untreated DCM heart. In some other aspects, treatment of a DCM heart in vivo with a modRNA encoding for pip4k2c can decrease LVIDd by about 0.1 cm to about 2 cm or about 0.5 cm to about 1 cm compared to an untreated DCM heart. In yet some other aspects, treatment of a DCM heart in vivo with a modRNA encoding for pip4k2c can decrease LVIDd by about 0.01 cm, about 0.05 cm, about 0.1 cm, about 0.2 cm, about 0.5 cm, about 0.8 cm, about 1.0 cm, about 1.2 cm, about 1.5 cm, about 1.8 cm, or about 2.0 cm compared to an untreated DCM heart. In still some other aspects, treatment of a DCM heart in vivo with a modRNA encoding for pip4k2c can decrease LVIDd by about 0.1 cm to about 2 cm or about 0.5 cm to about 1 cm compared to an untreated DCM heart after about 0 hours to about 25 days, or after about 12 hours to about 21 days following modRNA treatment.

In some aspects, treatment of a heart in vivo with a modRNA disclosed herein can modulate left ventricular internal diastolic diameter end systole (LVIDs) compared to an untreated heart. In some other aspects, treatment of a heart in vivo with a modRNA encoding for pip4k2c can decrease LVIDs compared to an untreated heart. In some other aspects, treatment of a HF heart in vivo with a modRNA encoding for pip4k2c can decrease LVIDs compared to an untreated HF heart. In still some other aspects, treatment of a DCM heart in vivo with a modRNA encoding for pip4k2c can decrease LVIDs compared to an untreated DCM heart. In some other aspects, treatment of a DCM heart in vivo with a modRNA encoding for pip4k2c can decrease LVIDs by about 0.1 cm to about 3 cm or about 0.5 cm to about 2 cm compared to an untreated DCM heart. In yet some other aspects, treatment of a DCM heart in vivo with a modRNA encoding for pip4k2c can decrease LVIDs by about 0.01 cm, about 0.05 cm, about 0.1 cm, about 0.2 cm, about 0.5 cm, about 0.8 cm, about 1.0 cm, about 1.2 cm, about 1.5 cm, about 1.8 cm, about 2.0 cm, about 2.5 cm, or about 3.0 cm compared to an untreated DCM heart. In still some other aspects, treatment of a DCM heart in vivo with a modRNA encoding for pip4k2c can decrease LVIDs by about 0.1 cm to about 3 cm or about 0.5 cm to about 2 cm compared to an untreated DCM heart after about 0 hours to about 25 days, or after about 12 hours to about 21 days following modRNA treatment.

In some aspects, treatment of a heart in vivo with a modRNA disclosed herein can modulate the total heart weight (HW) compared to an untreated heart. In some other aspects, treatment of a heart in vivo with a modRNA encoding for pip4k2c can decrease HW compared to an untreated heart. In some other aspects, treatment of a HF heart in vivo with a modRNA encoding for pip4k2c can decrease HW compared to an untreated HF heart. In still some other aspects, treatment of a DCM heart in vivo with a modRNA encoding for pip4k2c can decrease HW compared to an untreated DCM heart. In some other aspects, treatment of a DCM heart in vivo with a modRNA encoding for pip4k2c can decrease HW by about 0.1 mg to about 3 mg or about 0.5 mg to about 2 mg compared to an untreated DCM heart. In yet some other aspects, treatment of a DCM heart in vivo with a modRNA encoding for pip4k2c can decrease HW by about 0.01 mg, about 0.05 mg, about 0.1 mm, about 0.2 mg, about 0.5 mg, about 0.8 mg, about 1.0 mg, about 1.2 mg, about 1.5 mg, about 1.8 mg, about 2.0 mg, about 2.5 mg, or about 3.0 mg compared to an untreated DCM heart. In still some other aspects, treatment of a DCM heart in vivo with a modRNA encoding for pip4k2c can decrease HW by about 0.1 mg to about 3 mg or about 0.5 mg to about 2 mg compared to an untreated DCM heart after about 0 hours to about 25 days, or after about 12 hours to about 21 days following modRNA treatment.

In some aspects, treatment of a heart in vivo with a modRNA disclosed herein can modulate the heart weight to tibia length (HW/TL) compared to an untreated heart. In some other aspects, treatment of a heart in vivo with a modRNA encoding for pip4k2c can decrease HW/TL compared to an untreated heart. In some other aspects, treatment of a HF heart in vivo with a modRNA encoding for pip4k2c can decrease HW/TL compared to an untreated HF heart. In still some other aspects, treatment of a DCM heart in vivo with a modRNA encoding for pip4k2c can decrease HW/TL compared to an untreated DCM heart. In some other aspects, treatment of a DCM heart in vivo with a modRNA encoding for pip4k2c can decrease HW/TL by about 0.1 mg/mm to about 3 mg/mm or about 0.5 mg/mm to about 2 mg/mm compared to an untreated DCM heart. In yet some other aspects, treatment of a DCM heart in vivo with a modRNA encoding for pip4k2c can decrease HW/TL by about 0.01 mg/mm, about 0.05 mg/mm, about 0.1 mg/mm, about 0.2 mg/mm, about 0.5 mg/mm, about 0.8 mg/mm, about 1.0 mg/mm, about 1.2 mg/mm, about 1.5 mg/mm, about 1.8 mg/mm, about 2.0 mg/mm, about 2.5 mg/mm, or about 3.0 mg/mm compared to an untreated DCM heart. In still some other aspects, treatment of a DCM heart in vivo with a modRNA encoding for pip4k2c can decrease HW/TL by about 0.1 mg/mm to about 3 mg/mm or about 0.5 mg/mm to about 2 mg/mm compared to an untreated DCM heart after about 0 hours to about 25 days, or after about 12 hours to about 21 days following modRNA treatment.

In some aspects, treatment of a heart in vivo with a modRNA disclosed herein can modulate the cross sectional area of cardiac sarcolemma compared to an untreated heart. In some other aspects, treatment of a heart in vivo with a modRNA encoding for pip4k2c can decrease cross sectional area of cardiac sarcolemma compared to an untreated heart. In some other aspects, treatment of a HF heart in vivo with a modRNA encoding for pip4k2c can decrease cross sectional area of cardiac sarcolemma compared to an untreated HF heart. In still some other aspects, treatment of a DCM heart in vivo with a modRNA encoding for pip4k2c can decrease cross sectional area of cardiac sarcolemma compared to an untreated DCM heart. In some other aspects, treatment of a DCM heart in vivo with a modRNA encoding for pip4k2c can decrease cross sectional area of cardiac sarcolemma by about 10 $\mu m^2$ to about 100 $mm^2$ or about 10 $mm^2$ to about 90 $mm^2$ compared to an untreated DCM heart. In yet some other aspects, treatment of a DCM heart in vivo with a modRNA encoding for pip4k2c can decrease cross sectional area of cardiac sarcolemma by about 10 $\mu m^2$, about 50 $\mu m^2$, about 100 $\mu m^2$, about 500 $\mu m^2$, about 1 $mm^2$, about 5 $mm^2$, about 10 $mm^2$, about 20 $mm^2$, about 30 $mm^2$, about 40 $mm^2$, about 50 $mm^2$, about 60 $mm^2$, about 70 $mm^2$, about 80 $mm^2$, about 90 $mm^2$, or about 100 $mm^2$ compared to an untreated DCM heart. In still some other aspects, treatment of a DCM heart in vivo with a modRNA encoding for pip4k2c can decrease cross sectional area of cardiac sarcolemma by about 10 $\mu m^2$ to about 100 $mm^2$ or about 10 $mm^2$ to about 90 $mm^2$ compared to an untreated DCM heart after about 0 hours to about 25 days, or after about 12 hours to about 21 days following modRNA treatment.

In some aspects, treatment of a heart in vivo with a modRNA disclosed herein can modulate the fibrotic area in the left ventricle compared to an untreated heart. In some other aspects, treatment of a heart in vivo with a modRNA encoding for pip4k2c can decrease fibrotic area in the left ventricle compared to an untreated heart. In some other aspects, treatment of a HF heart in vivo with a modRNA encoding for pip4k2c can decrease fibrotic area in the left ventricle compared to an untreated HF heart. In still some other aspects, treatment of a DCM heart in vivo with a modRNA encoding for pip4k2c can decrease fibrotic area in the left ventricle compared to an untreated DCM heart. In some other aspects, treatment of a DCM heart in vivo with a modRNA encoding for pip4k2c can decrease fibrotic area in the left ventricle by about 30% to about 60% or about 40% to about 70% compared to an untreated DCM heart. In yet some other aspects, treatment of a DCM heart in vivo with a modRNA encoding for pip4k2c can decrease fibrotic area in the left ventricle by about 30%, about 35%, about 40%, about 45%, about 50%, about 55%, about 60%, about 65%, or about 70% compared to an untreated DCM heart. In still some other aspects, treatment of a DCM heart in vivo with a modRNA encoding for pip4k2c can decrease fibrotic area in the left ventricle by about 30% to about 60% or about 40% to about 70% compared to an untreated DCM heart after about 0 hours to about 25 days, or after about 12 hours to about 21 days following modRNA treatment.

In some aspects, treatment of a heart in vivo with a modRNA disclosed herein can improve life expectancy (or "survival rate") of the subject compared to a subject with an untreated heart. In some other aspects, treatment of a heart in vivo with a modRNA encoding for pip4k2c can increase the life expectancy of a subject compared to a subject with an untreated heart. In some other aspects, treatment of a HF heart in vivo with a modRNA encoding for pip4k2c can increase the life expectancy of a subject compared to a subject with an untreated HF heart. In still some other aspects, treatment of a DCM heart in vivo with a modRNA encoding for pip4k2c can increase the life expectancy of a subject compared to a subject with an untreated DCM heart. In some other aspects, treatment of a DCM heart in vivo with a modRNA encoding for pip4k2c can increase the life expectancy of a subject by about 5% to about 100% compared to life expectancy of a subject with an untreated DCM heart. In yet some other aspects, treatment of a DCM heart in vivo with a modRNA encoding for pip4k2c can increase the life expectancy of a subject by about 75%, about 80%, about 85%, about 90%, about 95%, or about 100% compared to life expectancy of a subject with an untreated DCM heart. In still some other aspects, treatment of a DCM heart in vivo with a modRNA encoding for pip4k2c can increase the life expectancy of a subject by about 5% to about 100% compared to life expectancy of a subject with an untreated DCM heart after about 0 hours to about 25 days following modRNA treatment. In some other aspects, treatment of a DCM heart in vivo with a modRNA encoding for pip4k2c can increase the life expectancy of a subject by about 5% to about 100% compared to life expectancy of a subject with an untreated DCM heart after about 0 hours, about 1 day, about 5 days, about 10 days, about 15 days, about 20 days, or about 25 days following modRNA treatment. In other aspects, treatment of a DCM heart in vivo with a modRNA encoding for pip4k2c can increase the life expectancy of a subject by about 5% to about 100% compared to survival rate of a subject with an untreated DCM heart after about 19 days, about 20 days, about 21 days, about 22 days, about 23 days, about 24 days, or about 25 days following modRNA treatment.

In some aspects, treatment of a heart in vivo with a modRNA disclosed herein can decrease gene expression of at least one marker of cardiac hypertrophy compared to an untreated heart. In some other aspects, treatment of a heart in vivo with a modRNA encoding for pip4k2c can decrease gene expression of at least one marker of cardiac hypertrophy compared to an untreated heart. In still some other aspects, treatment of a HF heart in vivo with a modRNA encoding for pip4k2c can decrease gene expression of at least one marker of cardiac hypertrophy compared to an untreated HF heart. In yet some other aspects, treatment of a DCM heart in vivo with a modRNA encoding for pip4k2c can decrease gene expression of at least one marker of cardiac hypertrophy compared to an untreated DCM heart. In other aspects, treatment of a DCM heart in vivo with a modRNA encoding for pip4k2c can decrease gene expression of at least one marker of cardiac hypertrophy by at least 1-fold compared to an untreated DCM heart. In some other aspects, treatment of a DCM heart in vivo with a modRNA encoding for pip4k2c can decrease gene expression of at least one marker of cardiac hypertrophy selected from atrial natriuretic peptide (ANP) and B-type natriuretic peptide (BNP) compared to an untreated DCM heart.

In some aspects, treatment of a heart in vivo with a modRNA disclosed herein can decrease gene expression of at least one metalloproteinase (MMP) compared to an untreated heart. In some other aspects, treatment of a heart in vivo with a modRNA encoding for pip4k2c can decrease gene expression of at least one MMP compared to an untreated heart. In still some other aspects, treatment of a HF heart in vivo with a modRNA encoding for pip4k2c can decrease gene expression of at least one MMP compared to an untreated HF heart. In yet some other aspects, treatment of a DCM heart in vivo with a modRNA encoding for pip4k2c can decrease gene expression of at least one MMP compared to an untreated DCM heart. In other aspects, treatment of a DCM heart in vivo with a modRNA encoding for pip4k2c can decrease gene expression of at least one MMP by at least 1-fold compared to an untreated DCM heart. In some other aspects, treatment of a DCM heart in vivo with a modRNA encoding for pip4k2c can decrease gene expression of at least one MMP selected from MMP2, MMP3, MMP7, and MMP9 compared to an untreated DCM heart.

In some aspects, treatment of a heart in vivo with a modRNA disclosed herein can decrease gene expression of at least one fibrosis marker compared to an untreated heart. In some other aspects, treatment of a heart in vivo with a modRNA encoding for pip4k2c can decrease gene expression of at least one fibrosis marker compared to an untreated heart. In still some other aspects, treatment of a HF heart in vivo with a modRNA encoding for pip4k2c can decrease gene expression of at least one fibrosis marker compared to an untreated HF heart. In yet some other aspects, treatment of a DCM heart in vivo with a modRNA encoding for pip4k2c can decrease gene expression of at least one fibrosis marker compared to an untreated DCM heart. In other aspects, treatment of a DCM heart in vivo with a modRNA encoding for pip4k2c can decrease gene expression of at least one fibrosis marker by at least 1-fold compared to an untreated DCM heart. In some other aspects, treatment of a DCM heart in vivo with a modRNA encoding for pip4k2c can decrease gene expression of at least one fibrosis marker selected from Col1a1 (collagen, type I, alpha 1), Col1a2 (collagen, type I, alpha 2), and Col3a1 (collagen, type III, alpha 1) compared to untreated DCM heart.

In some aspects, treatment of a heart in vivo with a modRNA disclosed herein can decrease gene expression of TGFβ1 (transforming growth factor beta 1) compared to an untreated heart. In some other aspects, treatment of a heart in vivo with a modRNA encoding for pip4k2c can decrease gene expression of TGFβ1 compared to an untreated heart. In still some other aspects, treatment of a HF heart in vivo with a modRNA encoding for pip4k2c can decrease gene expression of TGFβ1 compared to an untreated HF heart. In yet some other aspects, treatment of a DCM heart in vivo with a modRNA encoding for pip4k2c can decrease gene expression of TGFβ1 marker compared to an untreated DCM heart. In other aspects, treatment of a DCM heart in vivo with a modRNA encoding for pip4k2c can decrease gene expression of TGFβ1 by at least 1-fold compared to an untreated DCM heart.

In some aspects, treatment of a heart in vivo with a modRNA disclosed herein can decrease gene expression of at least one extracellular matrix protein compared to an untreated heart. In some other aspects, treatment of a heart in vivo with a modRNA encoding for pip4k2c can decrease gene expression of at least one extracellular matrix protein compared to an untreated heart. In still some other aspects, treatment of a HF heart in vivo with a modRNA encoding for pip4k2c can decrease gene expression of at least one extracellular matrix protein compared to an untreated HF heart. In yet some other aspects, treatment of a DCM heart in vivo with a modRNA encoding for pip4k2c can decrease gene expression of at least one extracellular matrix protein compared to an untreated DCM heart. In other aspects, treatment of a DCM heart in vivo with a modRNA encoding for pip4k2c can decrease gene expression of at least one extracellular matrix protein by at least 1-fold compared to an untreated DCM heart. In some other aspects, treatment of a DCM heart in vivo with a modRNA encoding for pip4k2c can decrease gene expression of at least one extracellular matrix protein is selected from Fibronectin 1 (FN1) and connective tissue growth factor (CTGF) compared to untreated DCM heart.

In some aspects, treatment of a heart in vivo with a modRNA disclosed herein can inhibit at least one signaling pathway activated in HF. In some aspects, treatment of a heart in vivo with a modRNA disclosed herein can inhibit at least one signaling pathway activated in DCM. In some aspects, treatment of a heart in vivo with a modRNA disclosed herein can attenuate at least one signaling pathway activated in HF. In some aspects, treatment of a heart in vivo with a modRNA disclosed herein can attenuate at least one signaling pathway activated in DCM. In some aspects, treatment of a heart in vivo with a modRNA disclosed herein can inhibit at least two signaling pathways activated in HF. In some aspects, treatment of a heart in vivo with a modRNA disclosed herein can inhibit at least two signaling pathways activated in DCM. In some aspects, treatment of a heart in vivo with a modRNA disclosed herein can attenuate at least two signaling pathways activated in HF. In some aspects, treatment of a heart in vivo with a modRNA disclosed herein can attenuate at least two signaling pathways activated in DCM. In some aspects, treatment of a heart in vivo with a modRNA encoding for pip4k2c as disclosed herein can inhibit at least one signaling pathway activated in HF selected from the mTORC1 pathway and the TGF-β pathway. In some aspects, treatment of a heart in vivo with a modRNA encoding for pip4k2c as disclosed herein can inhibit at least one signaling pathway activated in DCM selected from the mTORC1 pathway and the TGF-β pathway. In some aspects, treatment of a heart in vivo with a modRNA encoding for pip4k2c as disclosed herein can attenuate at least one signaling pathway activated in HF selected from the mTORC1 pathway and the TGF-β pathway. In some aspects, treatment of a heart in vivo with a modRNA encoding for pip4k2c as disclosed herein can attenuate at least one signaling pathway activated in DCM selected from the mTORC1 pathway and the TGF-β pathway. In some aspects, treatment of a heart in vivo with a modRNA encoding for pip4k2c as disclosed herein can inhibit both the mTORC1 pathway and the TGF-β pathway in the heart. In some aspects, treatment of a heart in vivo with a modRNA encoding for pip4k2c as disclosed herein can attenuate both the mTORC1 pathway and the TGF-β pathway in the heart. In some aspects, treatment of a heart in vivo with a modRNA encoding for pip4k2c as disclosed herein can inhibit at least one downstream target of the mTORC1 pathway in the heart. In some aspects, treatment of a heart in vivo with a modRNA encoding for pip4k2c as disclosed herein can attenuate at least one downstream target of the mTORC1 pathway in the heart. In some aspects, treatment of a heart in vivo with a modRNA encoding for pip4k2c as disclosed herein can inhibit at least one downstream target of the TGF-β pathway in the heart. In some aspects, treatment of a heart in vivo with a modRNA encoding for pip4k2c as disclosed herein can attenuate at least one downstream target of the TGF-β pathway in the heart. In some aspects, treatment of a heart in vivo with a modRNA encoding for pip4k2c as disclosed herein can inhibit at least one downstream target of the mTORC1 pathway in the heart and inhibit at least one downstream target of the TGF-β pathway in the heart. In some aspects, treatment of a heart in vivo with a modRNA encoding for pip4k2c as disclosed herein can inhibit at least one downstream target of the mTORC1 pathway in the heart and attenuate at least one downstream target of the TGF-β pathway in the heart. In some aspects, treatment of a heart in vivo with a modRNA encoding for pip4k2c as disclosed herein can attenuate at least one downstream target of the mTORC1 pathway in the heart and inhibit at least one downstream target of the TGF-β pathway in the heart. In some aspects, treatment of a heart in vivo with a modRNA encoding for pip4k2c as disclosed herein can attenuate at least one downstream target of the mTORC1 pathway in the heart and attenuate at least one downstream target of the TGF-β pathway in the heart.

(b) Pharmaceutically Acceptable Carriers and Excipients

In various embodiments, compositions disclosed herein may further compromise one or more pharmaceutically acceptable diluent(s), excipient(s), or carrier(s). As used herein, a pharmaceutically acceptable diluent, excipient, or carrier, refers to a material suitable for administration to a subject without causing undesirable biological effects or interacting in a deleterious manner with any of the components of the composition in which it is contained. Pharmaceutically acceptable diluents, carriers, and excipients can include, but are not limited to, physiological saline, Ringer's solution, phosphate solution or buffer, buffered saline, and other carriers known in the art. Pharmaceutical compositions may also include stabilizers, anti-oxidants, colorants, other medicinal or pharmaceutical agents, carriers, adjuvants, preserving agents, stabilizing agents, wetting agents, emulsifying agents, solution promoters, salts, solubilizers, antifoaming agents, antioxidants, dispersing agents, surfactants, and combinations thereof.

In various embodiments, compositions disclosed herein comprise a pharmaceutical composition comprised of at least one modRNA encoding for at least one cardiac specific gene. In various embodiments, compositions disclosed herein comprise a pharmaceutical composition comprised of at least one modRNA encoding for at least one cardiac specific protein. In various embodiments, compositions disclosed herein comprise a pharmaceutical composition comprised of at least one modRNA encoding for pip4k2c.

In some embodiments, pharmaceutical compositions disclosed herein may be formulated in a conventional manner using one or more physiologically acceptable carriers including excipients and auxiliaries which can facilitate processing of active components into preparations which can be used pharmaceutically. In other embodiments, proper formulation of pharmaceutical compositions disclosed herein may be dependent upon the route of administration chosen. In an aspect, any of the well-known techniques, carriers, and excipients may be used as suitable and as understood in the art. A summary of pharmaceutical compositions described herein may be found, for example, in Hoover, John E., Remington's Pharmaceutical Sciences, Mack Publishing Co., Easton, Pa. 1995; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference in their entirety for such disclosure.

In various embodiments, pharmaceutical compositions described herein may be formulated in conventional manner using one or more physiologically acceptable carriers comprising excipients and auxiliaries to facilitate processing of genetically modified endothelial progenitor cells into preparations which can be used pharmaceutically. In other embodiments, any of the well-known techniques, carriers, and excipients may be used as suitable and as understood in the art.

In various embodiments, pharmaceutical compositions described herein may be an aqueous suspension comprising one or more polymers as suspending agents. In some aspects, polymers that may comprise pharmaceutical compositions described herein include: water-soluble polymers such as cellulosic polymers, e.g., hydroxypropyl methylcellulose; water-insoluble polymers such as cross-linked carboxyl-containing polymers; mucoadhesive polymers, selected from, for example, carboxymethylcellulose, carbomer (acrylic acid polymer), poly(methylmethacrylate), polyacrylamide, polycarbophil, acrylic acid/butyl acrylate copolymer, sodium alginate, and dextran; or a combination thereof. In other aspects, compositions disclosed herein may comprise at least 5%, at least 10%, at least 20%, at least 25%, at least 30%, at least 35%, at least 40%, at least 45%, at least 50% total amount of polymers as suspending agent (s) by total weight of the composition In various embodiments, pharmaceutical compositions disclosed herein may comprise a viscous formulation. In some aspects, viscosity of the composition may be increased by the addition of one or more gelling or thickening agents. In other aspects, compositions disclosed herein may comprise one or more gelling or thickening agents in an amount to provide a sufficiently viscous formulation to remain on treated tissue. In still other aspects, compositions disclosed herein may comprise at least 5%, at least 10%, at least 20%, at least 25%, at least 30%, at least 35%, at least 40%, at least 45%, at least 50% total amount of gelling or thickening agent(s) by total weight of the composition. In yet other aspects, suitable thickening agents can be hydroxypropyl methylcellulose, hydroxyethyl cellulose, polyvinylpyrrolidone, carboxymethyl cellulose, polyvinyl alcohol, sodium chondroitin sulfate, sodium hyaluronate. In other aspects, viscosity enhancing agents can be acacia (gum arabic), agar, aluminum magnesium silicate, sodium alginate, sodium stearate, bladderwrack, bentonite, carbomer, carrageenan, Carbopol, xanthan, cellulose, microcrystalline cellulose (MCC), ceratonia, chitin, carboxymethylated chitosan, chondrus, dextrose, furcellaran, gelatin, Ghatti gum, guar gum, hectorite, lactose, sucrose, maltodextrin, mannitol, sorbitol, honey, maize starch, wheat starch, rice starch, potato starch, gelatin, sterculia gum, xanthum gum, gum tragacanth, ethyl cellulose, ethylhydroxyethyl cellulose, ethylmethyl cellulose, methyl cellulose, hydroxyethyl cellulose, hydroxyethylmethyl cellulose, hydroxypropyl cellulose, poly(hydroxyethyl methacrylate), oxypolygelatin, pectin, polygeline, povidone, propylene carbonate, methyl vinyl ether/maleic anhydride copolymer (PVM/MA), poly (methoxyethyl methacrylate), poly(methoxyethoxyethyl methacrylate), hydroxypropyl cellulose, hydroxypropylmethyl-cellulose (HPMC), sodium carboxymethyl-cellulose (CMC), silicon dioxide, polyvinylpyrrolidone (PVP: povidone), Splenda® (dextrose, maltodextrin and sucralose), or combinations thereof. In specific embodiments, suitable thickening agent may be carboxymethylcellulose.

In various embodiments, pharmaceutical compositions disclosed herein may comprise additional agents or additives selected from a group including surface-active agents, detergents, solvents, acidifying agents, alkalizing agents, buffering agents, tonicity modifying agents, ionic additives effective to increase the ionic strength of the solution, antimicrobial agents, antibiotic agents, antifungal agents, antioxidants, preservatives, electrolytes, antifoaming agents, oils, stabilizers, enhancing agents, and the like. In some aspects, pharmaceutical compositions disclosed herein may comprise at least 5%, at least 10%, at least 20%, at least 25%, at least 30%, at least 35%, at least 40%, at least 45%, at least 50% total amount of one or more agents by total weight of the composition. In other aspects, one or more of these agents may be added to improve the performance, efficacy, safety, shelf-life and/or other property of the muscarinic antagonist composition of the invention. In preferred aspects, additives will be biocompatible, and will not be harsh, abrasive, or allergenic.

In various embodiments, pharmaceutical compositions disclosed herein may comprise one or more acidifying agents. As used herein, "acidifying agents" refers to compounds used to provide an acidic medium. Such compounds include, by way of example and without limitation, acetic acid, amino acid, citric acid, fumaric acid and other alpha hydroxy acids, such as hydrochloric acid, ascorbic acid, and nitric acid and others known to those of ordinary skill in the art. In some aspects, any pharmaceutically acceptable organic or inorganic acid may be used. In other aspects, compositions disclosed herein may comprise at least 5%, at least 10%, at least 20%, at least 25%, at least 30%, at least 35%, at least 40%, at least 45%, at least 50% total amount of one or more acidifying agents by total weight of the composition.

In various embodiments, pharmaceutical compositions disclosed herein may comprise one or more alkalizing agents. As used herein, "alkalizing agents" are compounds used to provide alkaline medium. Such compounds include, by way of example and without limitation, ammonia solution, ammonium carbonate, diethanolamine, monoethanolamine, potassium hydroxide, sodium borate, sodium carbonate, sodium bicarbonate, sodium hydroxide, triethanolamine, and trolamine and others known to those of ordinary skill in the art. In some aspects, any pharmaceutically acceptable organic or inorganic base can be used. In other aspects, compositions disclosed herein may comprise at least 5%, at least 10%, at least 20%, at least 25%, at least 30%, at least 35%, at least 40%, at least 45%, at least 50% total amount of one or more alkalizing agents by total weight of the composition.

In various embodiments, pharmaceutical compositions disclosed herein may comprise one or more antioxidants. As used herein, "antioxidants" are agents that inhibit oxidation and thus can be used to prevent the deterioration of preparations by the oxidative process. Such compounds include, by way of example and without limitation, ascorbic acid, ascorbyl palmitate, butylated hydroxyanisole, butylated hydroxytoluene, hypophophorous acid, monothioglycerol, propyl gallate, sodium ascorbate, sodium bisulfite, sodium formaldehyde sulfoxylate and sodium metabisulfite and other materials known to one of ordinary skill in the art. In some aspects, compositions disclosed herein may comprise at least 5%, at least 10%, at least 20%, at least 25%, at least 30%, at least 35%, at least 40%, at least 45%, at least 50% total amount of one or more antioxidants by total weight of the composition.

In other embodiments, pharmaceutical compositions disclosed herein may comprise a buffer system. As used herein, a "buffer system" is a composition comprised of one or more buffering agents wherein "buffering agents" are compounds used to resist change in pH upon dilution or addition of acid or alkali. Buffering agents include, by way of example and without limitation, potassium metaphosphate, potassium phosphate, monobasic sodium acetate and sodium citrate anhydrous and dihydrate and other materials known to one of ordinary skill in the art. In some aspects, any pharmaceutically acceptable organic or inorganic buffer can be used. In another aspect, compositions disclosed herein may comprise at least 5%, at least 10%, at least 20%, at least 25%, at least 30%, at least 35%, at least 40%, at least 45%, at least 50% total amount of one or more buffering agents by total weight of the composition. In other aspects, the amount of one or more buffering agents may depend on the desired pH level of a composition. In some embodiments, pharmaceutical compositions disclosed herein may have a pH of about 6 to about 9. In other embodiments, pharmaceutical compositions disclosed herein may have a pH greater than about 8, greater than about 7.5, greater than about 7, greater than about 6.5, or greater than about 6. In a preferred embodiment, compositions disclosed herein may have a pH greater than about 6.8.

In various embodiments, pharmaceutical compositions disclosed herein may comprise one or more preservatives. As used herein, "preservatives" refers to agents or combination of agents that inhibits, reduces or eliminates bacterial growth in a pharmaceutical dosage form. Non-limiting examples of preservatives include Nipagin, Nipasol, isopropyl alcohol and a combination thereof. In some aspects, any pharmaceutically acceptable preservative can be used. In other aspects, pharmaceutical compositions disclosed herein may comprise at least 5%, at least 10%, at least 20%, at least 25%, at least 30%, at least 35%, at least 40%, at least 45%, at least 50% total amount of one or more preservatives by total weight of the composition.

In other embodiments, pharmaceutical compositions disclosed herein may comprise one or more surface-acting reagents or detergents. In some aspects, surface-acting reagents or detergents may be synthetic, natural, or semi-synthetic. In other aspects, compositions disclosed herein may comprise anionic detergents, cationic detergents, zwitterionic detergents, ampholytic detergents, amphoteric detergents, nonionic detergents having a steroid skeleton, or a combination thereof. In still other aspects, pharmaceutical compositions disclosed herein may comprise at least 5%, at least 10%, at least 20%, at least 25%, at least 30%, at least 35%, at least 40%, at least 45%, at least 50% total amount of one or more surface-acting reagents or detergents by total weight of the composition.

In various embodiments, pharmaceutical compositions disclosed herein may comprise one or more stabilizers. As used herein, a "stabilizer" refers to a compound used to stabilize an active agent against physical, chemical, or biochemical process that would otherwise reduce the therapeutic activity of the agent. Suitable stabilizers include, by way of example and without limitation, succinic anhydride, albumin, sialic acid, creatinine, glycine and other amino acids, niacinamide, sodium acetyltryptophonate, zinc oxide, sucrose, glucose, lactose, sorbitol, mannitol, glycerol, polyethylene glycols, sodium caprylate and sodium saccharin and others known to those of ordinary skill in the art. In some aspects, pharmaceutical compositions disclosed herein may comprise at least 5%, at least 10%, at least 20%, at least 25%, at least 30%, at least 35%, at least 40%, at least 45%, at least 50% total amount of one or more stabilizers by total weight of the composition.

In other embodiments, pharmaceutical compositions disclosed herein may comprise one or more tonicity agents. As used herein, a "tonicity agents" refers to a compound that can be used to adjust the tonicity of the liquid formulation. Suitable tonicity agents include, but are not limited to, glycerin, lactose, mannitol, dextrose, sodium chloride, sodium sulfate, sorbitol, trehalose and others known to those or ordinary skill in the art. Osmolarity in a composition may be expressed in milliosmoles per liter (mOsm/L). Osmolarity may be measured using methods commonly known in the art. In preferred embodiments, a vapor pressure depression method is used to calculate the osmolarity of the compositions disclosed herein. In some aspects, the amount of one or more tonicity agents comprising a pharmaceutical composition disclosed herein may result in a composition osmolarity of about 150 mOsm/L to about 500 mOsm/L, about 250 mOsm/L to about 500 mOsm/L, about 250 mOsm/L to about 350 mOsm/L, about 280 mOsm/L to about 370 mOsm/L or about 250 mOsm/L to about 320 mOsm/L. In other aspects, a composition herein may have an osmolality ranging from about 100 mOsm/kg to about 1000 mOsm/kg, from about 200 mOsm/kg to about 800 mOsm/kg, from about 250 mOsm/kg to about 500 mOsm/kg, or from about 250 mOsm/kg to about 320 mOsm/kg, or from about 250 mOsm/kg to about 350 mOsm/kg or from about 280 mOsm/kg to about 320 mOsm/kg. In some embodiments, a pharmaceutical composition described herein has an osmolarity of about 100 mOsm/L to about 1000 mOsm/L, about 200 mOsm/L to about 800 mOsm/L, about 250 mOsm/L to about 500 mOsm/L, about 250 mOsm/L to about 350 mOsm/L, about 250 mOsm/L to about 320 mOsm/L, or about 280 mOsm/L to about 320 mOsm/L. In still other aspects, pharmaceutical compositions disclosed herein may comprise at least 5%, at least 10%, at least 20%, at least 25%, at least 30%, at least 35%, at least 40%, at least 45%, at least 50% total amount of one or more tonicity modifiers by total weight of the composition.

(c) Dosage Formulations

In some embodiments, pharmaceutical compositions disclosed herein may be formulated for parenteral administration by injection. In some aspects, parenteral administration by injection can be by bolus injection and/or continuous infusion. In some embodiments, pharmaceutical compositions disclosed herein may be formulated for parenteral administration by intracardiac injection. As used herein, the term "intracardiac injection" refers to an injection given directly into the heart muscles or ventricles. In some other embodiments, pharmaceutical compositions disclosed herein may be formulated for parenteral administration by catheter-based intracoronary infusion. In still some other embodiments, pharmaceutical compositions disclosed herein may formulated for parenteral administration by pericardial injection.

In various embodiments, pharmaceutical compositions disclosed herein that are formulations for injection may be presented in unit dosage form. In some aspects, a unit dosage form may be in ampoules and or in multi-dose containers. In other aspects, pharmaceutical compositions disclosed herein may be suspensions, solutions or emulsions in oily or aqueous vehicles. In still other aspects, pharmaceutical compositions disclosed herein may contain formulary agents such as suspending, stabilizing and/or dispersing agents. In yet other aspects, pharmaceutical compositions disclosed herein may be presented in unit-dose or multi-dose containers. Non-limiting examples of unit-dose or multi-dose containers include sealed ampoules and vials. In an aspect, pharmaceutical compositions disclosed herein may be stored in powder form or in a freeze-dried (lyophilized) condition requiring only the addition of the sterile liquid carrier immediately prior to use. In other aspects, pharmaceutical compositions disclosed herein may be extemporaneous injection solutions and suspensions may be prepared from sterile powders, granules, tablets or a combination thereof. In still other aspects, pharmaceutical compositions disclosed herein may be cryofrozen prior to storage. As used herein, "cryofrozen" refers to and/or describes cryopreservation biological samples frozen in a manner that maintains vitality and subsequently thawed out again as needed while maintaining vitality. In some aspects, pharmaceutical compositions disclosed herein may be cryofrozen and stored for up to 1 week, up to 4 weeks, up to 8 weeks, up to 16 weeks, up to 25 weeks, up to 50 weeks, up to 100 weeks, or up to 200 weeks while maintaining vitality.

In various embodiments, pharmaceutical compositions described herein for parenteral administration can include aqueous and non-aqueous (oily) sterile injection solutions of the compositions which may contain antioxidants, buffers, bacteriostats and solutes which render the formulation isotonic with the blood of the intended recipient; and aqueous and non-aqueous sterile suspensions which may include suspending agents and thickening agents. In some aspects, pharmaceutical compositions described herein may include lipophilic solvents or vehicles. Non-limiting examples of vehicles include fatty oils such as sesame oil, or synthetic fatty acid esters, such as ethyl oleate or triglycerides, or liposomes. In various embodiments, pharmaceutical compositions described herein may be aqueous injection suspensions. In some aspects, pharmaceutical compositions described herein may contain substances which increase the viscosity of the suspension, such as sodium carboxymethyl cellulose, sorbitol, or dextran. In other aspects, pharmaceutical compositions described herein may comprise suitable stabilizers or agents which increase the solubility of the enzymes and fining agents to allow for the preparation of highly concentrated solutions.

(II) Uses of Compositions

In various embodiments, compositions disclosed herein may be effective for treating heart disease following administration to a subject in need. In other embodiments, compositions disclosed herein may be effective for treating heart failure (HF) following administration to a subject in need. In still other embodiments, compositions disclosed herein may be effective for treating dilated cardiomyopathy (DCM) following administration to a subject in need. In other embodiments, compositions disclosed herein may be effective for improving at least one symptom of DCM following administration to a subject in need.

A suitable subject includes a human, a livestock animal, a companion animal, a lab animal, or a zoological animal. In one embodiment, the subject may be a rodent, e.g., a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a specific embodiment, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In preferred embodiments, the subject is a human.

In various embodiments, a subject in need may have been diagnosed with at least one heart disease. In some aspects, the subject may have HF. A subject having HF can be identified by routine medical examination, e.g., laboratory tests, EKG, ECG, echocardiogram, stress tests, MRI, coronary angioplasty, myocardial biopsy, organ functional tests, CT scans, or ultrasounds. In some embodiments, the subject to be treated by the methods described herein may be a human patient who has undergone or is subjected to a therapy for treating HF. A subject suspected of having any of HF might show one or more symptoms of HF. A subject at risk for the HF can be a subject having one or more of the risk factors for that disorder, for example, carrying a genetic mutation associated with HF with no disease manifestations at the time of the treatment. A subject to be treated by the methods herein can have HF classified according to, but not limited to, the New York Heart Association classification. As an example, the New York Heart Association classification is symptom-based scale that classifies HF in four categories: in Class I heart failure, the subject does not have any symptoms; in Class II heart failure, the subject can perform everyday activities without difficulty but become winded or fatigued upon exertion; in Class 1II, a subject can have trouble completing everyday activities; and in Class IV, the most severe, a subject can be short of breath even at rest. A subject to be treated by the methods herein can have HF classified according to, but not limited to, the American College of Cardiology/American Heart Association guidelines. As an example, the American College of Cardiology/American Heart Association guidelines is a stage-based classification system that uses letters A to D and includes a category for subjects who are at risk of developing heart failure. Using these guidelines, a subject who has several risk factors for heart failure but no signs or symptoms of heart failure is Stage A; a subject who has heart disease but no signs or symptoms of heart failure is Stage B; a subject who has heart disease and is experiencing or has experienced signs or symptoms of heart failure is Stage C; a subject with advanced heart failure requiring specialized treatments is Stage D.

In other aspects, the subject may have or be suspected of having DCM. In other embodiments, a subject may at least one symptom of DCM. In some aspects, a symptom of DCM can be fatigue. In yet other aspects, a symptom of DCM can be dyspnea. In other aspects, a symptom of DCM can be edema. In still other aspects, a symptom of DCM can be ascites. In other aspects, a symptom of DCM can be chest pain. In still other aspects, a symptom of DCM can be a heart murmur.

In some instances, the subject to be treated by the method disclosed herein may have been previously treated for HF in general and/or DCM. In other instances, the subject to be treated has a HF and has undergone or is undergoing another therapy for the HF. Non-limiting examples include medications, surgery, enzyme replacement therapy, haematopoietic stem cell (HSC) transplantation, substrate reduction molecule therapy, chaperone therapy, adeno-associated virus gene therapy, HSC-mediated lentiviral vector gene therapy, or the combined therapy disclosed herein. Examples of medications for HR can include, but are not limited to, angiotensin-converting enzyme (ACE) inhibitors (i.e., enalapril, Lisinopril, captopril), angiotensin II receptor blockers (i.e., losartan, valsartan, candesartan), beta blockers (i.e., carvedilol, metoprolol, bisoprolol), diuretics (i.e., furosemide, thiazide, spironolactone), inotropes, digoxin, and the like. Examples of surgery for the treatment of HR can include, but are not limited to, coronary artery bypass surgery, heart valve repair or replacement, annuloplasty, implantable cardioverter-defibrillators, cardiac resynchronization therapy (CRT), biventricular pacing, ventricular assist devices (VADs), heart transplants, and the like. The prior HR therapy may be complete. Alternatively, the prior HR therapy may still be on-going. In some embodiments, the subject may exhibit improved systemic manifestations associated with the HR (e.g., complete or partial) after the prior therapy. Additional useful agents and therapies can be found in Physician's Desk Reference, 59.sup.th edition, (2005), Thomson P D R, Montvale N.J.; Gennaro et al., Eds. Remington's The Science and Practice of Pharmacy 20.sup.th edition, (2000), Lippincott Williams and Wilkins, Baltimore Md.; Braunwald et al., Eds. Harrison's Principles of Internal Medicine, 15.sup.th edition, (2001), McGraw Hill, NY; Berkow et al., Eds. The Merck Manual of Diagnosis and Therapy, (1992), Merck Research Laboratories, Rahway N.J.

Compositions disclosed herein may decrease and/or reverse DCM-induced cardiac fibrosis compared to DCM-induced cardiac fibrosis in an untreated subject with identical disease condition and predicted outcome. In some aspects, DCM-induced cardiac fibrosis can be deceased by about 20% to about 40% following administration of compositions disclosed herein.

Compositions disclosed herein may decrease and/or reverse DCM-induced left ventricle dilation compared to DCM-induced left ventricle dilation in an untreated subject with identical disease condition and predicted outcome. In some aspects, DCM-induced left ventricle dilation can be deceased by about 20% to about 40% following administration of compositions disclosed herein.

In some embodiments, in vivo treatment of a subject in need thereof with a composition encompassing modRNA encoding for pip4k2c as disclosed herein can inhibit at least one signaling pathway that is hyperactive wherein the inhibited signaling pathway is not hyperactive in a healthy subject. In some aspects, in vivo treatment of a subject in need thereof with a composition encompassing modRNA encoding for pip4k2c as disclosed herein can inhibit at least one signaling pathway selected from the mTORC1 pathway and the TGF-β pathway. In some other aspects, in vivo treatment of a subject in need thereof with a composition encompassing modRNA encoding for pip4k2c as disclosed herein can inhibit mTORC1 and TGF-β signaling pathways.

In some embodiments, in vivo treatment of a subject in need thereof with a composition encompassing modRNA encoding for pip4k2c as disclosed herein can be in combination with another agent that can inhibit mTORC1 and/or TGF-β signaling pathways. In some examples, a composition encompassing modRNA encoding for pip4k2c can be administered in combination with racpamycin. In some examples, a composition encompassing modRNA encoding for pip4k2c can be administered in combination with SB4311542.

In some embodiments, administering a modRNA encoding for pip4k2c to heart tissue of a subject in need thereof replaces the need for treatment of the subject with at least one inhibitor of the mTORC1 pathway. In some aspects, administering a modRNA encoding for pip4k2c to heart tissue of a subject in need thereof replaces the need for treatment of the subject with rapamycin. In some aspects, administering a modRNA encoding for pip4k2c to heart tissue of a subject in need thereof is equally as effective at treating heart failure compared to a mTORC1 inhibitor-treated subject with identical disease condition and predicted outcome. In other aspects, administering a modRNA encoding for pip4k2c to heart tissue of a subject in need thereof is equally as effective at treating heart failure compared to a rapamycin-treated subject with identical disease condition and predicted outcome.

(III) Methods of Using Compositions

Other embodiments of the present disclosure are methods of administering compositions disclosed herein to a subject in need wherein administration treats heart disease. Still other embodiments of the present disclosure are methods of administering compositions disclosed herein to a subject in need wherein at least one symptom of heart disease is improved by at least 25% within one month after administration.

(a) Methods of Administration

In various embodiments, compositions disclosed herein may be administered by parenteral administration. As used herein, "by parenteral administration" refers to administration of the compositions disclosed herein via a route other than through the digestive tract. In some embodiments, compositions disclosed herein may be administered by parenteral injection. In some aspects, administration of the disclosed compositions by parenteral injection may be by subcutaneous, intramuscular, intravenous, intraperitoneal, intracardiac, intraarticular, or intracavernous injection. In other aspects, administration of the disclosed compositions by parenteral injection may be by slow or bolus methods as known in the field. In some embodiments, the route of administration by parenteral injection can be determined by the target location. In some aspects, compositions disclosed herein may be formulated for parenteral administration by intracardiac injection. In some other aspects, compositions disclosed herein may be formulated for parenteral administration by catheter-based intracoronary infusion. In still some other aspects, compositions disclosed herein may formulated for parenteral administration by pericardial injection.

In various embodiments, the dose of compositions disclosed herein to be administered are not particularly limited, and may be appropriately chosen depending on conditions such as a purpose of preventive and/or therapeutic treatment, a type of a disease, the body weight or age of a subject, severity of a disease and the like. In other embodiments, administration of a dose of a composition disclosed herein may comprise a therapeutically effective amount of the composition disclosed herein. As used herein, the term "therapeutically effective" refers to an amount of administered composition that treats heart disease, reduces presentation of at least one symptom associated with heart disease, reverses/prevents cardio fibrosis, reverse/prevent dilation of at least one heart ventricle, reduces total heart weight, improved heart function, increases survivability, or a combination thereof.

"A therapeutically effective amount" as used herein refers to the amount of each active agent (here a modRNA encoding for pip4k2c) required to confer therapeutic effect on the subject, either alone or in combination with one or more other active agents. Effective amounts vary, as recognized by those skilled in the art, depending on route of administration, excipient usage, and co-usage with other active agents. For example, an "effective amount" of a modRNA encoding for pip4k2c can be the amount of the compound that alone, or together with further doses, produces the desired response, e.g., extend lifespan, delay loss of body weight, improve one or more symptoms of HR, and/or attenuate cardiac function decline. This may involve only slowing the progression of the disease temporarily, although more preferably, it involves halting the progression of the disease permanently. This can be monitored by routine methods or can be monitored according to diagnostic methods of the invention discussed herein. The desired response to treatment of the disease or condition also can be delaying the onset of the disease or condition.

Such amounts will depend, of course, on the particular condition being treated, the severity of the condition, the individual patient parameters including age, physical condition, size, gender and weight, the duration of the treatment, the nature of concurrent therapy (if any), the specific route of administration and like factors within the knowledge and expertise of the health practitioner. These factors are well known to those of ordinary skill in the art and can be addressed with no more than routine experimentation. It is generally preferred that a maximum dose of the individual components or combinations thereof be used, that is, the highest safe dose according to sound medical judgment. It will be understood by those of ordinary skill in the art, however, that a patient may insist upon a lower dose or tolerable dose for medical reasons, psychological reasons or for virtually any other reasons. The exact dosage and schedule may be determined by a physician.

A therapeutically effective amount of a composition disclosed herein to be delivered to a subject may be an amount that does not result in undesirable systemic side effects. In various embodiments, compositions administered as disclosed herein may comprise about 5% to about 95%, about 15% to about 85%, or about 25% to about 75% modRNA by total weight of the composition. In other embodiments, compositions administered as disclosed herein may comprise about 5% to about 95%, about 15% to about 85%, or about 25% to about 75% modRNA encoding for pip4k2c by total weight of the composition.

(b) Frequency of Administration

In some embodiments, a composition disclosed herein may be administered to a subject in need thereof once. In some embodiments, a composition disclosed herein may be administered to a subject in need thereof more than once. In other embodiments, a first administration of a composition disclosed herein may be followed by a second administration of a composition disclosed herein. In some embodiments, a first administration of a composition disclosed herein may be followed by a second and third administration of a composition disclosed herein. In some embodiments, a first administration of a composition disclosed herein may be followed by a second, third, and fourth administration of a composition disclosed herein. In some embodiments, a first administration of a composition disclosed herein may be followed by a second, third, fourth, and fifth administration of a composition disclosed herein.

The number of times a composition may be administered to an subject in need thereof can depend on the discretion of a medical professional, the severity of the heart disease, and the subject's response to the formulation. In some embodiments, a composition disclosed herein may be administered continuously; alternatively, the dose of drug being administered may be temporarily reduced or temporarily suspended for a certain length of time (i.e., a "drug holiday"). In some aspects, the length of the drug holiday can vary between 2 days and 1 year, including by way of example only, 2 days, 1 week, 1 month, 6 months, and 1 year. In another aspect, dose reduction during a drug holiday may be from 10%-100%, including by way of example only 10%, 25%, 50%, 75%, and 100%.

In various embodiments, the desired daily dose of compositions disclosed herein may be presented in a single dose or as divided doses administered simultaneously (or over a short period of time) or at appropriate intervals. In other embodiments, administration of a composition disclosed herein may be administered to a subject about once a day, about twice a day, about three times a day. In still other embodiments, administration of a composition disclosed herein may be administered to a subject at least once a day, at least once a day for about 2 days, at least once a day for about 3 days, at least once a day for about 4 days, at least once a day for about 5 days, at least once a day for about 6 days, at least once a day for about 1 week, at least once a day for about 2 weeks, at least once a day for about 3 weeks, at least once a day for about 4 weeks, at least once a day for about 8 weeks, at least once a day for about 12 weeks, at least once a day for about 16 weeks, at least once a day for about 24 weeks, at least once a day for about 52 weeks and thereafter. In a preferred embodiment, administration of a composition disclosed herein may be administered to a subject once about 4 weeks.

In some embodiments, a composition as disclosed may be initially administered followed by a subsequent administration of one for more different compositions or treatment regimens. In other embodiments, a composition as disclosed may be administered after administration of one for more different compositions or treatment regimens.

(IV) Kits

The present disclosure also provides kits for use in treating heart failure as described herein. A kit for therapeutic use as described herein may include one or more containers comprising a modified mRNA (modRNA) encoding for type 2 phosphatidylinositol-5-phosphate 4-kinase gamma (pip4k2c). The modRNA encoding for pip4k2c may be formulated in a pharmaceutical composition.

In some embodiments, the kit can additionally comprise instructions for use of a modRNA encoding for pip4k2c in any of the methods described herein. The included instructions may comprise a description of administration of the modRNA encoding for pip4k2c or a pharmaceutical composition comprising such to a subject to achieve the intended activity in a subject. The kit may further comprise a description of selecting a subject suitable for treatment based on identifying whether the subject is in need of the treatment. In some embodiments, the instructions comprise a description of administering the modRNA encoding for pip4k2c or the pharmaceutical composition comprising such to a subject who has or is suspected of having heart failure.

The instructions relating to the use of the modRNA encoding for pip4k2c or the pharmaceutical composition comprising such as described herein generally include information as to dosage, dosing schedule, and route of administration for the intended treatment. The containers may be unit doses, bulk packages (e.g., multi-dose packages) or sub-unit doses. Instructions supplied in the kits of the disclosure are typically written instructions on a label or package insert. The label or package insert indicates that the pharmaceutical compositions are used for treating, delaying the onset, and/or alleviating a disease or disorder in a subject.

The kits provided herein are in suitable packaging. Suitable packaging includes, but is not limited to, vials, bottles, jars, flexible packaging, and the like. Also contemplated are packages for use in combination with a specific device, such as an inhaler, nasal administration device, or an infusion device. A kit may have a sterile access port (for example, the container may be an intravenous solution bag or a vial having a stopper pierceable by a hypodermic injection needle). The container may also have a sterile access port. A modRNA encoding for pip4k2c may be considered an active agent.

Kits optionally may provide additional components such as buffers and interpretive information. Kits can optionally provide additional agents to be used in combination with a modRNA encoding for pip4k2c disclosed herein. Normally, the kit comprises a container and a label or package insert(s) on or associated with the container. In some embodiment, the disclosure provides articles of manufacture comprising contents of the kits described above.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Blackwell, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985»; *Transcription and Translation* (B. D. Hames & S. J. Higgins, eds. (1984»; *Animal Cell Culture* (R. I. Freshney, ed. (1986»; *Immobilized Cells and Enzymes* (IRL Press, (1986»; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

The following examples are included to demonstrate preferred embodiments of the disclosure. It should be appreciated by those of skill in the art that the techniques disclosed in the examples that follow represent techniques discovered by the inventors to function well in the practice of the present disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the present disclosure.

Introduction to Examples 1-5

Heart disease is major worldwide health problem with an increasing socioeconomic burden (Go et al., Circulation 129, e28-e292 (2014), the disclosure of which is incorporated herein). Dilated cardiomyopathy (DCM) is a condition caused by genetics or non-genetic exposure in which the heart becomes enlarged and cannot pump blood effectively (Weintraub et al., Lancet 390, 400-414 (2017), the disclosure of which is incorporated herein). Pathological hypertrophy occurs in response to sustained cardiac overload and it is often accompanied by increased fibrosis, immune response, cardiac scaring and subsequently leads to heart failure (HF) (Dargie et al., Heart 91 Suppl 2, ii3-6, 31, 43-38 (2005), the disclosure of which is incorporated herein). Therefore, unraveling the mechanistic molecular pathways triggered by pathological stressors, for example DCM, can lead to the development of new therapeutic options for heart failure (HF) in general and, specifically remedies for DCM.

Pip4k2c is a type 2 phosphatidylinositol-5-phosphate 4-kinase (PI5P4K), which converts phosphatidylinositol-5-phosphate to phosphatidylinositol 4,5-bisphosphate in mammals. The mammalian gene PI5P4K encodes for three enzymes—PI5P4Kα, PI5P4Kβ, and PI5P4Kγ—that play an important role in development, homeostasis and diseases (Gupta et al., PNAS 110, 5963-5968 (2013); Mackey et al., Sci Signal 7, ra104 (2014); and Mathre et al., Biosci Rep 39 (2019), the disclosures of which are incorporated herein). Pip4k2c is expressed primarily in the kidney, brain, heart, and testis (Clarke et al., J Comp Neurol 517, 296-312 (2009); Al-Ramahi et al., ELIFE 6(2017); and Clarke et al., Am J Physiol Renal Physiol 295, F1422-1430 (2008), the disclosures of which are incorporated herein).

Additionally, Pip4k2c was shown to inhibit mTORC1-signaling. The mTORC1 signaling pathway is one of the main signaling pathways that induce cardiac hypertrophy after pressure overload. Moreover, TGF-β signaling plays an important role in the pathogenesis of cardiac fibrosis. To date, it is unknown if Pip4k2c affects mTORC1 and TGF-β signaling in heart diseases. As shown in Examples 1-5 below, increased expression of Pip4k2c significantly attenuated and/or prevented cardiac hypertrophy and fibrosis in the failing heart and improved cardiac function via inhibition of mTORC1 and TGF-β activity—two independent signaling pathways activated in heart failure and other cardiac diseases.

Example 1. Pip4k2c Expression in Human Heart Disease

To investigate the role of Pip4k2c in the heart diseases, Pip4k2c mRNA expression and protein expression was analyzed in heart tissue from human subjects ("patients") with cardiac hypertrophy (CH) and dilated cardiomyopathy (DCM). Specifically, Pip4k2c expression was examined in: 1) left ventricular tissues of failing human hearts obtained from patients with end-stage heart failure during heart transplantation; and 2) normal heart specimens procured from donors who died from non-health related causes (e.g., motor vehicle accidents) whose hearts were unsuitable for transplantation for non-cardiac reasons (FIG. 1A). Before heart tissue collection, informed consent was obtained from the prospective donor patients.

Fold-changes in gene expression were determined by the OCT method (Applied Biosystems Prism 7700 Users Bulletin No. 2, the disclosure of which is incorporated herein) and presented relative to an internal control. qRT-PCR primer sequences used in the examples of this disclosure are provided in Table 1.

TABLE 1

Primer Sequences for qRT-PCR

| Gene | Forward Primer | Reverse Primer |
|---|---|---|
| mPip4k2c | ggagactatggcgtcctcct (SEQ ID NO: 2) | ccggaacaccttcactttct (SEQ ID NO: 3) |
| 18s | agtccctgccctttgtacaca (SEQ ID NO: 4) | cgatccgagggcctcacta (SEQ ID NO: 5) |
| FN1 | aggaagccgaggttttaactg (SEQ ID NO: 6) | aggacgctcataagtgtcacc (SEQ ID NO: 7) |
| Col1a | ctggcaagaagggagatga (SEQ ID NO: 8) | caccatccaaaccactgaaa (SEQ ID NO: 9) |
| Col2a | aggtcttcctggagctgatg (SEQ ID NO: 10) | ccccacagggccttctttac (SEQ ID NO: 11) |
| hPip4k2c | gtggggtagagagtgggtca (SEQ ID NO: 12) | tgctgtgcccagatgtagag (SEQ ID NO: 13) |
| Col3a1 | acagcaaattcacttacacagttc (SEQ ID NO: 14) | ctcattgccttgcgtgttt (SEQ ID NO: 15) |
| ctgf1 | aggaagccgaggttttaactg (SEQ ID NO: 16) | aggaagccgaggttttaactg (SEQ ID NO: 17) |
| MYHC | cagaacaccagcctcatcaa (SEQ ID NO: 18) | gctccttcttcagctcctca (SEQ ID NO: 19) |
| ANP | gcttccaggcatattggag (SEQ ID NO: 20) | gggggcatgacctcatctt (SEQ ID NO: 21) |
| BNP | aagggtctggctgctttg (SEQ ID NO: 22) | cagccaggacttcctcttaatg (SEQ ID NO: 23) |
| mmp-2 | aggacgctcataagtgtcacc (SEQ ID NO: 24) | aggaagccgaggttttaactg (SEQ ID NO: 25) |
| mmp-3 | gctgccatttctaataaaga (SEQ ID NO: 26) | gcacttcctttcacaaag (SEQ ID NO: 27) |
| mmp-7 | ttgaaggatggcaagtatgg (SEQ ID NO: 28) | cgaaggcatgacctagagtgt (SEQ ID NO: 29) |
| mmp-9 | aaggacggccttctggcacacgccttt (SEQ ID NO: 30) | gtggtatagtgggacacatagtgg (SEQ ID NO: 31) |
| mt1-mmp | gagatcaaggccaatgttcggagg (SEQ ID NO: 32) | cggtagtacttattgcccaag (SEQ ID NO: 33) |
| TGF-β | cctgtccaaactaaggc (SEQ ID NO: 34) | ggttttctcatagatggcg (SEQ ID NO: 35) |

Pip4k2c mRNA expression was measured using Real-Time Quantitative PCR (qRT-PCR) on RNA isolated from patient hearts. Briefly, total RNA was isolated using the RNeasy mini kit (Qiagen) and reverse transcribed using Superscript III reverse transcriptase (Invitrogen) according to the manufacturer's instructions. qRT-PCR analyses were performed on a Mastercycler realplex 4 Sequence Detector (Eppendorf) using the cyanine dye, SYBR Green (N',N'-dimethyl-N-[4-[(E)-(3-methyl-1,3-benzothiazol-2-ylidene) methyl]-1-phenylquinolin-1-ium-2-yl]-N-propylpropane-1, 3-diamine). Data were normalized to 18S ribosomal RNA (18S) expression where appropriate (endogenous controls).

Figure 11A:
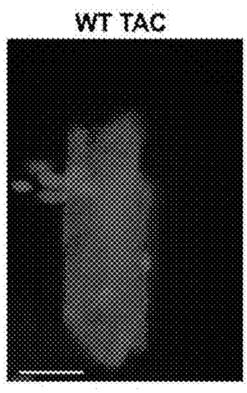
FIGS. 11A-11D depict images of isolated cardiomyocytes (CMs) immunostained with CM sarcomeric structural proteins where the CMs were isolated from the hearts of pip4k2c$^{+/+}$ littermate control (WT) mice 21 days post TAC injury (WT TAC) and pip4k2c$^{-/-}$ (KO-Pip4k2c) mice 21 days post TAC injury (KO-Pip4k2c TAC).
Figure 11B:
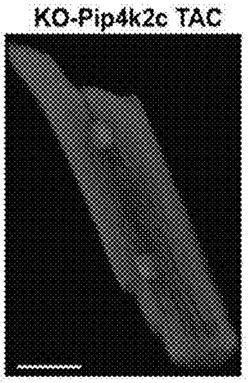
Figure 11C:
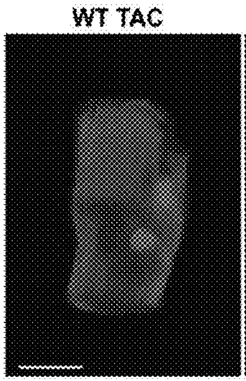
Figure 11D:
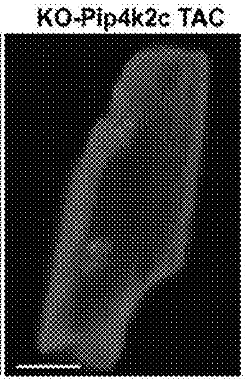

As shown in FIG. 11B, hearts from CH and DCM patients had a significant decrease in Pip4k2c mRNA levels compared to non-failed (NF) left ventricular (LV) myocardium.

Figure 1C:
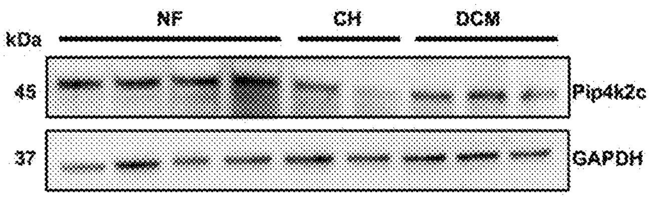
Figure 1D:
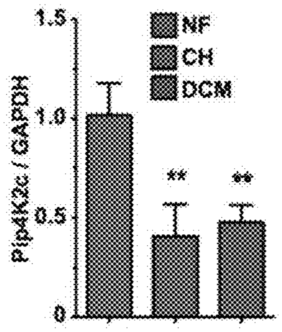
Figure 1E:
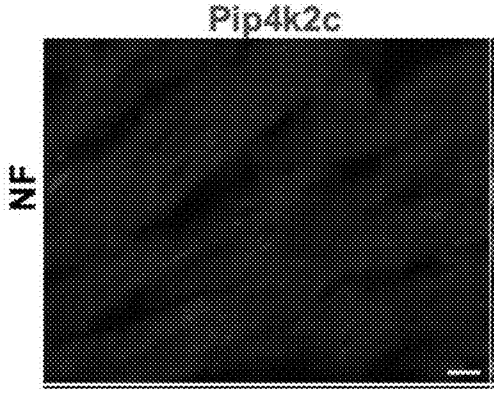
Figure 1F:
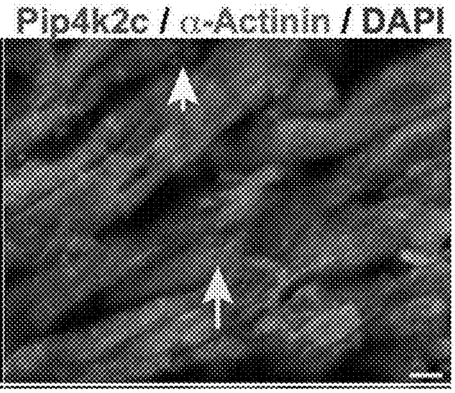
Figure 1G:
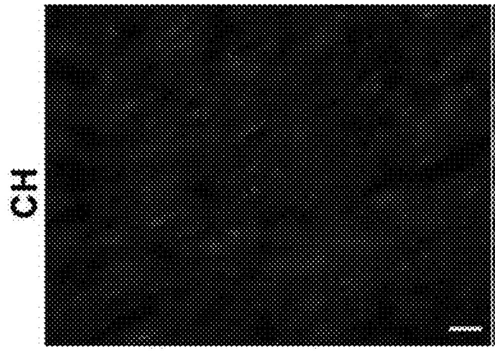
Figure 1H:
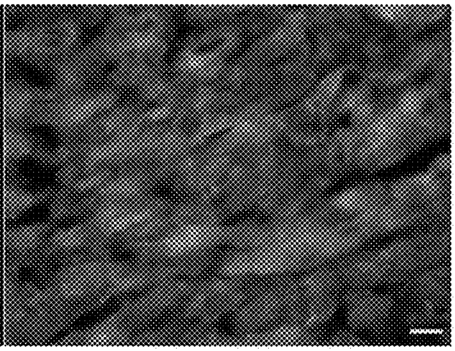
Figure 1I:
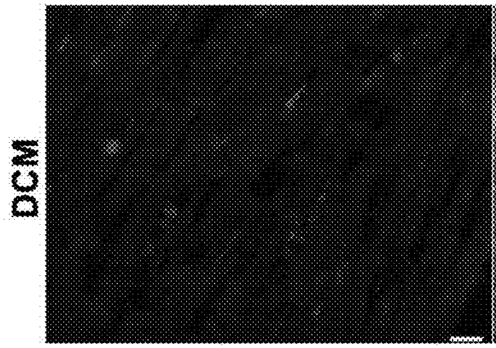
Figure 1J:
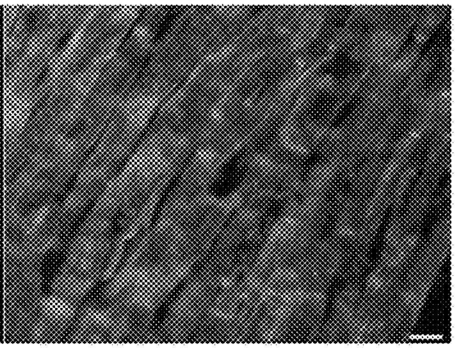

Next, Pip4k2c protein expression was measured in the LV myocardium of heart samples by Western blot analysis. Briefly, total protein was isolated from the tissues by homogenization. Next, equal amounts of protein were resolved using a sodium dodecyl sulfate-polyacrylamnide gel electrophoresis (SDS-PAGE) Electrophoresis system in 4%-15% Mini-PROTEAN TGX stain-free gradient gels (Bio-Rad) and blotted onto polyvinylidene fluoride (PVDF) membranes. The membranes were blocked (5% non-fat dry milk [DM] in Tris-buffered saline (TBS; 50 mM Tris-HCl [pH3 7.4], 150 mM NaCl), for 1 hour at room temperature (25° C.±YQC and were then incubated with primary antibodies diluted in 5% DM in TBS overnight (~12 hours) at 4'C. The following primary antibodies were used for specific protein detection using Western bot analysis at the corresponding dilutions for the examples disclosed herein: anti-Pip4k2c (1:1,000, Proteintech, #17077-1-AP); anti-Phospho-p70 S6 Kinase (Thr389) (P-p70s6k) (1:2,000, Cell Signaling, #9205); p70 S6 Kinase (p70s6k) (1:2,000, Cell Signaling, #9202); anti-GAPDH (horseradish peroxidase [HRP] conjugate 1:3,000, Cell Signaling, #8884); and mouse monoclonal anti-β-actin (horseradish peroxidase [HRP] conjugate 1:3,000, #12262; Cell Signaling). Anti-rabbit and anti-mouse HRP-conjugated secondary antibodies (Sigma-Aldrich) were also used. Antigen and/or antibody complexes were visualized with ChemiDoc Touch imaging system (Bio-Rad). As shown in FIGS. 1C-1D, the LV myocardium of hearts from CH and DCM patients had a significant decrease in Pip4k2c protein levels compared to non-failed (NF) LV myocardium.

Figure 1K:
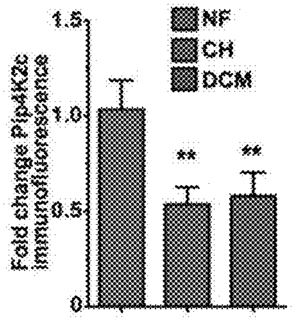

Localized Pip4k2c protein expression was also measured in the LV myocardium of human heart samples by immunostaining frozen heart sections collected from the LV myocardium of CH, DCM, and NF patient hearts. Briefly, the frozen human heart sections were rehydrated in phosphate buffered saline (PBS) for 5 minutes followed by permeabilization with PBS with 0.1% triton X100 (PBST) for 7 minutes. Slides were then treated with 3% $H_2O_2$ for 5 minutes. After 3 washes with PBST for 5 minutes each, the samples were blocked with PBS+5% Donkey normal serum+0.1% Triton X100 (PBSST) for 2 hours at room temperature. Next, primary antibodies were diluted in PBSST and then added to the samples. Slides were next incubated overnight (~12 hours) at 4° C. Slides were washed with PBST (5 times for 4 minutes each) followed by incubation with a secondary antibody (Invitrogen, 1:200) diluted in PBST for 2 hours at room temperature. The samples were further washed with PBST (3 times for 5 minutes each) and stained with DAPI (4',6-diamidino-2-phenylindole; 1 μg/ml) or Hoechst 33342 (1 μg/ml) diluted in PBST for 7 minutes. After 5 washes with PBST for 4 minutes each, and one time with tap water (for 4 minutes), slides were mounted with mounting medium (VECTASHIELD) for imaging. Stained slides were stored at 4° C. All stainings were performed on 3-8 hearts/group, with 2-3 sections/heart. The fluorescent images were taken on Zeiss fluorescent microscopy at 10×, 20× and 40× magnification. The Pip4k2c immunostaining in human LV myocardium, which was primarily localized to both myocytes and non-myocytes, was decreased in diseased human myocardium compared to non-failed LV myocardium (FIGS. 1E-1J). As such, data show that the Pip4k2c expression was significantly reduced in CH, DCM human patients (FIG. 1K).

Example 2. Pip4k2c Expression in a Mouse Model of Human Heart Failure

To study the ramifications of decreased Pip4k2c expression observed in the diseased human myocardium of patients in Example 1, a mouse model of human heart failure was generated and analyzed to confirm comparable Pip4k2c decreased expression.

Transverse aortic constriction (TAC) is an experimental mouse model for pressure overload-induced cardiac hypertrophy and heart failure. TAC initially leads to compensated hypertrophy of the heart, which often is associated with a temporary enhancement of cardiac contractility. Over time, however, the response to the chronic hemodynamic overload becomes maladaptive, resulting in cardiac dilatation and heart failure. The murine TAC model has been extensively used as a valuable tool to mimic human cardiovascular diseases and elucidate fundamental signaling processes involved in the cardiac hypertrophic response and heart failure development. Compared to other experimental models of heart failure known to date, the TAC model provides a more reproducible model of human cardiac hypertrophy and a more gradual time course in the development of heart failure (deAlmeida et al., J Vis Exp. 2010 Apr. 21; (38), the disclosure of which is impropriated herein in its entirety).

Here, TAC was surgically performed on 8-week-old male C57BL/6j or Swiss Webster (CFW) mice (both strains purchased from Charles River Laboratories), as described in Lee et al., Nature 519, 472-476 (2015), the disclosure of which is incorporated herein in its entirety, with small adaptations. Briefly, mice received buprenorphine (0.1 mg/kg subcutaneous (s.c.) injection) 60 minutes before intubation and anesthesia with isoflurane. Thoracotomy was performed between the second and third rib, and the aortic arch was narrowed by a ligature over a 27 gauge (G) cannula. Until complete recovery from anesthesia, the mice remained in a warmed cage for 2-4 hours under direct supervision. In sham surgery, only the chest was opened, but no ligation of the aorta was carried out. Cardiac dimensions and function were analyzed by pulse-wave Doppler echocardiography, before TAC/sham surgery and before the animals were euthanized. Then, mice were sacrificed to determine parameters of cardiac hypertrophy and fibrosis and other parameters. In all experiments, the surgeon was blinded to the treatment group.

Figure 2A:
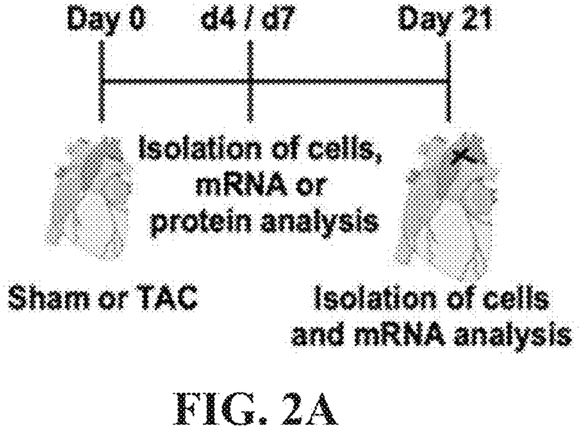
FIGS. 2A-2K include images showing decreased Pip4k2c expression in failing hearts of mice.
Figure 2B:
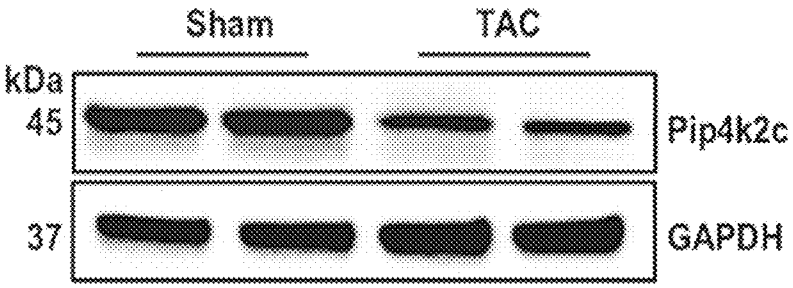
Figure 2C:
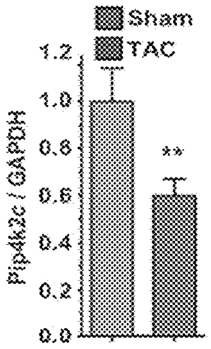
Figure 2D:
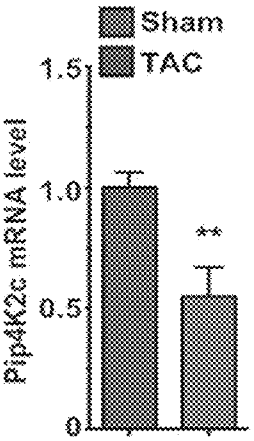

To assess mRNA and protein expression, TAC and sham-treated mice were euthanized at days 0, 4, 7, 7 and 21 and hearts were harvested from the animals (FIG. 2A). Methods to measure mRNA expression by qRT-PCR and protein expression by Western blot analysis were the same as described in Example 1. FIGS. 2B-2C show that there was a significant decrease in Pip4k2c protein levels in the hearts of TAC mice five days after surgery compared to hearts of sham-operated mice. Similarly, FIG. 2D shows that there was a significant decrease in Pip4k2c mRNA levels in the hearts of TAC mice five days after surgery compared to hearts of sham-operated mice.

To analyze the distribution of Pip4k2c in different heart cells, cardiomyocytes (CMs) and cardiac fibroblasts from both sham and TAC-operated mice were isolated at different time points (7 days and 21 days) post-operation. Mouse CMs and cardiac fibroblasts were isolated using a standard Langendorff's method as previously described in Magadum et al., Cell Res 27, 1002-1019 (2017) and Sassi et al., Nat Commun 8, 1614 (2017), the disclosures of which are incorporated herein in their entirety. Briefly, hearts were excised and the aorta was cannulated and perfused with buffer A (in mM: 113 NaCl, 4.7 KCl, 0.6 KH2PO4, 0.6 Na2HPO4, 1.2 MgSO4, 12 $NaHCO_3$, 10 KHCO3, 10 HEPES, 30 taurine). For dissociation of cells collagenase type II was included in the buffer. After dissociation the cell suspension was incubated for 10 minutes at 37° C., allowing the cardiac myocytes to sediment. Afterwards the cardiac fibroblast-enriched supernatant and the pellet were resuspended in buffer B (47.5 ml perfusion buffer A, 2.5 ml FCS, 62.5 ml, 10 μM $CaCl_2$)) and centrifuged for 5 minutes (400×g), resuspended in 5% fetal calf serum (FCS) Dulbecco's Modified Eagle's Medium (DMEM) culture medium and plated on 6 cm culture dishes for further studies. For CM and/or fibroblast count, 3 different counts/sample and 3 hearts/group were counted using a hemocytometer and averaged. The total number of CMs and/or fibroblasts counted was approximately 150-200 cells/aliquot (10 μl aliquot samples using a wide-bore pipette from the total volume of cells obtained following digestion). The cultured cells were stained with α-Actinin (CMs marker), vimentin (fibroblast marker, green) and Hoechst 33342 or DAPI for nuclei counts. For nuclei count, approximately $1\times10^3$ CMs and/or fibroblasts were counted per sample, using 3-4 independent samples per group. Nuclei count was plotted as percentage of counted CMs and/or fibroblasts (FIGS. 2F-2K).

Figure 2E:
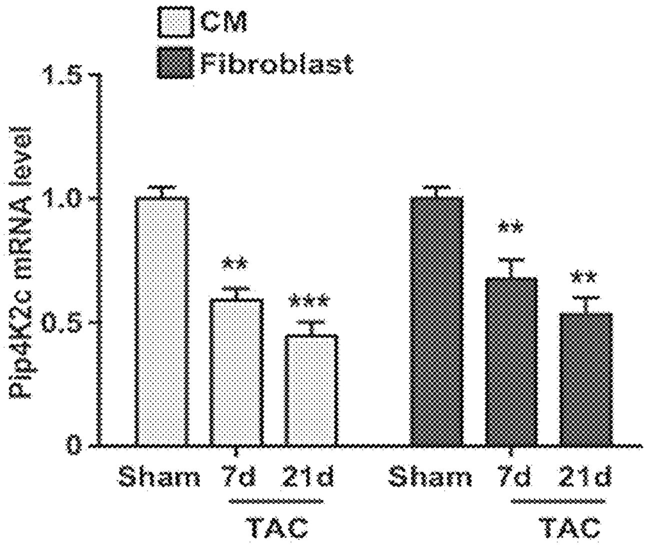
Figure 2F:
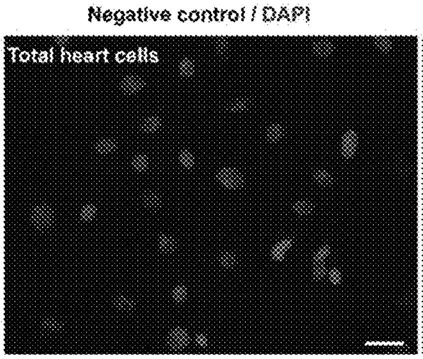
Figure 2G:
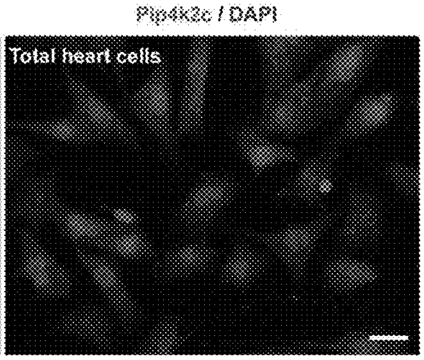
Figure 2H:
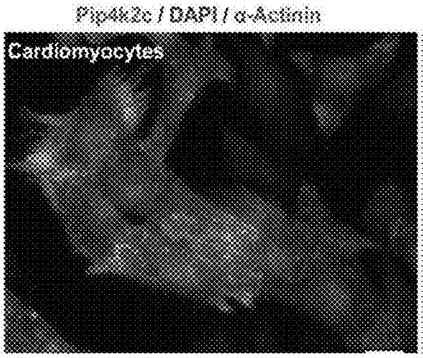
Figure 2I:
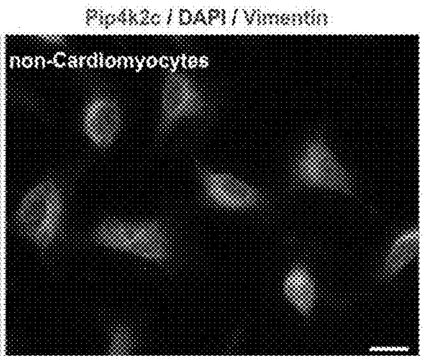
Figure 2J:
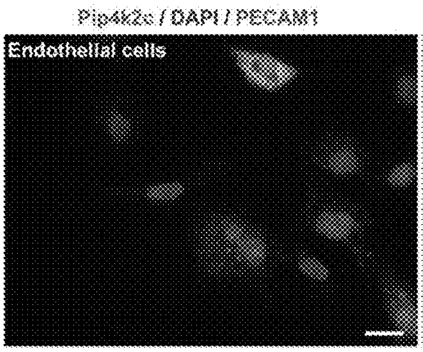
Figure 2K:
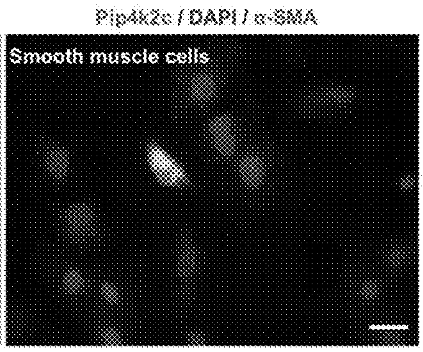

The mRNA level of Pip4k2c was measured in CMs and cardiac fibroblasts isolated from both sham and TAC-operated mice 7 days and 21 days post-operation by qRT-PCR using the method described in Example 1. As shown in FIG. 2E, mRNA levels of Pip4k2c were significantly decreased in both CMs and fibroblasts post-TAC.

The mRNA level of Pip4k2c was also measured in rat neonatal CMs (RNCMs) treated with agonist phenylephrine (PE) a drug known to induce CM hypertrophy. RNCMs from 3 day-old (P3)neonatal rats' hearts were isolated as previously described in Engel et al., Circ Res 85, 294-301 (1999) and Magadum et al., Cell Res 27, 1002-1019 (2017), the disclosures of which are incorporated herein in thier entirety. Briefly, neonatal rats' ventricular RNCMs were isolated from 4-day-old Sprague Dawley rats (Jackson) using multiple rounds of digestion with 0.14-mg/mL collagenase II. After each digestion, the supernatant was collected in horse serum. Total cell suspension was centrifuged at 300 μg for 5 minutes. Supernatants were discarded and cells were resuspended in DMEM medium with 0.1 mM ascorbic acid, 0.5% Insulin-Transferrin-Selenium (100×), penicillin (100 U/mL) and streptomycin (100 μg/mL). Cells were plated in plastic culture dishes for 90 minutes until most of the non-RNCMs attached to the dish and RNCMs remained in suspension. The RNCMs were then seeded at $1\times10^5$ cells/well in a 24-well plate. Isolated RNCMs were incubated for 48 hours in DMEM medium containing 5% horse serum plus Ara c. RNCMs were treated with phenylephrine (20 μg/ml) or DMSO for 5 days before the RNCMs were harvested for mRNA isolation and subjected to qRT-PCR to measure Pip4k2c mRNA expression (FIG. 3A). As shown in FIG. 3B, the basal Pip4k2c mRNA expression was decreased in P3 rat neonatal CMs treated with phenylephrine (PE).

Pip4k2c expression was also in isolated cultured mouse neonatal (P8) heart cells in vitro from cells isolated from mouse hearts following the method used above for RNCM isolation (FIG. 3C). After cells were in culture for 3 days, the cells were stained with α-Actinin (CMs marker), vimentin (fibroblast marker) and Hoechst 33342 or DAPI for nuclei counts. As shown in FIGS. 3D-311, Pip4k2c expression was localized to mouse CMs.

Accordingly, the data showed that Pip4k2c expression was reduced in mice heart post-TAC, much like that as observed in the CH, DCM human patients of Example 1.

Figures 4A, 4B:
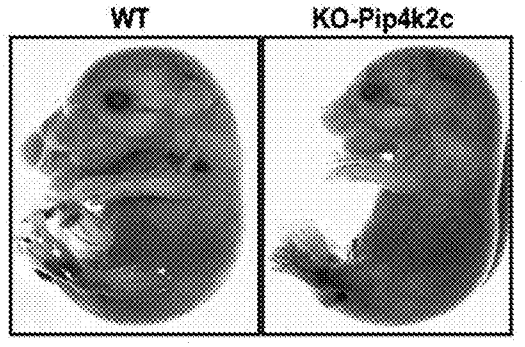
FIGS. 4A-4D show images depicting pip4k2c$^{+/+}$ littermate control (WT) or pip4k2c$^{-/-}$ (KO-Pip4k2c) mice at embryonic day 18 (E18).
Figures 4C, 4D:
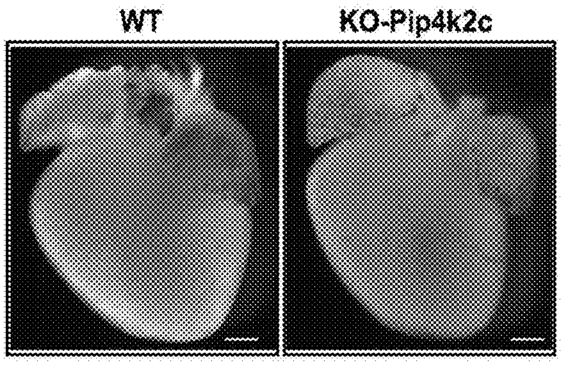
Figure 4E:
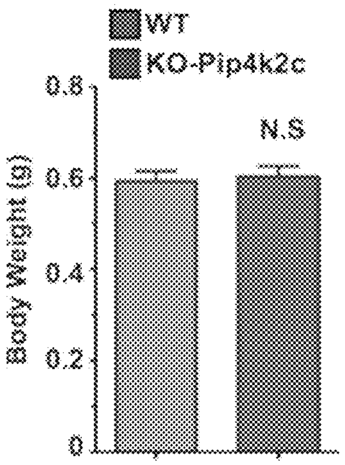
FIGS. 4E-4G show graphs depicting quantitative analyses of pip4k2c$^{+/+}$ littermate control (WT) and pip4k2c$^{-/-}$ (KO-Pip4k2c) mice at embryonic day 18 (E18). Unpaired two-tailed t-test was used to assess significance of results where N.S=Not Significant.
Figure 4F:
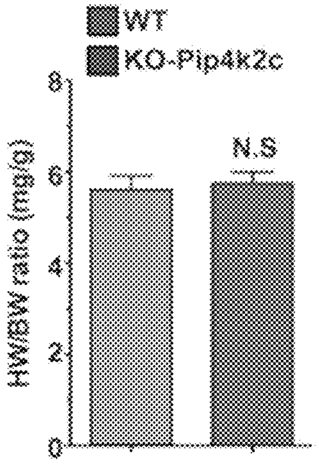
Figure 4G:
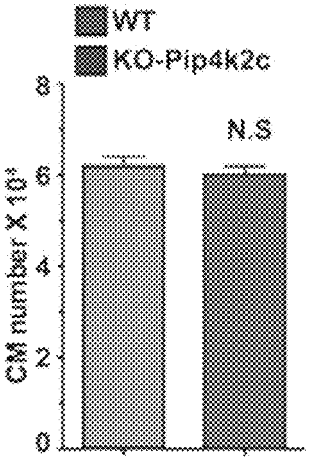

Example 3. Loss of Pip4k2c Mice Induced Cardiac Hypertrophy and Fibrosis Post TAC To study the role of Pip4k2c in the heart during development and in diseases, heart development was monitored in germline deleted Pip4k2c (Pip4k2c−/−) mice. The $Pip4k2c^{-/-}$ mice were commercially available and purchased from Jackson Laboratories ($Pip4k2c^{tm1b(KOMP)Wts\,i}$). To analyze the heart development in WT or $Pip4k2c^{-/-}$ mice, embryonic mice were harvested at E18 stage (FIGS. 4A-4B). The embryonic mice weight, heart weight was calculated and images of these mice and mice hearts were taken on a bright field microscope. The data showed that during mouse heart development, no significant change in mice viability, growth, heart weight (FIGS. 4C-4D), body weight (FIG. 4E), heart weight to body weight ratio (HW/BW) (FIG. 4F) or CM number (FIG. 4G) was observed in E18 Pip4k2c−/− mice compared to WT mice.

Figure 5G:
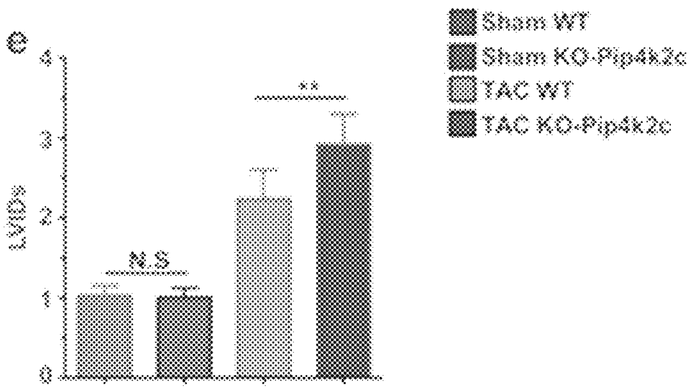
Figure 5H:
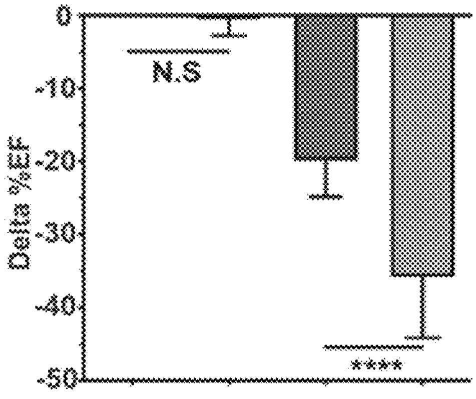

To analyze the effect of Pip4k2c on CH and fibrosis, TAC or sham surgery was performed on 8-12 week-old wild type (WT) and $Pip4k2c^{-/-}$ mice using methods described in Example 2. Cardiac function of the heart was assessed in the sham-operated WT or $Pip4k2c^{-/-}$ mice and analyzed the after 21 days. Briefly, the dimensions and function of the left ventricle was evaluated by performing transthoracic two-dimensional echocardiography (ECHO). Mice underwent echography onsite with a GE Cares machine (V7R5049) equipped with a 40 MHz mouse ultrasound probe. Mice were anesthetized with a mixture of 1-2% isoflurane in air, and imaging was performed on days 2 and 28 post LAD ligation. The ejection fraction and fractional shortening were calculated as percentages from the diastolic volume (EDV) and end systolic volume (ESV) dimensions on an M-mode ultrasound scan. The following formulas were used: % ejection fraction=(EDV-ESV)/EDV*100, and % fractional shortening=(left ventricular internal dimension at end-diastole (LVIDd)—left ventricular internal dimension at end-systolic (LVIDs))/LVIDd*100. Echocardiograms were performed on 4-10 nine hearts/treatment group (FIGS. 5A-5D). Data showed that $Pip4k2c^{-/-}$ mice had deteriorated cardiac function 21 days post-TAC compared to WT mice. The percentage of ejection fraction (% EF) and fractional shortening (% FS) were reduced significantly in $Pip4k2c^{-/-}$ mice post TAC, but there is no significant change in sham-operated WT and $Pip4k2c^{-/-}$ mice (FIGS. 5E and 5H). The left ventricular internal diameter end-systole (LVIDs) and left ventricular internal diameter end-diastole (LVIDd) were significantly increased in $Pip4k2c^{-/-}$ mice post-TAC (FIGS. 5F-5G).

The heart weight/Tibia length (TL) of $Pip4k2c^{-/-}$ mice post-TAC were increased significantly compared to WT TAC mice or sham-operated WT/$Pip4k2c^{-/-}$ mice (FIG. 6A) and the hearts of $Pip4k2c^{-/-}$ mice post TAC were larger than those of WT mice (FIGS. 6B-6E). Measuring the heart-weight to tibia length ratio was done using a standard scale at the end point of each experiment. This ratio was calculated as the heart tissue weight relative to the mouse tibia length-weight in grams (mg) and length in mm.

Hematoxylin and eosin (H&E) staining was also performed to assess gross morphology changes in WT and $Pip4k2c^{-/-}$ mice post-TAC. To assess heart histology, hearts were excised, briefly washed in PBS, perfused with perfusion buffer, weighed and fixed in 4% PFA (paraformaldehyde) at 4° C. overnight. The next day, hearts were washed with PBS and incubated overnight in 30% sucrose. Next, hearts were put in optimal cutting temperature compound (OCT compound), frozen and stored at −80° C. The heart blocks were sectioned transverse or longitudinal at 8-9 μm using a cryostat. The slides were further processed for evaluation using immunostaining (see Example 1) or histological staining using hematoxylin and eosin (H&E) and Sirius red/fast green staining. For H&E staining, the OCT frozen longitudinal heart sections were dried for 30 minutes to 1 hour at room temperature then hydrated in PBS for 10 minutes. The slides were kept in Hematoxylin stain for 2 minutes and washed with tap water for 5 minutes. Next the sections were then placed in eosin solution for 1 minute and washed with tap water for 5 minutes. The slides were transferred to PBS for 5 minutes. Next sections were dehydrated in 100% ethanol for a minute and xylene for 1 minute. Finally, sections were mounted under a coverslip with VectorShield and images were taken on bright field microscope. As shown in FIGS. 6F-6I, the H&E staining of these hearts showed there was no significant change in Pip4k2c$^{-/-}$ sham-operated mice while after TAC induction whereas Pip4k2c$^{-/-}$ mice hearts were larger with significant larger chamber size.

Next, the CM size in the heart sections of WT and Pip4k2c$^{-/-}$ mice post-TAC were measured by wheat germ agglutinin (WGA) staining. Briefly, cryo-frozen heart sections were dried for 30-60 minutes at room temperature and dehydrated with PBS for 10 minutes. Next WGA (50 μm) was applied for a 1 hour. The sections were washed three times with PBS for 5 minutes each and mounting medium was applied. For CM size quantification, images at 20× or 40× magnification were captured and the ImageJ program was used to determine the area of each cell. Quantitative analyses involved counting multiple fields from 3-6 independent hearts/group, and 3 sections/heart (~50 cells per field assessed, to a total ~250 cells per sample). Images showed that there was no significant change in CM size in sham-operated Pip4k2c$^{-/-}$ and WT mice (FIGS. 7A-7C); however, CM size but was increased significantly in Pip4k2c$^{-/-}$ mice 21 days post-TAC (FIGS. 7D-7E).

Figure 8A:
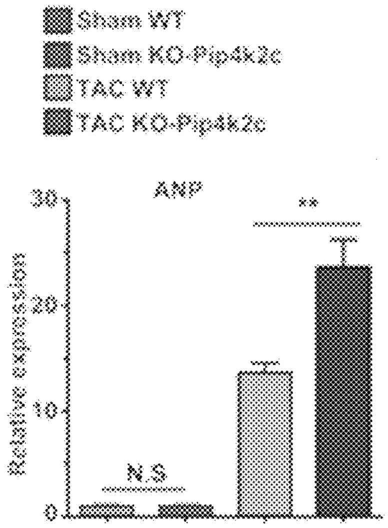
FIGS. 8A-8E show graphs depicting quantification of mRNA expression of various genes in hearts of pip4k2c$^{+/+}$ littermate control (WT) mice and pip4k2c$^{-/-}$ (KO-Pip4k2c) mice after 21 days post Sham or TAC injury using qRT-PCR.
Figure 8B:
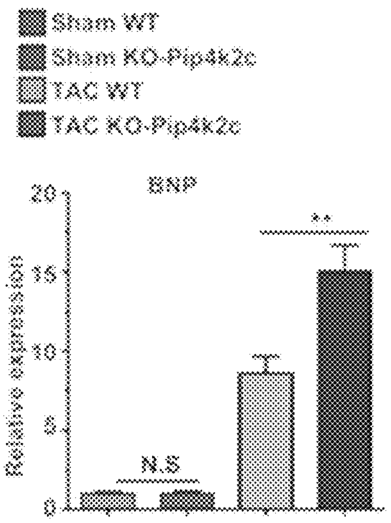
Figure 8C:
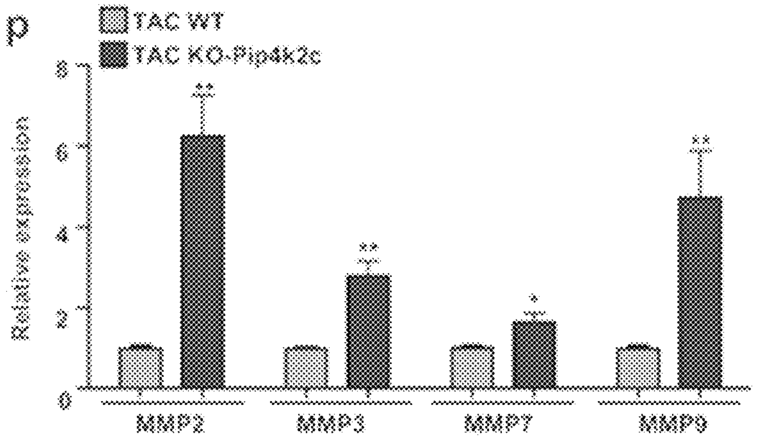
Figure 8E:
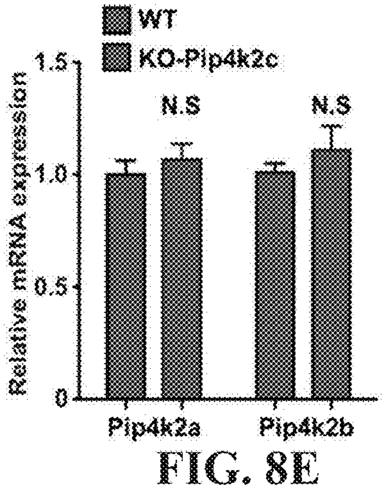
Figure 8D:
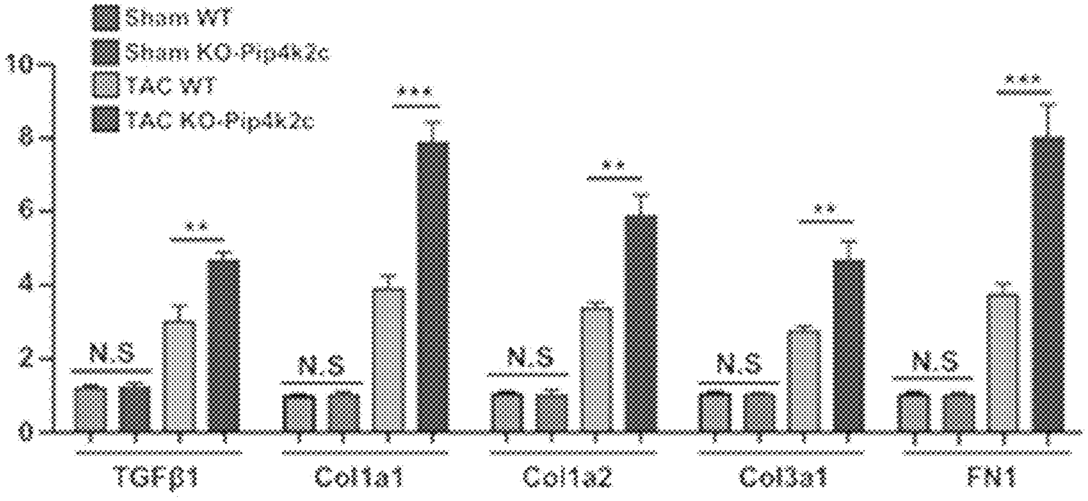

The mRNA expression for hypertrophic markers (atrial natriuretic peptide (ANP) and B-type natriuretic peptide (BNP)), fibrosis markers (Col1a1 (collagen, type I, alpha 1), Col1a2 (collagen, type I, alpha 2), and Col3a1 (collagen, type III, alpha 1)), extracellular matrix proteins (FN1 (Fibronectin 1)), TGFβ1 (transforming growth factor beta 1) and metalloproteinases (MMP2, MMP3, MMP7, and MMP9) were measured in hearts of WT and Pip4k2c$^{-/-}$ mice post-TAC using the qRT-PCR method described in Example 1. Expression of both ANP and BNP were increased in Pip4k2c$^{-/-}$ mice post-TAC compared to the WT TAC model and sham-operated WT or Pip4k2c mice (FIGS. 8A-8B). This suggested the deletion of Pip4k2c post-TAC induced cardiac hypertrophy. The mRNA expression of fibrosis marker (Col1a1, Col1a2, and Col3a1), extracellular matrix proteins (FN1), TGFβ1, and metalloproteinases (MMP2, MMP3, MMP7, and MMP9) were all significantly increased in Pip4k2c$^{-/-}$ mice post-TAC (FIGS. 8C-8D). Importantly, Pip4k2c deletion did not significantly change the expression of other Pip4k2s (Pip4k2a and Pip4k2b) in the heart (FIG. 8E).

Next, fibrosis in hearts of WT and Pip4k2c$^{-/-}$ mice post-TAC was assessed by immunostaining heart sections for Sirius red/Fast green. Briefly, cryo-frozen heart sections were dried for 1 hour at room temperature and incubated with Bouin's solution at 58° C. for 1 hour. Sections were then washed with tap water for 5 minutes to remove yellow color from sections. The sections were stained with 0.1% fast green for 20 minutes at room temperature and rinsed in 1% acetic acid for 1 minute at room temperature. Next slides were washed with tap water for 5 minutes. The sections were further stained with 0.1% Sirius red for 30 minutes at room temperature. Then slides were dehydrated sequentially by 70% ethanol for 30 seconds, 100% ethanol for 1 minutes and 100% xylene for 3 minutes. The slides were covered with coverslips using permount-mounting medium. Images were taken on bright field microscope. As shown in FIGS. 9A-9K, there was a significant increase in fibrosis in Pip4k2c$^{-/-}$ mice compared to WT mice post-TAC; while there is no significant change in sham operates WT or Pip4k2c$^{-/-}$ mice. Importantly the survival rate was significantly decreased for Pip4k2c$^{-/-}$ mice post-TAC compared to other treated groups (FIG. 10). FACS analysis of immune cell distribution in KO-Pip4k2c or WT hearts 21 days post MI showed no significant differences in immune cells infiltration into the heart (FIGS. 31A-31E).

Figure 11E:
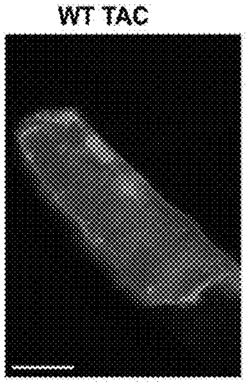
FIGS. 11E-11G depict images of the evaluation of CM size (cross-sectional area) in cardiomyocytes (CMs) isolated from the hearts of pip4k2c$^{+/+}$ littermate control (WT) mice 21 days post TAC injury (WT TAC) and pip4k2c$^{-/-}$ (KO-Pip4k2c) mice 21 days post TAC injury (KO-Pip4k2c TAC).
Figure 11F:
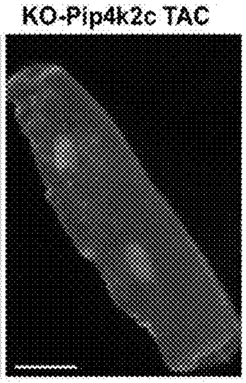
Figure 11G:
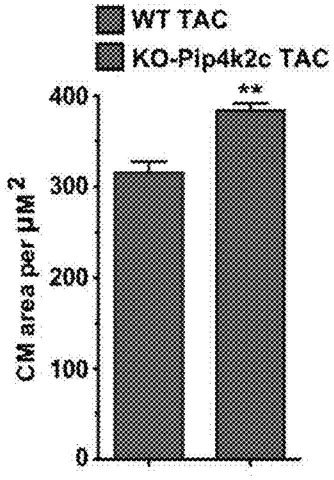
Figure 11H:
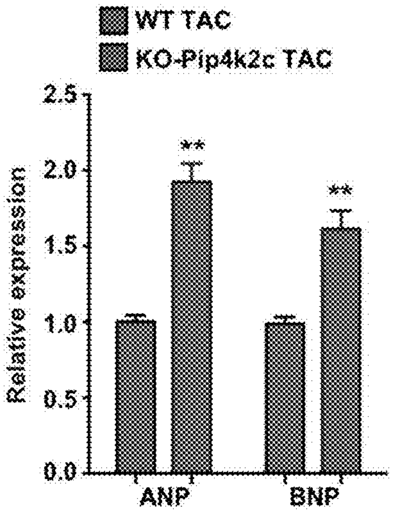
FIG. 11H shows a graph depicting quantification of mRNA expression of the hypertrophic markers ANP and BNP in in cardiomyocytes (CMs) isolated from the hearts of pip4k2c$^{+/+}$ littermate control (WT) mice 21 days post TAC injury (WT TAC) and pip4k2c$^{-/-}$ (KO-Pip4k2c) mice 21 days post TAC injury (KO-Pip4k2c TAC) as measured by qR_T-PCR. Unpaired two-tailed t-test was used to measure significance where n=3 for all experimental groups and **=P<0.01.

To examine the effect of lack of Pip4k2c expression in CMs following TAC injury, CMS were isolated rom from pip4k2c+/+ littermate control (WT) or pip4k2c−/− (KO-Pip4k2c) mice heart 21 days post TAC injury following methods described in the examples herein. FIGS. 11A-11D show isolated mouse CMs immunostained for the CM sarcomeric structural proteins α-Actinin and Troponin T. CM size (cross-sectional area) of the isolated CMs was evaluated by immunostaining with WGA according to methods described in other examples herein (FIGS. 11E-11F). Quantitative analysis of WGA stained sections showed that CM area was increased in isolated CMs from pip4k2c−/− mice post TAC compared to CMs isolated from WT mice post TAC (FIG. 11G). Isolated CMs harvested from WT and pip4k2c−/− mice post TAC were subjected to qRT-PCR using methods disclosed in Example 1 to assess mRNA expression levels of the hyperertrophic markers ANP and BNP. FIG. 11H shows that expression of both ANP and BNP was significantly increased in CMs isolated from pip4k2c−/− mice post TAC compared to Cms isolated from WT mice post TAC.

Taken together, data suggest that the deletion of Pip4k2c during development did not have any significant effect on heart development, but after TAC in Pip4k2c$^{-/-}$ adult mice, there was induced CH and fibrosis resulted into deteriorated cardiac function causing 70% of mice to die by 21 days post-TAC.

Example 4. Pip4k2c modRNA Expression in Heart Reversed the Cardiac Hypertrophy and Fibrosis in the TAC Mice Model The modRNA is a novel gene expression tool and is chemically synthesized in vitro with 100% replacement of Uridine by N1-Methylpseudouridine-5'-Triphosphate (1-mψU) that results in lower immunogenicity, higher RNase resistance, and more efficient translation compared to unmodified mRNA in cells and tissue (Kariko et al. Mol Ther 16, 1833-1840 (2008), the disclosure of which is incorporated herein in its entirety). The protein expression starts in minutes, peaks in 12 to 48 hours and lasts up to 8-12 days in in vitro and in mice hearts (Zangi et al., Nat Biotechnol 31, 898-907 (2013); Zangi et al., Circulation 135, 59-72 (2017); Magadum et al., Mol Ther Nucleic Acids 13, 133-143 (2018), the disclosures of which are incorporated in therie entireity).

To see the effect of Pip4k2c overexpression on cardiac fibrosis and hypertrophy in TAC mice model, chemically modified Pip4k2c modRNA was first generated. ModRNAs were transcribed in vitro from plasmid templates (see complete list of open reading frame sequences used to make the modRNA in Table 2) Using a customized ribonucleotide blend of anti-reverse cap analog, 3-O-Me-m7G (5')ppp(5')G (6 mM, TriLink Biotechnologies), guanosine triphosphate (1.5 mM, Life Technology), adenosine triphosphate (7.5 mM, Life Technology), cytidine triphosphate (7.5 mM, Life Technology) and N1-Methylpseudouridine-5'-Triphosphate (7.5 mM, TriLink Biotechnologies) as described previously in Kondrat et al., METHODS MOL BIOL 1521, 127-138 (2017), the disclosure of which is incportated herein in its entireety.

TABLE 2

Open reading frame sequences used for modRNA production.

| Gene | Open Reading Frame |
|---|---|
| Pip4k2c | atgacggctgcgcaggtgagcaccgcttccgggtcgggcttcggagtcgcggctag<br>ctcccgcttccactcgctcgggtgcgcgggagactatggcgtcctcctccgtccct<br>cccgccaccgcacccgcggcagctggaggccccggcccgggattcggcttcgcctc<br>caaaaccaagaagaagcatttcgtacagcagaaagtgaaggtgttccgggccgcgg<br>acccgctggtgggcgtgttcctgtggggcgtcgctcactcgatcaatgagctcagc<br>caggtaccgcccccagtgatgttgctgccagatgactttaaagccagctccaagat<br>caaggtcaacaatcactttttccatagagaaaatcttcccagtcatttcaagttca<br>aggagtattgtccccaggtcttcaggaacctgagagatcggtttgccatcgatgat<br>cacgattacttggtgtcccttactcgaagcccccccaagcgaaactgaaggcagtga<br>tggccgtttccttatctcctatgaccgcactctggtcatcaaggaagtgtcgagcg<br>aagatattgcggatatgcacagcaacctctccaactaccaccagtacatagtgaaa<br>tgtcatggcaacacgcttctgccccagttcctgggcatgtaccgagtcagtgtaga<br>aaatgaagacagctacatgctcgtgatgcgcaatatgtttagtcatcgtcttcctg<br>tgcataggaagtatgacctcaagggctctctagtgtcccgggaagccagcgataag<br>gaaaaggttaaagaactgccaacactaaaggatatggactttcttaacaagaacca<br>gaaagtgtatattggtgaagaagaaaagaaagtattcctggagaagctgaagcgag<br>atgtggagtttctagtgcagctgaagatcatggactacagcctcctgttgggcatc<br>cacgacatcatccggggctctgaacccgaggaagaggggcctgtgagggaggagga<br>gtctgagtgggatggggactgtaacctggctggacctcccgccctggtgggctcct<br>atggtacctcccctgagggtatcggaggctacatccattcccaccggccactgggc<br>ccaggagagtttgagtccttcatcgatgtctatgctatccggagtgcggaggggggc<br>cccccagaaggaggtgtatttcatgggcctcattgacattctgacacagtatgatg<br>ccaagaagaaagcagctcatgcagccaagactgtcaagcacggggcgggggcagag<br>atctccactgtccatcctgagcagtatgctaagcgattcctggactttattgccaa<br>catctttgcctaagaggctgcctgactccagggtgattgcggctttatgttggagg<br>tggcgggttctgagaggcttaggggagctggacttggccgttacttctcttctttg<br>ctaaattcaggctgcaggctccttccatccaaataacttccttctggtggataggg<br>ttttctcgcccaccccagacatacactgtcctttctccccttgtccatttctctgc<br>cctccctccttgctcccagtaagccctcctgcttctttagagtgttattgtcgact<br>cttctaagtgccttgatctttgaaaaatatcttgtttctatgaaataggaggagct<br>gggggaggggttgtttgccatcttcgggacctgactgaacagtggacttggctcaa<br>gcaactgcctggatgcacttttgctgagtggaagaaactgaatgtctggattttgc<br>tgatacttttatggggcactttgtggcatgcttcctccctggtaagccctggaatg<br>gagggctttcaggatgctccagatgtgggtgcaggcattcacacatggacagtctg<br>gcctggaggtcaggtggggagtggtcagcaggctggcacctcacaaggcaggacct<br>aagcctaagcggacttttgtgactatgcagatgatggagaaggtccctgtggagca<br>acgactgttcccgactgttcccgttctcccaccccaccccaccccacgtccacctc<br>tttctgtgagcactttgggtgcaggagcccagaggctagcggtgcccgagcttagg<br>tgcaggtgtgagactcgggctgctcttcccacaaccctgtgccttgctggtgagca<br>gggagagcagtagaggccgggacaggtcggagtgcagggttcattgcctgggtgac<br>accctttcttcctgtctcactactcctgggcttctttctagcagaggggaacagta<br>ccatctccataatttggggaggatagagctctcgagtgaaggagcctccgcatccc<br>tggggcatgtgtacctagaactcccccttccttctcaaaaccctttctggttggagt<br>tgttattctgtcccatcttccactgctaatgtgtctcccaggggacagatggcctt<br>ctttgtcatctcccctctccgcccccagagaggagtcagagccataactcaatcca<br>cccagtcctctccaaagacagctgaatattaatgcacgccatcctcagaatggaga<br>ggacctgctaggcatcttagctctcccagctcgtgcctgtaaagccagcactcagg<br>aggctctgagagttcaagtccagcctgggctactgagtgagacctggtctcaggaa<br>cactccaaataggtttgggtttgagcgctggagatcatagctgagttggtagtgtg<br>cttgcctagcatgtacaaagctctgggatccacccccagcaccacttaagccaggc<br>gtggcggtgcacgcctgcactcctggccctgggaagtagtggtaagcaggatgggg<br>cattcaaggtcatcgccagttagttacttgacgaggttgaggccagccaaggaaac<br>aggagaccatcttggggaaaatgattctaaggagagatagattgtctttgtctctg<br>cctaaagcctttggaagcaagccactcatcttcgctgtttggcgctctggaggtgg<br>ggtgggcattgaaggcaaggagctgctttgctgtgtgtccatgaggtcctcaggga<br>gaagcccacctccctcaccaaaggaagcagcaagatgggtgcccggttggggtggg<br>tgggacctgctgagtctcccatccctcaagcaacctttcccctgttgaatgcaata<br>agtgactccggtcccttaacaactggggtctcaccgtgcggctgtggtcgtgggca<br>gtgttgccatcttcacttactgcttccgttttccatctgttttgttaataaaatat<br>gtatatttactcccgatatcacaataaaataaattatttgatctaagtca (SEQ<br>ID NO: 36) |
| Luciferase<br>(Luc) | atggccgatgctaagaacattaagaagggccctgctcccttctaccctctggagga<br>tggcaccgctggcgagcagctgcacaaggccatgaagaggtatgccctggtgcctg<br>gcaccattgccttcaccgatgcccacattgaggtggacatcacctatgccgagtac<br>ttcgagatgtctgtgcgcctggccgaggccatgaagaggtacggcctgaacaccaa<br>ccaccgcatcgtggtgtgctctgagaactctctgcagttcttcatgccagtgctgg<br>gcgccctgttcatcggagtggccgtggcccctgctaacgacatttacaacgagcgc<br>gagctgctgaacagcatgggcatttctcagcctaccgtggtgttcgtgtctaagaa<br>gggcctgcagaagatcctgaacgtgcagaagaagctgcctatcatccagaagatca<br>tcatcatggactctaagaccgactaccagggcttccagagcatgtacacattcgtg<br>acatctcatctgcctcctggcttcaacgagtacgacttcgtgccagagtctttcga<br>cagggacaaaaccattgccctgatcatgaacagctctgggtctaccggcctgccta<br>agggcgtggccctgcctcatcgcaccgcctgtgtgcgcttctctcacgcccgcgac<br>cctattttcggcaaccagatcatccccgacaccgctattctgagcgtggtgccatt<br>ccaccacggcttcggcatgttcaccaccctgggctacctgatttgcggctttcggg |

TABLE 2-continued

Open reading frame sequences used for modRNA production.

| Gene | Open Reading Frame |
|---|---|
| | tggtgctgatgtaccgcttcgaggaggagctgttcctgcgcagcctgcaagactac<br>aaaattcagtctgccctgctggtgccaaccctgttcagcttcttcgctaagagcac<br>cctgatcgacaagtacgacctgtctaacctgcacgagattgcctctggcggcgccc<br>cactgtctaaggaggtgggcgaagccgtggccaagcgctttcatctgccaggcatc<br>cgccagggctacggcctgaccgagacaaccagcgccattctgattaccccagaggg<br>cgacgacaagcctggcgccgtgggcaaggtggtgccattcttcgaggccaaggtgg<br>tggacctggacaccggcaagaccctgggagtgaaccagcgcggcgagctgtgtgtg<br>cgcggccctatgattatgtccggctacgtgaataaccctgaggccacaaacgccct<br>gatcgacaaggacggctggctgcactctggcgacattgcctactgggacgaggacg<br>agcacttcttcatcgtggaccgcctgaagtctctgatcaagtacaagggctaccag<br>gtggccccagccgagctggagtctatcctgctgcagcaccctaacattttcgacgc<br>cggagtggccggcctgcccgacgacgatgccggcgagctgcctgccgccgtcgtcg<br>tgctggaacacggcaagaccatgaccgagaaggagatcgtggactatgtggccagc<br>caggtgacaaccgccaagaagctgcgcggcggagtggtgttcgtggacgaggtgcc<br>caagggcctgaccggcaagctggacgcccgcaagatccgcgagatcctgatcaagg<br>ctaagaaaggcggcaagatcgccgtgtaa (SEQ ID NO: 37) |

The mRNA was purified using the Megaclear kit (Life Technology) and treated with antarctic phosphatase (New England Biolabs), followed by re-purification using the Megaclear kit. The mRNA was quantitated by Nanodrop (Thermo Scientific), precipitated with ethanol and ammonium acetate and resuspended in 10 mM TrisHCl, 1 mM EDTA.

Figure 12A:
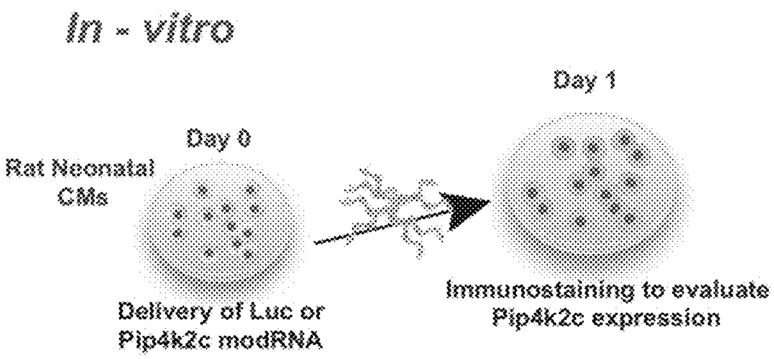
FIGS. 12A-12B depict schematics of the experimental plan to evaluate using qPCR Pip4k2c expression in P3 rat neonatal CMs treated with phenylephrine (PE) or DMSO, in vitro (FIG. 12A) and the experimental plan to evaluate Pip4k2c expression in isolated cultured mouse neonatal (P8) heart cells (FIG. 12B).
Figure 12B:
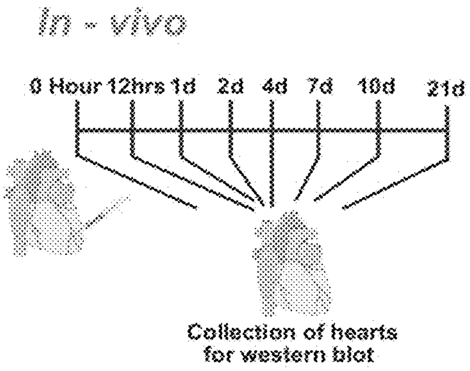
Figures 12C, 12D:
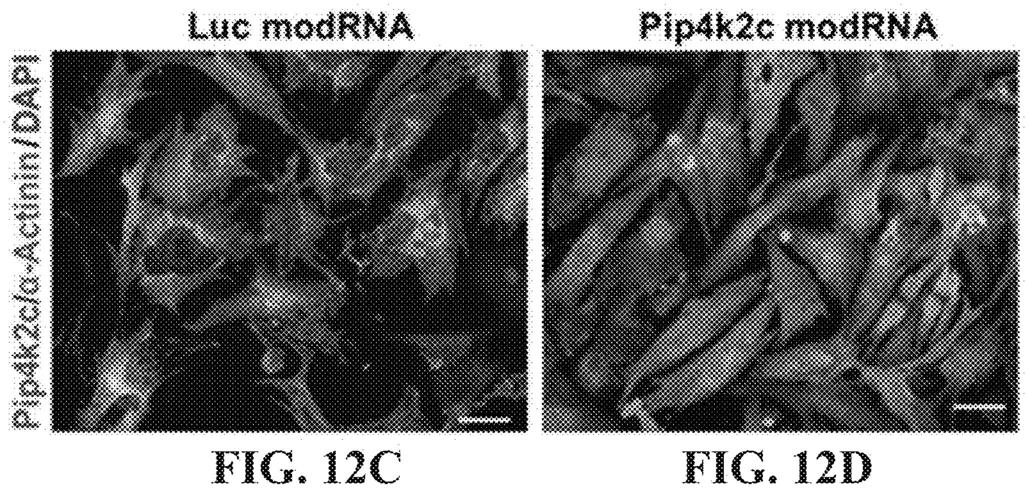
FIGS. 12C-12D depict images of pip4k2c (red) expression in P3 neonatal rat CMs post-delivery of luciferase (Luc; control) (FIG. 12C) or Pip4k2c modRNA (FIG. 12D), co-stained with α-actinin (CM-marker, green) and DAPI, (nuclei, blue). Scale bar=50 μm.
Figure 13A:
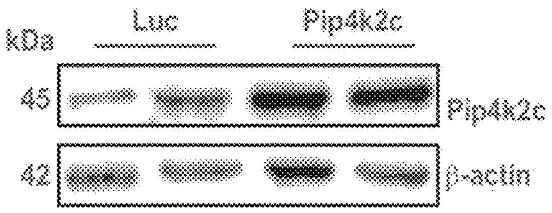
FIGS. 13A-13D depict images of Western blot analysis of Pip4k2c expression post modRNA delivery in vivo.
Figure 13B:
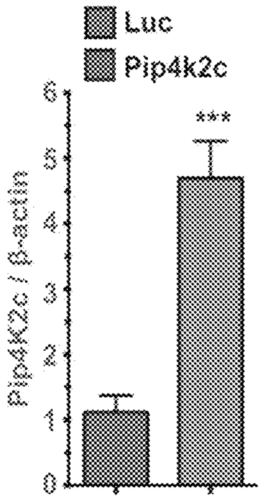
Figure 13C:
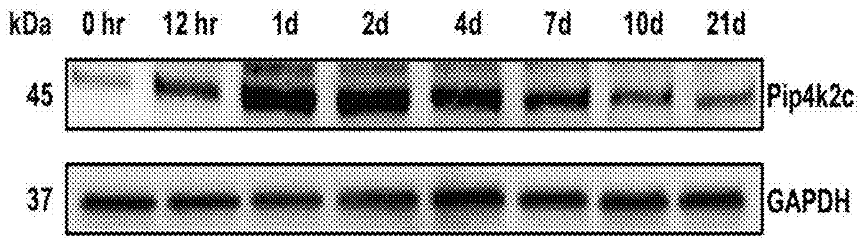
Figure 13D:
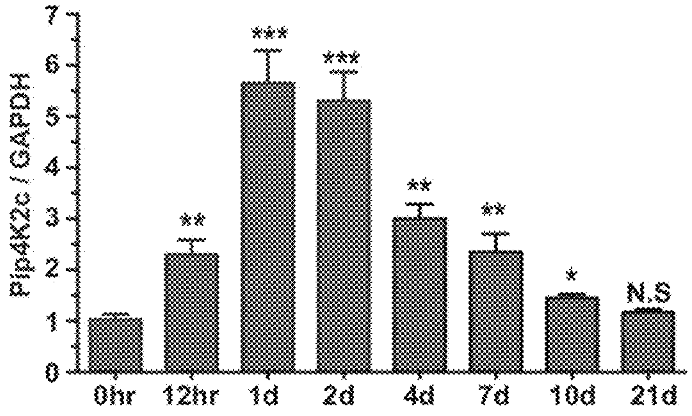

Prepared chemically modified Pip4k2c modRNA was expressed in vitro (FIG. 12A) as well as in vivo (FIG. 12B). In vivo modRNA transfection was done, as described previously in Sultana et al., Mol Ther 25, 1306-1315 (2017). Briefly, using sucrose citrate buffer containing 20 μl of sucrose in nuclease-free water (0.3 μg/ml), with 20 μl of citrate (0.1 M pH=7) mixed with 20 μl of different concentrations of modRNA in saline to a total volume of 60 μl. The transfection mixture was directly injected (3 individual injections, 20 μl each) into the myocardium. For in vitro transfection, RNAiMAX transfection reagent (Life Technologies) was used according to manufacturer's recommendation. FIGS. 12C-12D show increased expression of Pip4k2c in rat CMs following Pip4k2c modRNA in vitro transfection compared to transfection with control luciferase (Luc) modRNA.

Figure 14A:
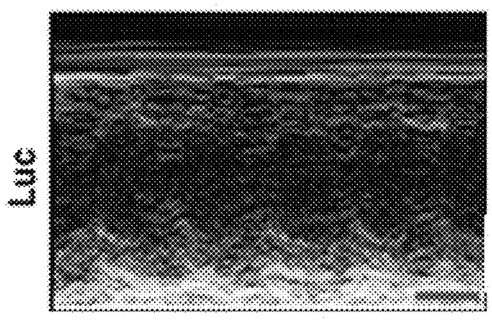
FIGS. 14A-14K depict images showing Pip4k2c modRNA elevation of Pip4k2c levels and attenuation of cardiac hypertrophy and fibrosis post TAC injury.
Figure 14B:
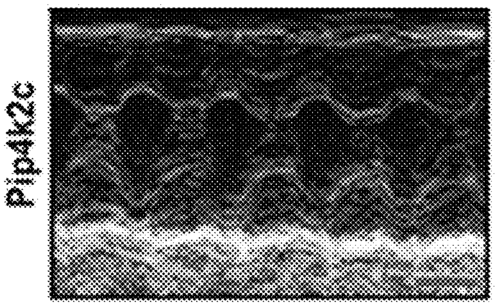
Figure 14C:
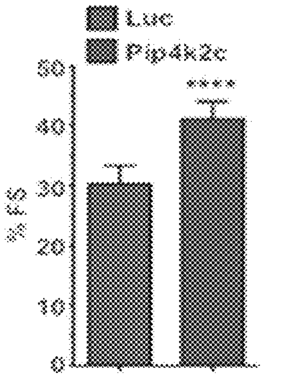
Figure 14D:
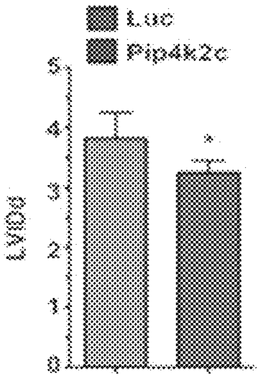
Figure 14E:
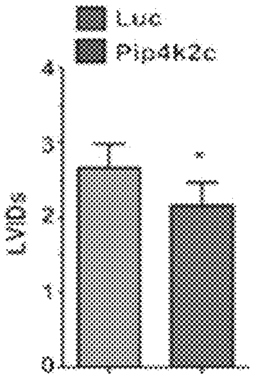
Figure 14F:
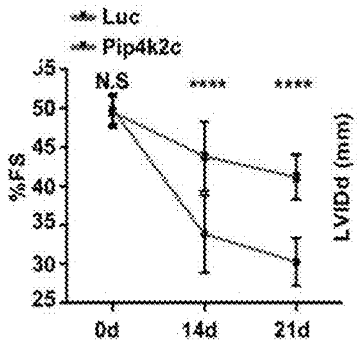
Figure 14G:
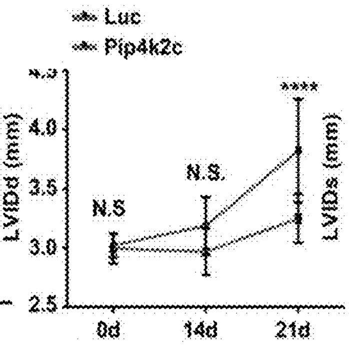
Figure 14H:
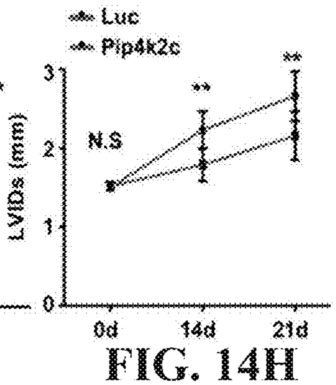
Figure 14I:
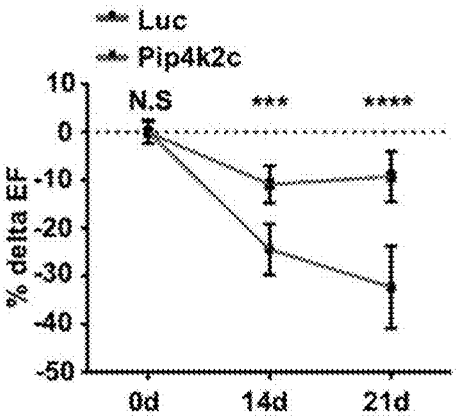
Figure 14J:
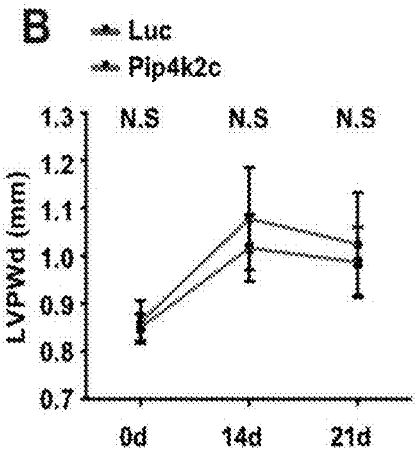
Figure 14K:
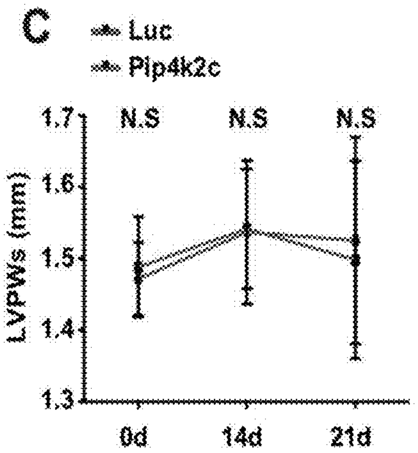
Figure 32A:
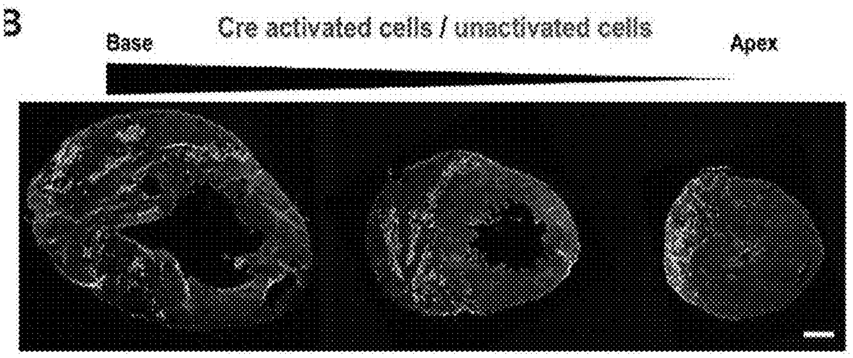
FIGS. 32A and 32B depict images showing biodistribution of modRNA transfection in TAC mouse model.
Figure 32B:
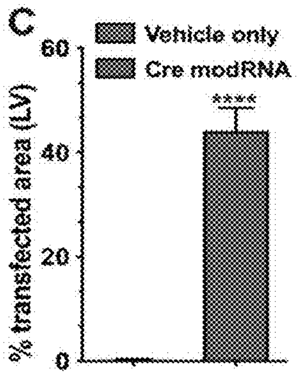

Luciferase (Luc) or Pip4k2c modRNA was injected after TAC operation in WT mice and protein Pip4k2c in the heart was measured 24 hours after modRNA injection. Cre recombinase (Cre) modRNA and mTmG mice were used to evaluate the biodistribution of modRNA in the mouse heart post TAC. FIGS. 32A-32B show that modRNA-delivered Cre led to more than 40% transfection of the LV in a TAC model. Using Western blot analysis as described in Example 1, a significant increase in Pip4k2c protein expression was observed (FIGS. 13A-13D). After 21 days of luc or Pip4k2c modRNA injection, cardiac function was analyzed using ECHO as described in Example 3 (FIGS. 14A-14B). The percentage of delta % left ventricular ejection fraction and fractioning shorting was improved significantly in Pip4k2c modRNA injected mice compared to luc in post-TAC mice (FIGS. 14C. 14F, and 14I). Interestingly, neither diastolic nor systolic left ventricular posterior wall diameter significantly changed (FIGS. 14J and 14K). The LVIDd and LVIDs were significantly improved in Pip4k2c modRNA injected mice post-TAC (FIGS. 14D-14E and 14H-14H). Also, there was a decrease in heart size 21 days post-TAC in Pip4k2c modRNA injected mice, suggesting reduction of CH (FIGS. 15A-15B). The HW/TL of Pip4k2c modRNA injected mice post-TAC was decreased significantly (FIG. 15C). The WGA staining of heart sections, performed as described in previous examples, showed a significant decrease in CM size in Pip4k2c modRNA injected mice (FIGS. 16A-16C).

Figure 17A:
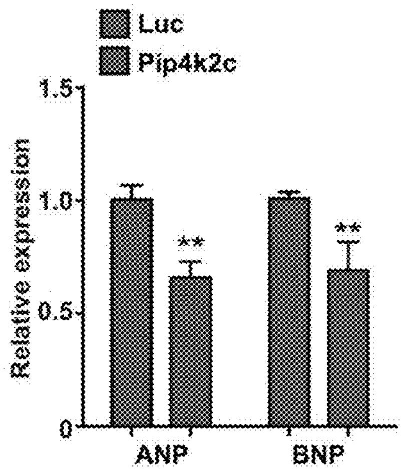
FIGS. 17A-17C show a graph depicting quantification of mRNA expression of various genes in hearts of wild type (WT) mice 21 days post TAC injury and delivery of luciferase (Luc) modRNA or Pip4k2c modRNA. Unpaired two-tailed t-test was used to measure significance where n=8 for all experimental groups and *=P<0.001, =P<0.01, *=P<0.05, and N.S, Not Significant.
Figure 17B:
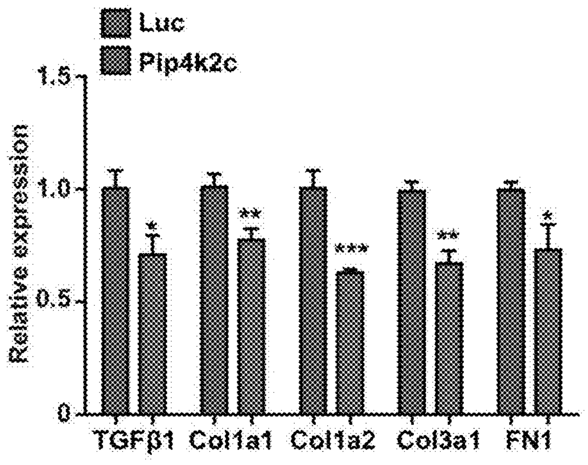
Figure 17C:
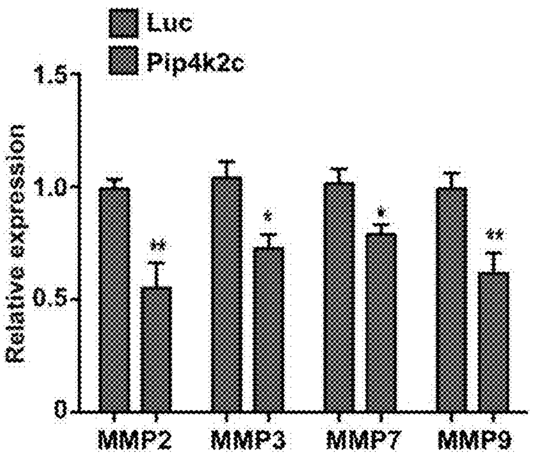
Figures 21A, 21B, 21C:
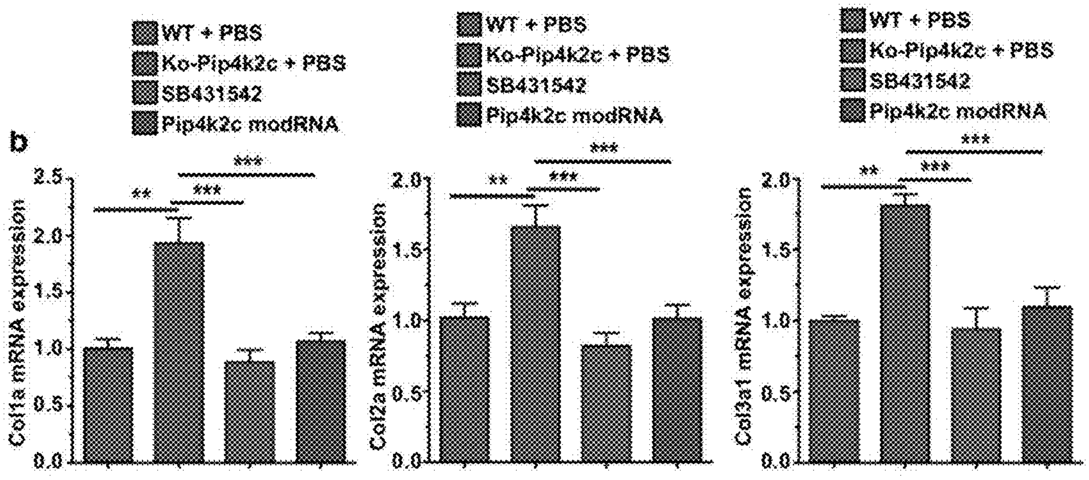
FIGS. 21A-21E show a graphs depicting quantification of mRNA expression of various genes in cardiac fibroblasts isolated from the hearts of pip4k2c$^{+/+}$ littermate control (WT) and pip4k2c$^{-/-}$ (KO-Pip4k2c) 21 days post TAC injury that were then subjected to a 5 day treatment with PBS (control), the TGF-β inhibitor (SB431542), or Pip4k2c modRNA. One-way ANOVA was used to measure significance where n=3 for all experimental groups and *=P<0.001, =P<0.01, *=P<0.05, and N.S=Not Significant.
Figures 21D, 21E:
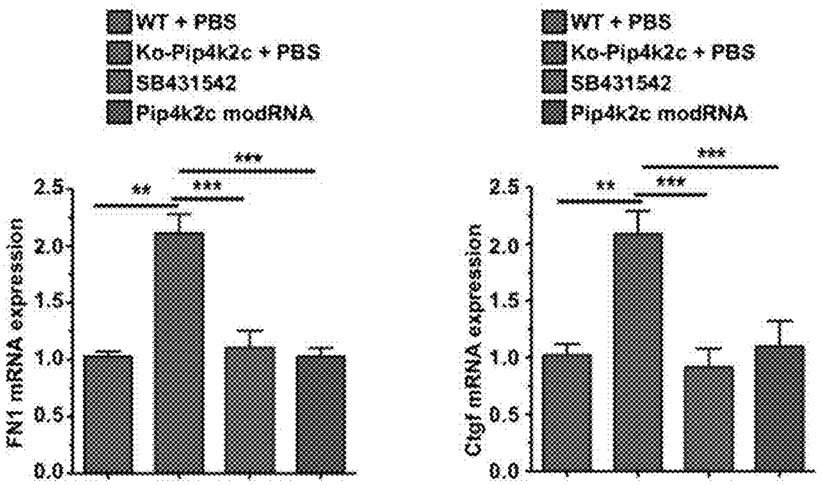

The mRNA expression (as measured by qRT-PCR, described in Example 1) for CH markers like ANP and BNP were decreased significantly (FIG. 17A). These results confirm that the overexpression of Pip4k2c modRNA post-TAC reverses cardiac hypertrophy. The mRNA expression of Col1a1, Col1a2, Col3a1, FN1, MMP2, MMP3, MMP7, and MMP9 were also significantly decreased (FIGS. 17B-17C). Importantly, there was a significant down-regulation of TGF-0, a master regulator fibrosis (FIG. 17B). Sirius red/fast green was performed as described in examples above to evaluate the fibrotic area 21 days post TAC injury and delivery of Luc or Pip4k2c modRNA. As shown FIGS. 18A-18C, this analysis of fibrosis in luc or Pip4k2c modRNA injected mice post-TAC found that the fibrosis area was significantly decreased in Pip4k2c modRNA injected mice. Further, the survival rate of Pip4k2c modRNA injected mice was significantly improved 21 days post-TAC (100% survival compared to 60% survival in luc injected mice) (FIG. 19).

To study the dynamics of fibroblast proliferation and fibrosis, fibroblasts were isolated from the heart of WT or Pip4k2c$^{-/-}$ mice 21 days post-TAC and cultured for further treatment using methods described in earlier examples. The fibroblast number and the fibroblast proliferation (by pH3, a mitosis marker immunostaining) were analyzed after 3 days. The fibroblast numbers and fibroblast proliferation rates were significantly higher in fibroblast isolated from Pip4k2c$^{-/-}$ mice compared to WT mice post-TAC (FIGS. 20A-20J). The collagen synthesis and extracellular matrix protein mRNA markers (as measured by qRT-PCR according to the procedure detailed in Example 1) were also significantly up regulated in Pip4k2c$^{-/-}$ mice fibroblasts (FIGS. 21A-21E). After treating or transfecting the post-TAC Pip4k2c$^{-/-}$ mice fibroblasts with TGF-β inhibitor (SB431542) or Pip4k2c modRNA in vitro, a significant decrease in fibroblast number and fibroblast proliferation was observed (FIGS. 20A-20J). Further, the mRNA expression of fibrosis markers (as measured by qRT-PCR) was also down regulated by the TGF-β inhibitor or Pip4k2c modRNA (FIGS. 21A-21E). The isolated fibroblast from the hearts of Pip4k2c modRNA injected mice 21 days post-TAC were lower in numbers compared to luc. Similarly the fibroblast proliferation rate and fibrosis markers were also down-regulated (the data is not shown).

The in vitro data suggested that inhibition of Pip4k2c induces cardiac fibrosis through the TGF-β pathway and that overexpression of Pip4k2c modRNA or TGF-β inhibition by chemical inhibitor reduces fibrosis in TAC mice model. Taken together these data herein suggest that injection of Pip4k2c modRNA in the TAC mice model significantly reversed cardiac hypertrophy, fibrosis, improved cardiac function and mice survival.

Example 5. Pip4k2c Regulates the Cardiac Hypertrophy Through mTORC1 Signaling To analyze the molecular pathway induced by Pip4k2c post-TAC, protein lysates were first isolated from hearts harvested from WT or Pip4k2c−/− mice from sham or TAC operated mice 21 days after surgery using methods described in previous examples herein. The lysates were then subjected to Western blot analysis (as described in Example 1) to determine phospho-protein and total protein expression of molecular targets within the mTORC1 pathway.

Figure 22A:
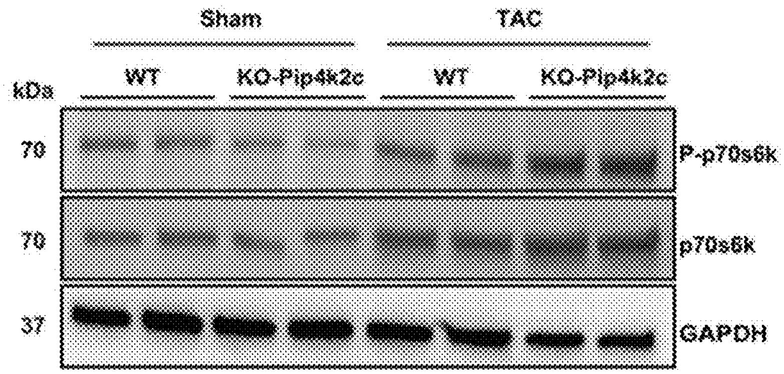
FIGS. 22A-22B depict images of Western blot analysis to evaluate of phospho-p70s6k and total p70s6k protein expression in WT or KO-Pip4k2c 21 days post sham or TAC injury.
Figure 22B:
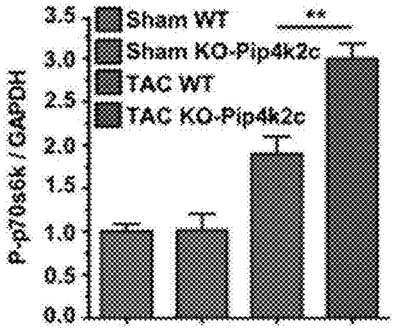

The level of P-p70s6k (phosphorylated ribosomal protein S6 kinase beta-1 (S6K1)) protein, which is known as a marker of mTORC1 pathway, was significantly increased in Pip4k2c−/− mice post TAC (FIGS. 22A-22B). The increased P-p70s6 kinase response represented pro-hypertrophic activity. Thus, the data suggested that Pip4k2c negatively regulates the mTORC1 pathway in the heart post-TAC.

Figure 23:
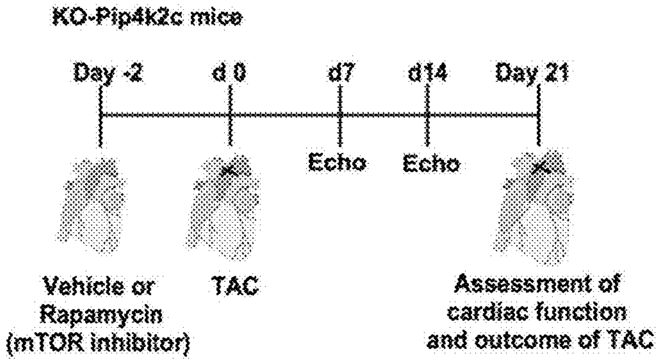
FIG. 23 shows a schematic of the experimental timeline used to evaluate the effect of administration of vehicle or a rapamycin on cardiac function, cardiac hypertrophy and fibrosis in pip4k2c$^{-/-}$ (KO-Pip4k2c) mice 21 days post TAC injury.

The inhibition of the mTORC1 pathway in Pip4k2c−/− mice in vivo might give a clue about the role of mTORC1 pathway in Pip4k2c induced CH post-TAC. To study this, the mTORC1 pathway was inhibited in Pip4k2c−/− mice by administering rapamycin (a well-known mTORC1 chemical inhibitor) to the mice. For rapamycin treatment of these animals, stock a solution of Rapamycin (50 mg/mL) was diluted into vehicle [5% (vol/vol) Tween-80, 5% (vol/vol) PEG 400 (polyethylene glycol, molecular weight 400)] in 1×PBS. Mice were given (3 mg kg-1 d-1) of rapamycin through i.v. injections pre and post-TAC daily. The rapamycin was given before the TAC until 1-week post-TAC (FIG. 23).

Figures 24A, 24B:
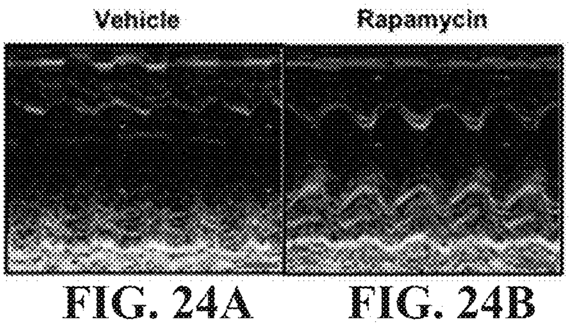
FIGS. 24A-24B show representative echocardiography images of the left ventricle of KO-Pip4k2c mouse 21 days post TAC injury and delivery of vehicle (FIG. 24A) or rapamycin (FIG. 24B). Scale bar=1 mm.
Figure 24C:
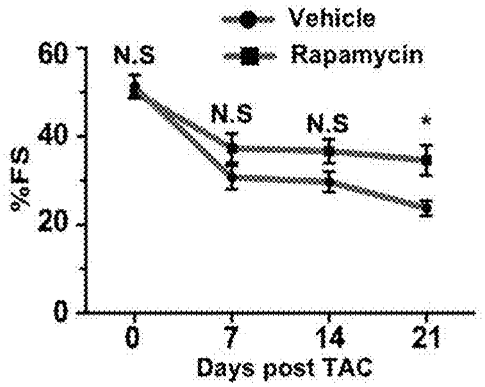
FIGS. 24C-24E show graphs assessing the ECHO evaluation of fractioning shorting (FIG. 24C), LVIDd (FIG. 24D) or LVIDd (FIG. 24E) at either 0, 7, 14 or 21 days post TAC injury and delivery of vehicle or rapamycin to KO-Pip4k2c mouse heart. Unpaired two-tailed t-test was used to measure significance where n=8 for all experimental groups and *=P<0.001, =P<0.01, *=P<0.05, and N.S, Not Significant.
Figure 24D:
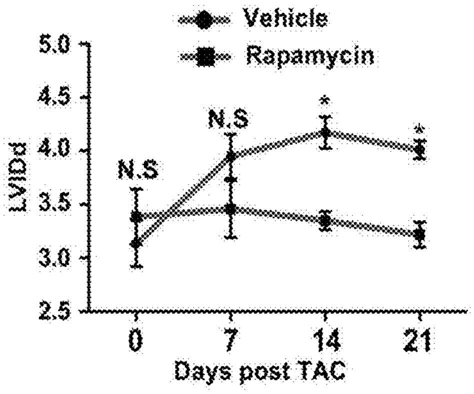
Figure 24E:
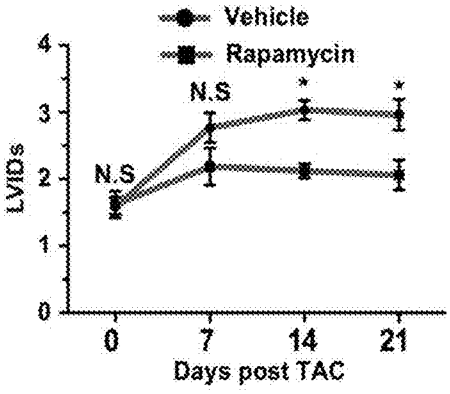
Figure 25A:
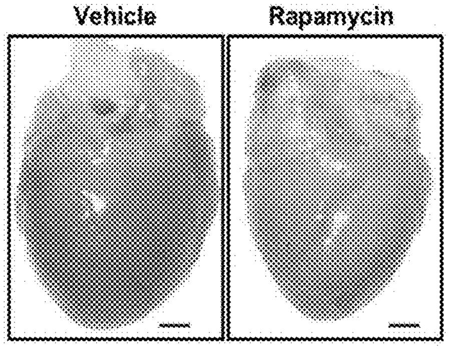
FIGS. 25A-25C depict images of total mouse heart weight analysis.
Figure 25B:
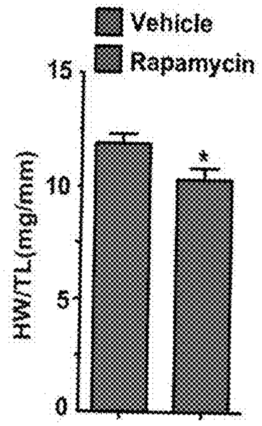
Figure 25C:
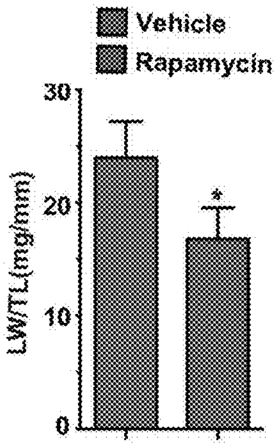
Figure 31A:
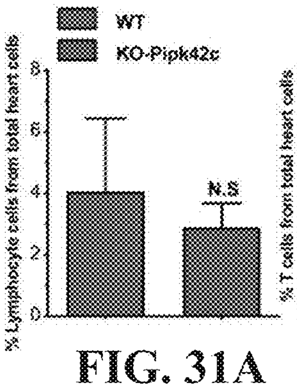
FIGS. 31A-31E depict graphs showing that Pip4k2c depletion did not alter immune cell composition in the heart 21 days post TAC injury as assessed by quantification of flow cytometry of immune cell populations in KO-Pip4k2c versus wild type (WT) mouse hearts 21 days post TAC injury. Graphs show the following immune cell populations which were defined as: Lymphocytes as Lin+ and CD45+ cells (FIG. 31A), T-cells as CD3+ Lymphocytes (FIG. 31B), Myeloid cells as CD11b+ Lymphocytes (FIG. 31C), Macrophages as Myeloid cells that are F4/80+ (FIG. 31D) and Ly6Clow/interm and Neutrophils as Ly6G high and CD11b high (FIG. 31E).
Figure 31B:
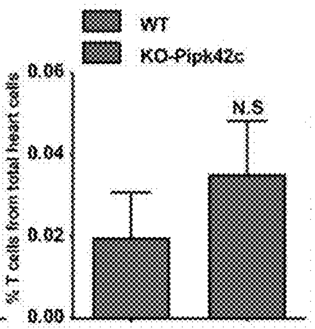
Figure 31C:
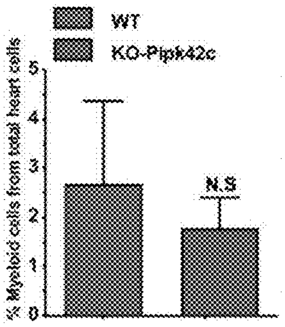
Figure 31D:
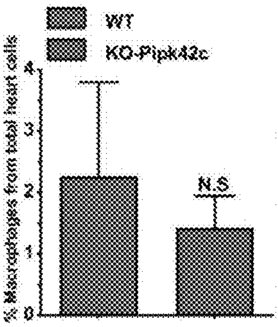
Figure 31E:
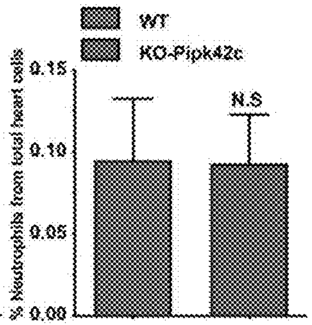

Post-TAC, ECHO was performed on days 0, 7, 14, and 21 to assess cardiac function according to methods described in previous examples (FIGS. 24A-24B). Data showed a partial improvement in % fractioning shorting (cardiac function) in rapamycin-treated mice over time compared to vehicle (FIG. 24C) and both LVIDd and LVIDs parameters were partially improved over time (FIGS. 24D-24E). After 21 days post-TAC, the heart size and HW/TL ratio in the rapamycin-treated mice was reduced compared to the vehicle-treated mice (FIGS. 25A-25B). There was also a decrease in the ratio of lung weight to tibia length 21 days post-TAC in rapamycin-treated mice, suggesting that the rapamycin inhibited the mTORC1 pathway in the TAC mice model (FIG. 25C).

WGA staining was performed according to methods described in previous examples herein to evaluate CM size (cross-sectional area)21 days post TAC injury in the presence of vehicle or rapamycin. The CM size in rapamycin-treated mice hearts was smaller in size compared to vehicle-treated mice (FIGS. 26A-26C).

After 21 days post-TAC, hearts were harvested from rapamycin-treated vehicle-treated mice and RNA was isolated and subjected to qRT-PCT as described in Example 1. The ANP, BNP, and TGF-β1 mRNA expression were decreased (FIGS. 27A and 27B).

Next, fibrosis in these mice was assessed by immunostaining heart sections for Sirius red/Fast green following the method described in previous examples. The fibrotic area in the rapamycin-treated mice hearts was significantly less than that of vehicle-treated mice (FIGS. 28A-28C).

To assess Pip4k2c regulation of TGFβ1, western blot was used to evaluate TGFβ1 21 days post TAC. FIGS. 30A and 30B show that TGFβ1 was significantly higher in KO-Pip4k2c mice than WT and sham-operated WT or KO-Pip4k2c mice, suggesting that Pip4k2c negatively regulates the TGFβ1 pathway in the heart post TAC. Overall data suggest that inhibition of Pip4k2c induced mTORC1 pathway post-TAC, while rapamycin treatment in heart partially reverses cardiac function and cardiac hypertrophy Pip4k2c−/− mice.

The potent and selective inhibitor of the transforming growth factor-β (TGF-β) type I receptor/ALK5, SB4311542 was administered daily KO-Pip4k2c to mice undergoing TAC to further study the TGFβ1 molecular pathways in KO-Pip4k2c mice undergoing TAC. For SB4311542 treatment, the stock solution of SB4311542 (10 mM) was diluted into a vehicle in ethanol. Mice were given (10 mg/kg/day) of SB4311542 through i.v. injections every day for 23 consecutive days (from 2 days before TAC until the experiment ended (day 21)). SB4311542, like rapamycin, partially reduced the detrimental effect of KO-Pip4k2c. More specifically, SB4311542 treatment improved cardiac function, as demonstrated by significantly increased % FS (FIGS. 30C-30D) and notably diminished LVIDd and LVIDs (FIGS. 30E-30G) 21 days after TAC, as compared to KO-Pip4k2c mice treated with vehicle. CF evaluation following delivery of SB4311542 or vehicle revealed smaller heart but not lung weight to tibia length ratios (HW/TL or LW/TL, (FIGS. 30H and 301) accompanied by remarkably decreased fibrosis area (12.5% to 4% % fibrosis in the LV, FIGS. 30J-30L) in KO-Pip4k2c mice treated with SB4311542, compared to vehicle, 21 days post TAC. These results suggest that SB4311542 delivery in KO-Pip4k2c hearts post TAC can partially compensate for the loss of Pip4k2c, which induces fibrosis through the TGFβ1 pathway.

Figure 33A:
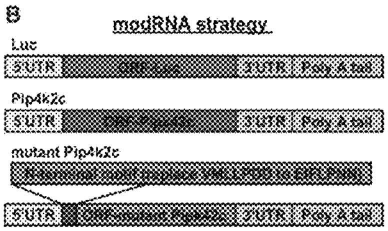
FIGS. 33A-33N depict images showing that N-terminal motif (VMLLPDD) on Pip4k2c was directly responsible for suppression of the TGFβ1 pathway.
Figure 33B:
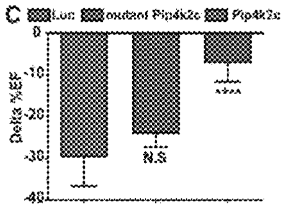
FIGS. 33B-33E are graphs showing echo evaluation of delta % left ventricular ejection fraction (FIG. 33B), fractioning shorting (FIG. 33C), LVIDd (FIG. 33D), and LVIDd (FIG. 33E) 21 days post TAC injury and delivery of Luc, Pip4k2c or mutant Pip4k2c modRNA (Luc-, n=3, Pip4k2c- n=3, mutant Pip4k2c modRNA- n=6).
Figure 33C:
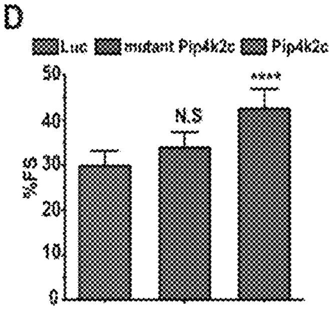
Figure 33D:
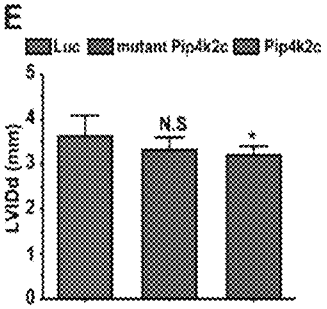
Figure 33E:
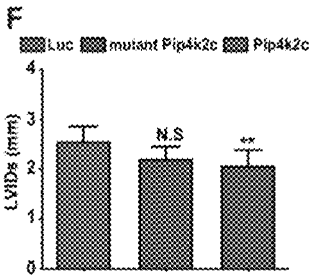
Figure 33F:
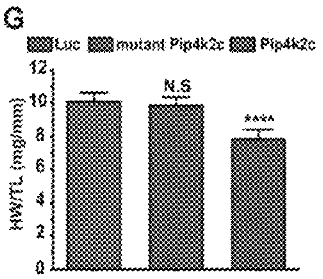
FIG. 33F is a graph showing heart weight to tibia length 21 days post TAC injury and delivery of Luc or Pip4k2c modRNA (Luc-, n=3, Pip4k2c- n=3, mutant Pip4k2c modRNA- n=6).
Figure 33G:
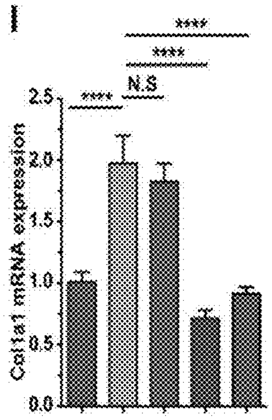
FIGS. 33G-33K are graphs showing qPCR analysis of downstream-TGFβ1 fibrosis marker expression in cardiac fibroblasts isolated and sorted (for the fibroblastic marker CD90) from WT or KO-Pip4k2c hearts 21 days post TAC injury and treated with DMSO (control), TbetaR1/ALK5 inhibitor (SB431542), Pip4k2c or mutant Pip4k2c modRNA where the markers were Col1a1 (FIG. 33G), Col1a2 (FIG. 33H), Col3a1 (FIG. 33I), Ctgf (FIG. 33J) and FN1 (FIG. 33K).
Figure 33H:
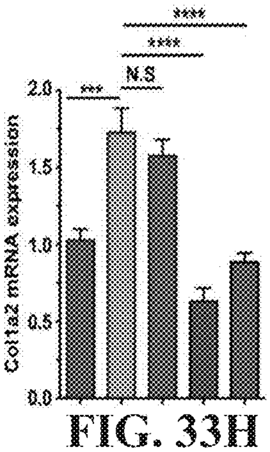
Figure 33I:
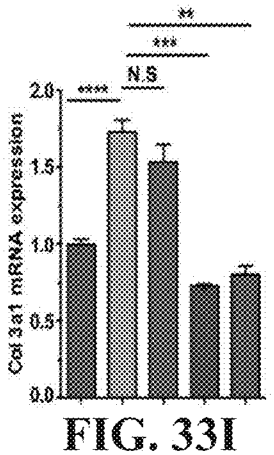
Figure 33J:
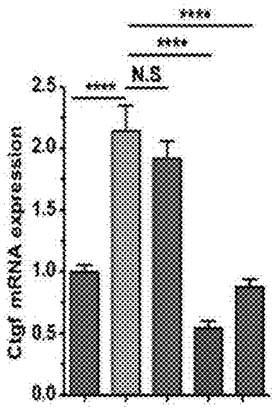
Figure 33K:
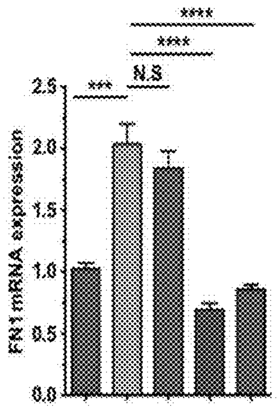
Figure 33L:
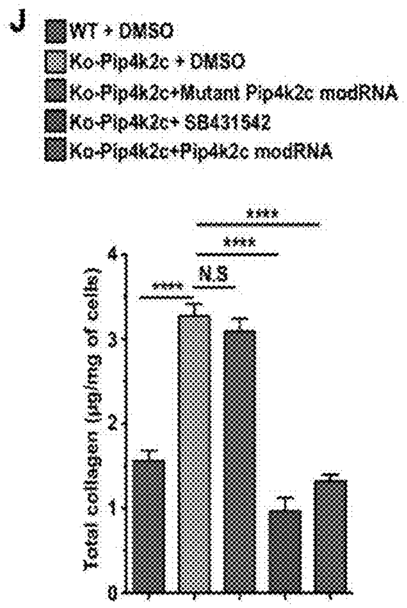
Figure 33M:
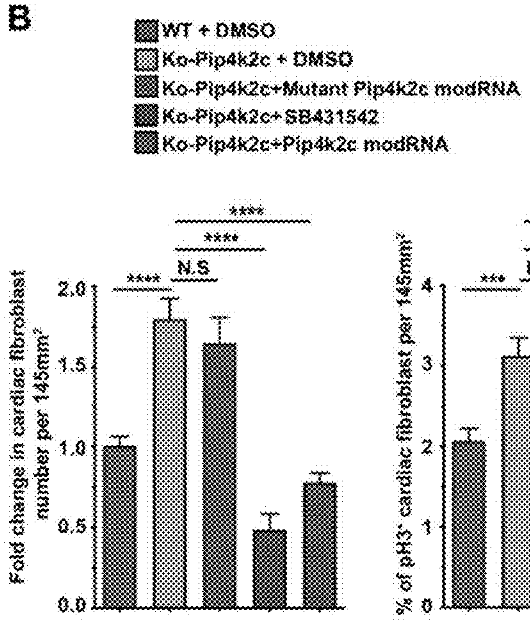
Figure 33N:
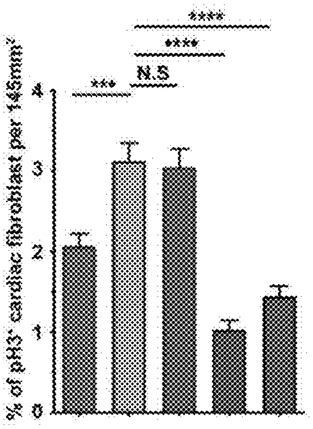

To study the molecular pathways that Pip4k2c induced to prevent CF after TAC; a mutant Pip4k2c modRNA was prepared in which the N-terminal motif (VMLLPDD) was replaced with the mutant motif EIFLPNN (FIG. 33A). This mutation abolished Pip4k2c's ability to inhibit the mTOR pathway. Pip4k2c was compared to mutant Pip4k2c modRNA using the TAC mouse model. Unlike Pip4k2c, the mutant Pip4k2c did not significantly change cardiac function (FIG. 33B-33E) or CH (FIG. 33F), in comparison to Luc control modRNA. In addition, cardiac fibroblasts were isolated and sorted (for CD90, fibroblastic marker) from WT or KO-Pip4k2c hearts 21 days post TAC and treated them with DMSO (control) or the TbetaR1/ALK5 inhibitor (SB431542) or Pip4k2c modRNA or mutant Pip4k2c modRNA. The fibroblasts' expression of fibrosis markers were evaluated, which are the direct targets of TGFβ1 (2 days after treatment, FIGS. 33I-33K), total collagen (3 days after treatment, FIG. 33L), or proliferation (5 days after treatment, Figure S9). The results of these analyses showed that Pipk2c could inhibit TGFβ1 similarly to SB431542, while mutant Pip4k2c cannot, and behaves much like KO-Pip4k2c cardiac fibroblasts. These findings indicate that Pip4k2c negatively regulates TGFβ1 via its N-terminal motif (VMLLPDD) in cardiac fibroblasts, thereby reducing their proliferation and fibrotic activity (FIGS. 33M and 33N). Overall, our data demonstrate that Pip4k2c modRNA inhibits the mTORC1 pathway in CMs and the TGFβ1 pathway in cardiac fibroblasts post TAC, thereby reducing CH and CF, resulting in better cardiac function and survival post TAC injury.

Discussion of Examples 1-5

Examples 1-5 herein show the unexpected results that the Pip4k2c expression is highly regulated in CH and DCM and loss of Pip4k2c in mice induce CH and fibrosis in mice post-TAC. Overexpression of Pip4k2c using a novel modRNA gene delivery system in the heart of the mouse post-TAC model reversed cardiac hypertrophy, reversed fibrosis, and improved cardiac function resulting in the increased survival of the cardiac impaired mice. The loss of Pip4k2c did not result in any major deleterious phenotype during heart development, heart homeostasis, and hearts function; however, as mice age, the amount of Pip4k2c protein in the heart decreased (data not shown). Recently it was shown that Pip4k2c$^{-/-}$ mice develop normally, not protected from obesity, insulin resistance, or diabetes, but rather develop enhanced immune response.

The mTOR pathway is master regulator of protein synthesis, growth and metabolism, which activated after pressure overload in the heart and regulated by growth factors, energy levels, cellular stress, and amino acids. Loss of Pip4k2c in aged mice (above 8-months old) induced mTORC1 pathway in immune cells, but did not cause much difference in uninjured (sham) adult heart. However, mTORC1 was activated at much higher levels in 2 month-old Pip4k2c−/− mice heart post-TAC compared to WT mice of the same age. This suggested that stress or pressure overload was required to strongly activate the mTORC1 pathway in the Pip4k2c−/− mice heart. The use of chemicals or drugs to inhibit mTORC1 pathway to counter the Pip4k2c−/− TAC mice phenotype may have side effects, as these are broader acting chemicals, while mTORC1 genetic regulation, particularly in a tissue specific location, would be of great importance. The Pip4k2c modRNA expression in the mouse heart post-TAC had beneficial effect in cardiac function and heart disease outcome—suggesting that Pip4k2c modRNA can have a therapeutic benefit for heart disease. The expression of modRNA in the heart provides a safer, transient, controlled, dose dependent and flexible gene delivery method. Mammalian cells ubiquitously express Pip4k2c and mTOR proteins, therefore, the data in Example 1-5 have implications beyond the heart, including to potential therapeutic roles for Pip4k2c and Pip4k2c modRNA delivery in hypertrophic and fibrotic diseases, and/or diseases in which altered modulation of Pip4k2c and mTORC1 is involved.

Here, for the first time, we showed the role of Pip4k2c in cardiac fibrosis, which is characterized by abnormal thickening of the heart valves due to inappropriate proliferation of fibroblasts and excess deposition of extracellular matrix in the cardiac muscle. The loss of Pip4k2c induced significant fibrosis in the heart post-TAC, while the fibrosis, fibrosis markers, and TGF-β expression were reduced after injection of Pip4k2c modRNA and/or by inhibiting the TGF-β pathway with a TGF-β inhibitor in the heart (in vivo) and Pip4k2c$^{-/-}$ fibroblasts (in vitro). The data herein suggest that Pip4k2c could regulate fibrotic progression of other fibrotic diseases, wherein administration of Pip4k2c modRNA could also be used as an effective therapy.

FIG. 29 shows how administration of Pip4k2c modRNA significantly attenuated and/or prevented cardiac hypertrophy and fibrosis in the failing heart and improved cardiac function via inhibition of mTORC1 and TGF-β activity—two independent signaling pathways activated in heart failure and other cardiac diseases. The modRNA is transient, safe, controlled, dose dependent gene delivery method, that has only been administered to the heart to upregulate paracrine factors such as VEGF-A, IGF1 and mutate human FSTL1 for propagation of cardiac vascularization, protection, or regeneration respectively post MI, but not for CH and fibrosis to target DCM or heart failure. The novel gene delivery of Pip4k2c modRNA to the heart and subsequent induction of a cardio-protective role in a TAC mouse model supports use of modRNA as a gene delivery system for treatment of heart disease.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present

DISCLOSURE

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles “a” and “an,” as used herein in the specification and in the claims, unless clearly indicated to the contrary, should be understood to mean “at least one.”

The phrase “and/or,” as used herein in the specification and in the claims, should be understood to mean “either or both” of the elements so conjoined, i.e., elements that are conjunctively present in some cases and disjunctively present in other cases. Multiple elements listed with “and/or” should be construed in the same fashion, i.e., “one or more” of the elements so conjoined. Other elements may optionally be present other than the elements specifically identified by the “and/or” clause, whether related or unrelated to those elements specifically identified. Thus, as a non-limiting example, a reference to “A and/or B”, when used in conjunction with open-ended language such as “comprising” can refer, in one embodiment, to A only (optionally including elements other than B); in another embodiment, to B only (optionally including elements other than A); in yet another embodiment, to both A and B (optionally including other elements); etc.

As used herein in the specification and in the claims, “of” should be understood to have the same meaning as “and/or” as defined above. For example, when separating items in a list, “or” or “and/of” shall be interpreted as being inclusive, i.e., the inclusion of at least one, but also including more than one, of a number or list of elements, and, optionally, additional unlisted items. Only terms clearly indicated to the contrary, such as “only one of” or “exactly one of,” or, when used in the claims, “consisting of,” will refer to the inclusion of exactly one element of a number or list of elements. In general, the term “or” as used herein shall only be interpreted as indicating exclusive alternatives (i.e. “one or the other but not both”) when preceded by terms of exclusivity, such as “either,” “one of,” “only one of,” or “exactly one of.” “Consisting essentially of,” when used in the claims, shall have its ordinary meaning as used in the field of patent law.

As used herein in the specification and in the claims, the phrase “at least one,” in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase “at least one” refers, whether related or unrelated to those elements specifically identified. Thus, as a non-limiting example, “at least one of A and B” (or, equivalently, “at least one of A or B,” or, equivalently “at least one of A and/or B”) can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A method of attenuating cardiac hypertrophy in a subject at risk of developing heart failure, the method comprising administering an RNA encoding for type 2 phosphatidylinositol-5-phosphate 4-kinase gamma (pip4k2c) to a heart tissue of the subject, wherein the RNA comprises N1-nethylpseudouridine in place of uridine and an anti-reverse cap analog.

2. The method of claim 1, wherein gene expression of pip4k2c increases after administration of the RNA encoding for pip4k2c to the heart tissue of a subject in need thereof.

3. The method of claim 2, wherein there is an at least 5-fold increase in gene expression of pip4k2c after administration of the RNA encoding for pip4k2c to the heart tissue of the subject.

4. The method of claim 3, wherein the at least 5-fold increase in gene expression of pip4k2c one day after administration of the RNA encoding for pip4k2c is sustained for at least 8 days in the heart tissue of the subject.

5. The method of claim 1, wherein an activity of mammalian target of rapamycin complex 1 (mTORC1), transforming growth factor beta (TGFβ), or a combination thereof is inhibited after administration of the RNA encoding for pip4k2c to the heart tissue of the subject.

6. The method of claim 5, wherein mTORC1 and TGFβ are inhibited after administration of the RNA encoding for pip4k2c to the heart tissue of the subject.

7. The method of claim 1, wherein administering the RNA encoding for pip4k2c to the heart tissue of the subject increases life expectancy by at least 10% compared to an untreated subject with identical disease condition and predicted outcome.

8. The method of claim 1, wherein administering the RNA encoding for pip4k2c to the heart tissue of the subject improves heart function by at least 10% compared to an untreated subject with identical disease condition and predicted outcome.

9. The method of claim 1, wherein administering the RNA encoding for pip4k2c to the heart tissue of the subject in need thereof reduces cardiac fibrosis by at least 5% compared to an untreated subject with identical disease condition and predicted outcome.

10. The method of claim 1, wherein administering the RNA encoding for pip4k2c to the heart tissue of the subject in need thereof reverses cardiac hypertrophy by at least 10% compared to an untreated subject with identical disease condition and predicted outcome.

11. A method of attenuating cardiac hypertrophy in a subject at risk of developing heart failure, the method comprising:

a) preparing an RNA encoding for type 2 phosphatidylinositol-5-phosphate 4-kinase gamma (pip4k2c), wherein the prepared RNA does not elicit an immune response compared to exogenous RNA after local administration; and b) locally administering the RNA encoding for pip4k2c to a heart tissue of the subject; wherein gene expression of pip4k2c increases after at least one administration.

12. The method of claim 11, wherein the RNA encoding for pip4k2c is locally administered to the heart tissue of a subject in need thereof at least once every 20 days.

13. The method of claim 11, wherein life expectancy is increased by at least 40% 20 days after one local administration of the RNA encoding for pip4k2c to the heart tissue of the subject compared to an untreated subject with identical disease condition and predicted outcome.

* * * * *

SEQUENCE LISTING

<160> NUMBER OF SEQ ID NOS: 37

<210> SEQ ID NO 1
<211> LENGTH: 1265
<212> TYPE: DNA
<213> ORGANISM: Artificial Sequence
<220> FEATURE:
<223> OTHER INFORMATION: Synthesized Sequence

<400> SEQUENCE: 1
atggcgtcct cctcggtccc accagccacg gtatcggcgg cgacagcagg ccccggccca 60
ggtttcggct tcgcctccaa gaccaagaag aagcatttcg tgcagcagaa ggtgaaggtg 120
ttccgggcgg ccgacccgct ggtgggtgtg ttcctgtggg gcgtagccca ctcgatcaat 180
gagctcagcc aggtgcctcc cccggtgatg ctgctgccag atgactttaa ggccagctcc 240
aagatcaagg tcaacaatca ccttttccac agggaaaatc tgcccagtca tttcaagttc 300
aaggagtatt gtccccaggt cttcaggaac ctccgtgatc gatttggcat tgatgaccaa 360
gattacttgg tgtcccttac ccgaaacccc cccagcgaaa gtgaaggcag tgatggtcgc 420
ttccttatct cctacgatcg gactctggtc atcaaagaag tatccagtga ggacattgct 480
gacatgcata gcaacctctc caactatcac cagtacattg tgaagtgcca tggcaacacg 540
cttctgcccc agttcctggg gatgtaccga gtcagtgtgg acaacgaaga cagctacatg 600
cttgtgatgc gcaatatgtt tagccaccgt cttcctgtgc acaggaagta tgacctcaag 660
ggttccctag tgtcccggga agccagcgat aaggaaaagg ttaaagaatt gcccaccctt 720
aaggatatgg actttctcaa caagaaccag aaagtatata ttggtgaaga ggagaagaaa 780
atatttctgg agaagctgaa gagagatgtg gagtttctag tgcagctgaa gatcatggac 840
tacagccttc tgctaggcat ccacgacatc attcggggct ctgaaccaga ggaggaagcg 900
cccgtgcggg aggatgagtc agaggtggat ggggactgca gcctgactgg acctcctgct 960
ctggtgggct cctatggcac ctccccagag ggtatcggag gctacatcca ttcccatcgg 1020
cccctgggcc caggagagtt tgagtccttc attgatgtct atgccatccg gagtgctgaa 1080
ggagcccccc agaaggaggt ctacttcatg ggcctcattg atatccttac acagtatgat 1140
gctaagaaga aagcagctca tgcagccaaa actgtcaagc atggggctgg ggcagagatc 1200
tctactgtcc atccggagca gtatgctaag cgattcctgg attttattac caacatcttt 1260
gccta 1265

<210> SEQ ID NO 2
<211> LENGTH: 20
<212> TYPE: DNA
<213> ORGANISM: Artificial Sequence
<220> FEATURE:
<223> OTHER INFORMATION: Synthesized Sequence

<400> SEQUENCE: 2
ggagactatg gcgtcctcct 20

<210> SEQ ID NO 3
<211> LENGTH: 20
<212> TYPE: DNA
<213> ORGANISM: Artificial Sequence
<220> FEATURE:
<223> OTHER INFORMATION: Synthesized Sequence

<400> SEQUENCE: 3
ccggaacacc ttcactttct 20

<210> SEQ ID NO 4
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 4
agtccctgcc ctttgtacac a 21

<210> SEQ ID NO 5
<211> LENGTH: 18
<212> TYPE: DNA
<213> ORGANISM: Artificial Sequence
<220> FEATURE:
<223> OTHER INFORMATION: Synthesized Sequence

<400> SEQUENCE: 5
gatccgaggg cctcacta 18

<210> SEQ ID NO 6
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 6
aggaagccga ggttttaact g 21

<210> SEQ ID NO 7
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 7
aggacgctca taagtgtcac c 21

<210> SEQ ID NO 8
<211> LENGTH: 19
<212> TYPE: DNA
<213> ORGANISM: Artificial Sequence
<220> FEATURE:
<223> OTHER INFORMATION: Synthesized Sequence

<400> SEQUENCE: 8
ctggcaagaa gggagatga 19

<210> SEQ ID NO 9
<211> LENGTH: 20
<212> TYPE: DNA
<213> ORGANISM: Artificial Sequence
<220> FEATURE:
<223> OTHER INFORMATION: Synthesized Sequence

<400> SEQUENCE: 9
caccatccaa accactgaaa 20

<210> SEQ ID NO 10
<211> LENGTH: 20
<212> TYPE: DNA
<213> ORGANISM: Artificial Sequence
<220> FEATURE:
<223> OTHER INFORMATION: Synthesized Sequence

<400> SEQUENCE: 10
aggtcttcct ggagctgatg 20

<210> SEQ ID NO 11
<211> LENGTH: 20
<212> TYPE: DNA
<213> ORGANISM: Artificial Sequence
<220> FEATURE:
<223> OTHER INFORMATION: Synthesized Sequence

<400> SEQUENCE: 11
ccccacaggg ccttctttac 20

<210> SEQ ID NO 12
<211> LENGTH: 20
<212> TYPE: DNA
<213> ORGANISM: Artificial Sequence
<220> FEATURE:
<223> OTHER INFORMATION: Synthesized Sequence

<400> SEQUENCE: 12
gtggggtaga gagtgggtca 20

<210> SEQ ID NO 13
<211> LENGTH: 20
<212> TYPE: DNA

<213> ORGANISM: Artificial Sequence
<220> FEATURE:
<223> OTHER INFORMATION: Synthesized Sequence

<400> SEQUENCE: 13
tgctgtgccc agatgtagag 20

<210> SEQ ID NO 14
<211> LENGTH: 24
<212> TYPE: DNA
<213> ORGANISM: Artificial Sequence
<220> FEATURE:
<223> OTHER INFORMATION: Synthesized Sequence

<400> SEQUENCE: 14
acagcaaatt cacttacaca gttc 24

<210> SEQ ID NO 15
<211> LENGTH: 19
<212> TYPE: DNA
<213> ORGANISM: Artificial Sequence
<220> FEATURE:
<223> OTHER INFORMATION: Synthesized Sequence

<400> SEQUENCE: 15
ctcattgcct tgcgtgttt 19

<210> SEQ ID NO 16
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 16
aggaagccga ggttttaact g 21

<210> SEQ ID NO 17
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 17
aggaagccga ggttttaact g 21

<210> SEQ ID NO 18
<211> LENGTH: 20
<212> TYPE: DNA
<213> ORGANISM: Artificial Sequence
<220> FEATURE:
<223> OTHER INFORMATION: Synthesized Sequence

<400> SEQUENCE: 18
cagaacacca gcctcatcaa 20

<210> SEQ ID NO 19
<211> LENGTH: 20
<212> TYPE: DNA
<213> ORGANISM: Artificial Sequence
<220> FEATURE:
<223> OTHER INFORMATION: Synthesized Sequence

<400> SEQUENCE: 19
gctccttctt cagctcctca 20

<210> SEQ ID NO 20
<211> LENGTH: 19
<212> TYPE: DNA
<213> ORGANISM: Artificial Sequence
<220> FEATURE:
<223> OTHER INFORMATION: Synthesized Sequence

<400> SEQUENCE: 20
gcttccaggc atattggag 19

<210> SEQ ID NO 21
<211> LENGTH: 19
<212> TYPE: DNA
<213> ORGANISM: Artificial Sequence
<220> FEATURE:
<223> OTHER INFORMATION: Synthesized Sequence

<400> SEQUENCE: 21
gggggcatga cctcatctt 19

<210> SEQ ID NO 22
<211> LENGTH: 18
<212> TYPE: DNA
<213> ORGANISM: Artificial Sequence
<220> FEATURE:
<223> OTHER INFORMATION: Synthesized Sequence

<400> SEQUENCE: 22
aagggtctgg ctgctttg 18

<210> SEQ ID NO 23
<211> LENGTH: 22
<212> TYPE: DNA
<213> ORGANISM: Artificial Sequence
<220> FEATURE:
<223> OTHER INFORMATION: Synthesized Sequence

<400> SEQUENCE: 23
cagccaggac ttcctcttaa tg 22

<210> SEQ ID NO 24
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 24
aggacgctca taagtgtcac c 21

<210> SEQ ID NO 25
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 25
aggaagccga ggttttaact g 21

<210> SEQ ID NO 26
<211> LENGTH: 20
<212> TYPE: DNA
<213> ORGANISM: Artificial Sequence
<220> FEATURE:

<223> OTHER INFORMATION: Synthesized Sequence

<400> SEQUENCE: 26
gctgccattt ctaataaaga 20

<210> SEQ ID NO 27
<211> LENGTH: 18
<212> TYPE: DNA
<213> ORGANISM: Artificial Sequence
<220> FEATURE:
<223> OTHER INFORMATION: Synthesized Sequence

<400> SEQUENCE: 27
gcacttcctt tcacaaag 18

<210> SEQ ID NO 28
<211> LENGTH: 20
<212> TYPE: DNA
<213> ORGANISM: Artificial Sequence
<220> FEATURE:
<223> OTHER INFORMATION: Synthesized Sequence

<400> SEQUENCE: 28
ttgaaggatg gcaagtatgg 20

<210> SEQ ID NO 29
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 29
cgaaggcatg acctagagtg t 21

<210> SEQ ID NO 30
<211> LENGTH: 27
<212> TYPE: DNA
<213> ORGANISM: Artificial Sequence
<220> FEATURE:
<223> OTHER INFORMATION: Synthesized Sequence

<400> SEQUENCE: 30
aaggacggcc ttctggcaca cgccttt 27

<210> SEQ ID NO 31
<211> LENGTH: 24
<212> TYPE: DNA
<213> ORGANISM: Artificial Sequence
<220> FEATURE:
<223> OTHER INFORMATION: Synthesized Sequence

<400> SEQUENCE: 31
gtggtatagt gggacacata gtgg 24

<210> SEQ ID NO 32
<211> LENGTH: 24
<212> TYPE: DNA
<213> ORGANISM: Artificial Sequence
<220> FEATURE:
<223> OTHER INFORMATION: Synthesized Sequence

<400> SEQUENCE: 32
gagatcaagg ccaatgttcg gagg 24

<210> SEQ ID NO 33
<211> LENGTH: 21
<212> TYPE: DNA
<213> ORGANISM: Artificial Sequence
<220> FEATURE:
<223> OTHER INFORMATION: Synthesized Sequence

<400> SEQUENCE: 33
cggtagtact tattgcccaa g 21

<210> SEQ ID NO 34
<211> LENGTH: 17
<212> TYPE: DNA
<213> ORGANISM: Artificial Sequence
<220> FEATURE:
<223> OTHER INFORMATION: Synthesized Sequence

<400> SEQUENCE: 34
cctgtccaaa ctaaggc 17

<210> SEQ ID NO 35
<211> LENGTH: 19
<212> TYPE: DNA
<213> ORGANISM: Artificial Sequence
<220> FEATURE:
<223> OTHER INFORMATION: Synthesized Sequence

<400> SEQUENCE: 35
ggttttctca tagatggcg 19

<210> SEQ ID NO 36
<211> LENGTH: 3354
<212> TYPE: DNA
<213> ORGANISM: Artificial Sequence
<220> FEATURE:
<223> OTHER INFORMATION: Synthesized Sequence

<400> SEQUENCE: 36
atgacggctg cgcaggtgag caccgcttcc gggtcgggct tcggagtcgc ggctagctcc 60
cgcttccact cgctcgggtg cgcgggagac tatggcgtcc tcctccgtcc ctcccgccac 120
cgcacccgcg gcagctggag gccccggccc gggattcggc ttcgcctcca aaaccaagaa 180
gaagcatttc gtacagcaga aagtgaaggt gttccgggcc gcggacccgc tggtgggcgt 240
gttcctgtgg ggcgtcgctc actcgatcaa tgagctcagc caggtaccgc ccccagtgat 300
gttgctgcca gatgacttta aagccagctc caagatcaag gtcaacaatc actttttcca 360
tagagaaaat cttcccagtc atttcaagtt caaggagtat tgtccccagg tcttcaggaa 420
cctgagagat cggtttgcca tcgatgatca cgattacttg gtgtccctta ctcgaagccc 480
cccaagcgaa actgaaggca gtgatggccg tttccttatc tcctatgacc gcactctggt 540
catcaaggaa gtgtcgagcg aagatattgc ggatatgcac agcaacctct ccaactacca 600
ccagtacata gtgaaatgtc atggcaacac gcttctgccc cagttcctgg gcatgtaccg 660
agtcagtgta gaaaatgaag acagctacat gctcgtgatg cgcaatatgt ttagtcatcg 720
tcttcctgtg cataggaagt atgacctcaa gggctctcta gtgtcccggg aagccagcga 780
taaggaaaag gttaaagaac tgccaacact aaaggatatg gactttctta acaagaacca 840
gaaagtgtat attggtgaag aagaaaagaa agtattcctg gagaagctga agcgagatgt 900
ggagtttcta gtgcagctga agatcatgga ctacagcctc ctgttgggca tccacgacat 960
catccggggc tctgaacccg aggaagaggg gcctgtgagg gaggaggagt ctgagtggga 1020

-continued

```
tggggactgt aacctggctg gacctcccgc cctggtgggc tcctatggta cctcccctga   1080
gggtatcgga ggctacatcc attcccaccg gccactgggc ccaggagagt ttgagtcctt   1140
catcgatgtc tatgctatcc ggagtgcgga gggggccccc cagaaggagg tgtatttcat   1200
gggcctcatt gacattctga cacagtatga tgccaagaag aaagcagctc atgcagccaa   1260
gactgtcaag cacggggcgg gggcagagat ctccactgtc catcctgagc agtatgctaa   1320
gcgattcctg gactttattg ccaacatctt tgcctaagag gctgcctgac tccagggtga   1380
ttgcggcttt atgttggagg tggcgggttc tgagaggctt aggggagctg gacttggccg   1440
ttacttctct tctttgctaa attcaggctg caggctcctt ccatccaaat aacttccttc   1500
tggtggatag ggttttctcg cccaccccag acatacactg tcctttctcc ccttgtccat   1560
ttctctgccc tccctccttg ctcccagtaa gccctcctgc ttctttagag tgttattgtc   1620
gactcttcta agtgccttga tctttgaaaa atatcttgtt tctatgaaat aggaggagct   1680
gggggagggg ttgtttgcca tcttcgggac ctgactgaac agtggacttg gctcaagcaa   1740
ctgcctggat gcacttttgc tgagtggaag aaactgaatg tctggatttt gctgatactt   1800
ttatggggca ctttgtggca tgcttcctcc ctggtaagcc ctggaatgga gggctttcag   1860
gatgctccag atgtgggtgc aggcattcac acatggacag tctggcctgg aggtcaggtg   1920
gggagtggtc agcaggctgg cacctcacaa ggcaggacct aagcctaagc ggacttttgt   1980
gactatgcag atgatggaga aggtccctgt ggagcaacga ctgttcccga ctgttcccgt   2040
tctcccaccc caccccaccc cacgtccacc tctttctgtg agcactttgg gtgcaggagc   2100
ccagaggcta gcggtgcccg agcttaggtg caggtgtgag actcgggctg ctcttcccac   2160
aaccctgtgc cttgctggtg agcagggaga gcagtagagg ccgggacagg tcggagtgca   2220
gggttcattg cctgggtgac accctttctt cctgtctcac tactcctggg cttctttcta   2280
gcagagggga acagtaccat ctccataatt tggggaggat agagctctcg agtgaaggag   2340
cctccgcatc cctggggcat gtgtacctag aactccccct ccttctcaaa accctttctg   2400
gttggagttg ttattctgtc ccatcttcca ctgctaatgt gtctcccagg ggacagatgg   2460
ccttctttgt catctcccct ctccgccccc agagaggagt cagagccata actcaatcca   2520
cccagtcctc tccaaagaca gctgaatatt aatgcacgcc atcctcagaa tggagaggac   2580
ctgctaggca tcttagctct cccagctcgt gcctgtaaag ccagcactca ggaggctctg   2640
agagttcaag tccagcctgg gctactgagt gagacctggt ctcaggaaca ctccaaatag   2700
gtttgggttt gagcgctgga gatcatagct gagttggtag tgtgcttgcc tagcatgtac   2760
aaagctctgg gatccacccc cagcaccact taagccaggc gtggcggtgc acgcctgcac   2820
tcctggccct gggaagtagt ggtaagcagg atggggcatt caaggtcatc gccagttagt   2880
tacttgacga ggttgaggcc agccaaggaa acaggagacc atcttgggga aaatgattct   2940
aaggagagat agattgtctt tgtctctgcc taaagccttt ggaagcaagc cactcatctt   3000
cgctgtttgg cgctctggag gtggggtggg cattgaaggc aaggagctgc tttgctgtgt   3060
gtccatgagg tcctcaggga gaagcccacc tccctcacca aaggaagcag caagatgggt   3120
gcccggttgg ggtgggtggg acctgctgag tctcccatcc ctcaagcaac ctttcccctg   3180
ttgaatgcaa taagtgactc cggtccctta acaactgggg tctcaccgtg cggctgtggt   3240
cgtgggcagt gttgccatct tcacttactg cttccgtttt ccatctgttt tgttaataaa   3300
atatgtatat ttactcccga tatcacaata aaataaatta tttgatctaa gtca         3354
```

-continued

```
<210> SEQ ID NO 37
<211> LENGTH: 1653
<212> TYPE: DNA
<213> ORGANISM: Artificial Sequence
<220> FEATURE:
<223> OTHER INFORMATION: Synthesized Sequence

<400> SEQUENCE: 37

atggccgatg ctaagaacat taagaagggc cctgctccct tctaccctct ggaggatggc      60

accgctggcg agcagctgca caaggccatg aagaggtatg ccctggtgcc tggcaccatt     120

gccttcaccg atgcccacat tgaggtggac atcacctatg ccgagtactt cgagatgtct     180

gtgcgcctgg ccgaggccat gaagaggtac ggcctgaaca ccaaccaccg catcgtggtg     240

tgctctgaga actctctgca gttcttcatg ccagtgctgg gcgccctgtt catcggagtg     300

gccgtggccc ctgctaacga catttacaac gagcgcgagc tgctgaacag catgggcatt     360

tctcagccta ccgtggtgtt cgtgtctaag aagggcctgc agaagatcct gaacgtgcag     420

aagaagctgc ctatcatcca gaagatcatc atcatggact ctaagaccga ctaccagggc     480

ttccagagca tgtacacatt cgtgacatct catctgcctc ctggcttcaa cgagtacgac     540

ttcgtgccag agtctttcga cagggacaaa accattgccc tgatcatgaa cagctctggg     600

tctaccggcc tgcctaaggg cgtggccctg cctcatcgca ccgcctgtgt gcgcttctct     660

cacgcccgcg accctatttt cggcaaccag atcatccccg acaccgctat tctgagcgtg     720

gtgccattcc accacggctt cggcatgttc accaccctgg gctacctgat ttgcggcttt     780

cgggtggtgc tgatgtaccg cttcgaggag gagctgttcc tgcgcagcct gcaagactac     840

aaaattcagt ctgccctgct ggtgccaacc ctgttcagct tcttcgctaa gagcaccctg     900

atcgacaagt acgacctgtc taacctgcac gagattgcct ctggcggcgc cccactgtct     960

aaggaggtgg gcgaagccgt ggccaagcgc tttcatctgc caggcatccg ccagggctac    1020

ggcctgaccg agacaaccag cgccattctg attaccccag agggcgacga caagcctggc    1080

gccgtgggca aggtggtgcc attcttcgag gccaaggtgg tggacctgga caccggcaag    1140

accctgggag tgaaccagcg cggcgagctg tgtgtgcgcg gccctatgat tatgtccggc    1200

tacgtgaata accctgaggc cacaaacgcc ctgatcgaca aggacggctg gctgcactct    1260

ggcgacattg cctactggga cgaggacgag cacttcttca tcgtggaccg cctgaagtct    1320

ctgatcaagt acaagggcta ccaggtggcc ccagccgagc tggagtctat cctgctgcag    1380

caccctaaca ttttcgacgc cggagtggcc ggcctgcccg acgacgatgc cggcgagctg    1440

cctgccgccg tcgtcgtgct ggaacacggc aagaccatga ccgagaagga gatcgtggac    1500

tatgtggcca gccaggtgac aaccgccaag aagctgcgcg gcggagtggt gttcgtggac    1560

gaggtgccca agggcctgac cggcaagctg gacgcccgca agatccgcga gatcctgatc    1620

aaggctaaga aaggcggcaa gatcgccgtg taa                                 1653
```